US011359249B2

(12) United States Patent
Budding et al.

(10) Patent No.: US 11,359,249 B2
(45) Date of Patent: Jun. 14, 2022

(54) MICROBIAL POPULATION ANALYSIS

(71) Applicant: IS-Diagnostics Ltd., Houten (NL)

(72) Inventors: Andries Edward Budding, Amsterdam (NL); Paul Hendrik Maria Savelkoul, Amsterdam (NL)

(73) Assignee: IS-DIAGNOSTICS LTD, Houten (NL)

(*) Notice: Subject to any disclaimer, the term of this patent is extended or adjusted under 35 U.S.C. 154(b) by 440 days.

(21) Appl. No.: 15/309,025

(22) PCT Filed: May 6, 2015

(86) PCT No.: PCT/NL2015/050313
§ 371 (c)(1),
(2) Date: Nov. 4, 2016

(87) PCT Pub. No.: WO2015/170979
PCT Pub. Date: Nov. 12, 2015

(65) Prior Publication Data
US 2017/0159108 A1    Jun. 8, 2017

(30) Foreign Application Priority Data

May 6, 2014   (EP) ..................................... 14167256
May 9, 2014   (EP) ..................................... 14167778

(51) Int. Cl.
*C12Q 1/689*    (2018.01)

(52) U.S. Cl.
CPC ....... *C12Q 1/689* (2013.01); *C12Q 2545/101* (2013.01); *C12Q 2545/114* (2013.01); *C12Q 2600/106* (2013.01); *C12Q 2600/112* (2013.01); *C12Q 2600/16* (2013.01)

(58) Field of Classification Search
CPC .............. C12Q 1/689; C12Q 2545/101; C12Q 2545/114; C12Q 2600/112; C12Q 2600/16
See application file for complete search history.

(56) References Cited

U.S. PATENT DOCUMENTS

| | | | | |
|---|---|---|---|---|
| 6,677,153 B2* | 1/2004 | Iversen | ................... | A61P 17/00 435/375 |
| 2007/0218459 A1* | 9/2007 | Miller | .................. | C12Q 1/6837 435/6.16 |
| 2009/0004643 A1* | 1/2009 | Ecker | .................... | C12Q 1/6872 435/5 |
| 2011/0117564 A1* | 5/2011 | Reshatoff | ............... | C12Q 1/689 435/6.12 |
| 2011/0177976 A1* | 7/2011 | Gordon | ................ | C12Q 1/6883 506/17 |

FOREIGN PATENT DOCUMENTS

| | | | | |
|---|---|---|---|---|
| EP | 1985712 A1 | 10/2008 | | |
| WO | WO-2008125365 A1 | * | 10/2008 | ........... C12Q 1/6844 |

OTHER PUBLICATIONS

IS-pro Microbiota. May 2019. (Year: 2019).*
Grasman et al. The Effect of Viral, Bacterial and Parasitic Infections on the Intestinal Microbiota. Gastroenterology 2013; 144: S-908. (Year: 2013).*
De Meij et al. Microbiota Profiling in Children with Functional Constipation. Gastroenterology 2014; 146: S-420. (Year: 2014).*
De Meij et al. Short-Term and Long-Term Stability of the Intestinal Microbiota in Healthy Children. Gastroenterology 2014; 146: S-347. (Year: 2014).*
Budding, et al., "IS-pro: high-throughput molecular fingerprinting of the intestinal microbiota," The FASEB Journal, Jul. 19, 2010, pp. 4556-4564, vol. 24, No. 11, VU University Medical Center, Amsterdam, The Netherlands.
International Search Report and Written Opinion issued in corresponding application PCT/NL2015/050313 dated Sep. 28, 2016, 12 pgs.
Haegeman, et al., "Robust estimation of microbial diversity in theory and in practice," The ISME Journal, Feb. 14, 2013, pp. 1092-1101, vol. 7, No. 6.
Marchesi, et al., "Towards the Human Colorectal Cancer Microbiome," PLOS One, May 24, 2011, pp. e20447, vol. 6, No. 5.
Rueckert, et al., "Development and field assesment of a quantitative PCT for the detection and enumeration of the noxious bloom-former Anabaena planktonica," retrieved from the internat: URL:http://reserachcommons.waikato.ac.nz/bitstream/handle/10289/2853/developmentandfieldasssment.pdfsequence=1&isAllowed=y (retrieved Oct. 10, 2014).
Sepehri, et al., "Microbial Diversity of Inflamed and Noninflamed Gut Biopsy Issues in Inflammatory Bowel Disease," Inflammatory Bowel Diseases, Jun. 1, 2007, pp. 675-683, vol. 13, No. 6.
Zinser, et al., "Prochlorococcus Ecotype Abundances in the North Atlantic Ocean as Revealed by an Improved Quantitative PCT Method," Applied and Environmental Microbiology, Jan. 1, 2006, pp. 723-732, vol. 72, No. 1.

* cited by examiner

*Primary Examiner* — Angela M. Bertagna
(74) *Attorney, Agent, or Firm* — Dentons US LLP

(57) ABSTRACT

The present invention relates to a method of typing a microbiome for having a desirable or undesirable signature, comprising analyzing the composition of the population of microorganisms in the microbiome based on taxonomic variation in the DNA sequence of the microbial 16S-23S rRNA internal transcribed spacer (ITS) regions in the genomic DNA of the microorganisms, wherein the sequences of conserved DNA regions comprised in the 16S and 23S rRNA sequences flanking said ITS region in the genome of the microorganisms comprise primer binding sites for amplification of the ITS regions.

11 Claims, 55 Drawing Sheets

Specification includes a Sequence Listing.

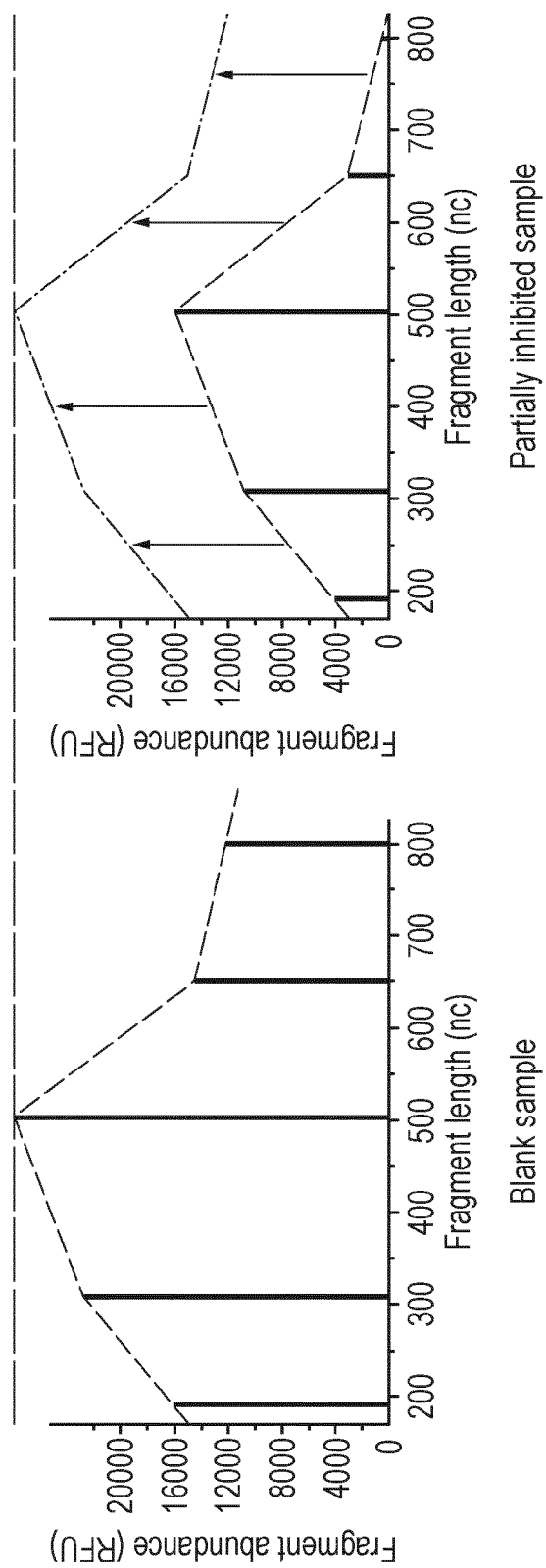

ROC curve per phylum

Proteobacteria
Bacteroidetes
Firmicutes

ROC curve all phyla combined

All phyla

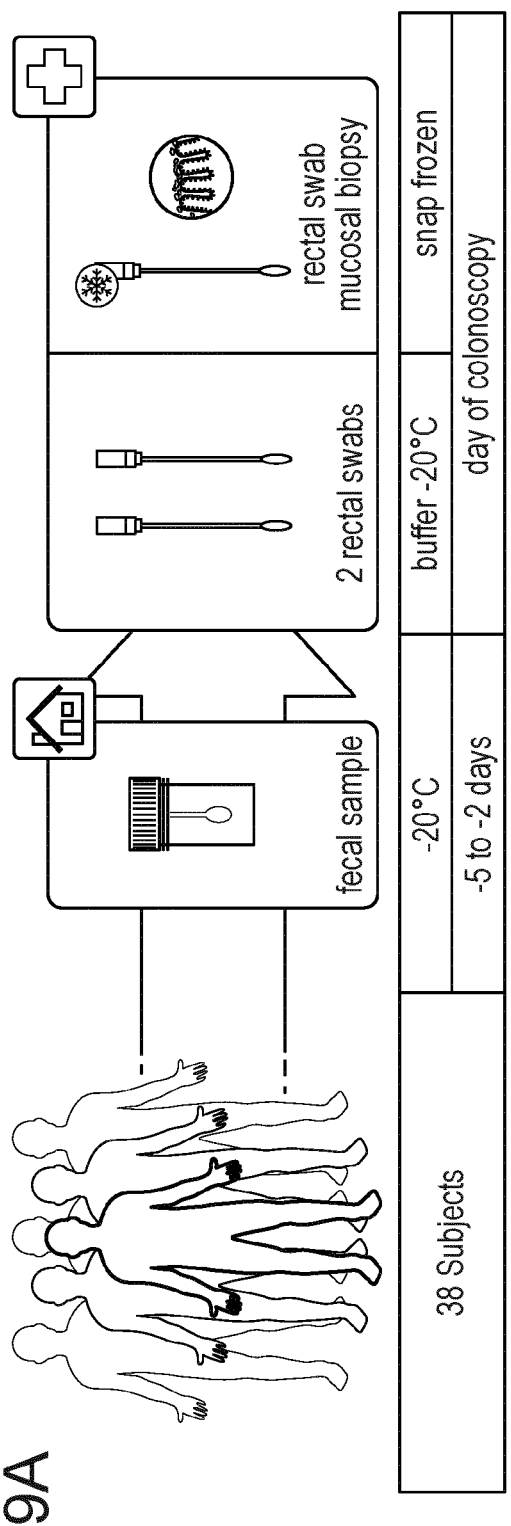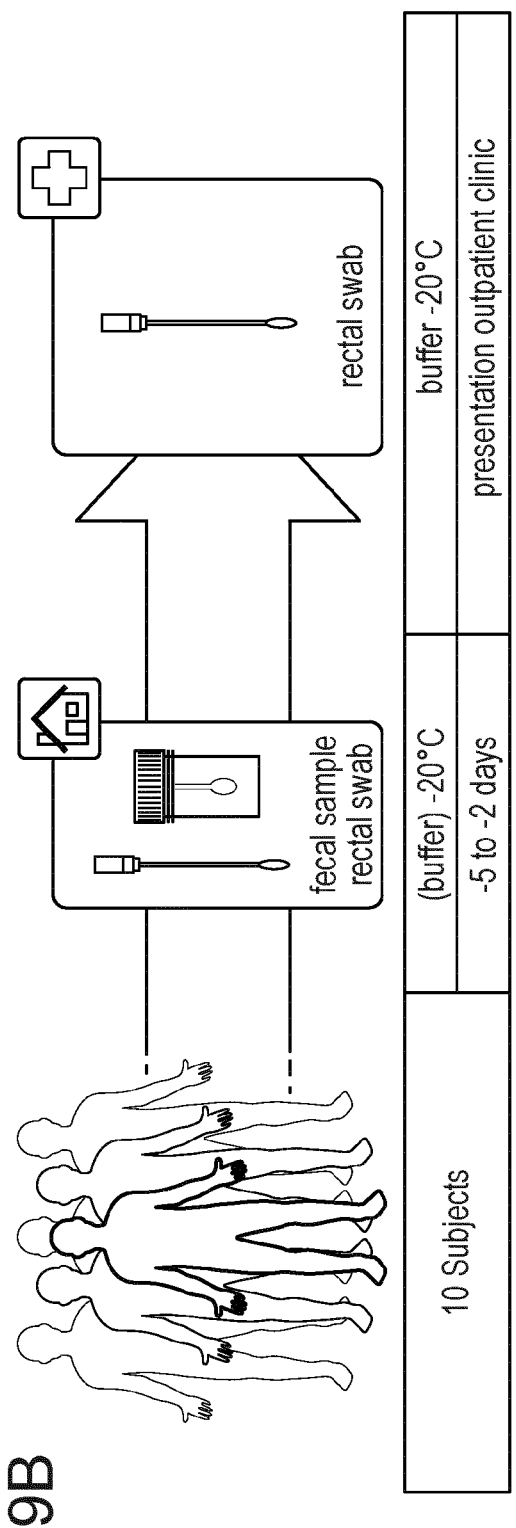

Duplicate swabs in buffer

Swab in buffer vs snap freezing

Swab at home vs polyclinic

Swab vs faeces unprepped

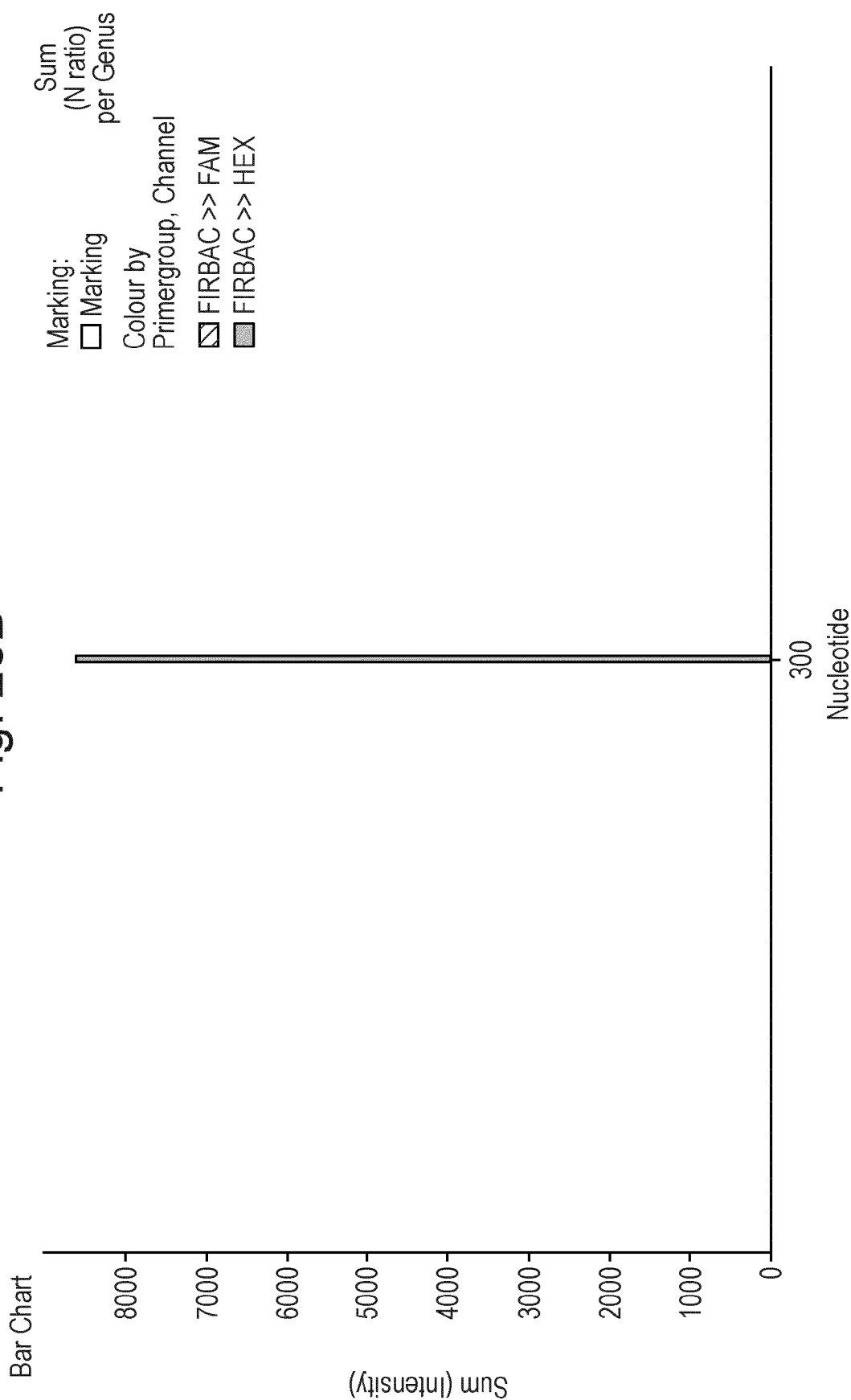

Fig. 28B (Cont.)

IS Lengtes 3

| Source | N ratio | Organism | Genus | Species | Kingdom | Phylum | Class |
|---|---|---|---|---|---|---|---|
| HMP | 0,00 | AEVC01000028... | Streptococcus | cristatus | Bacteria | Firmicutes | Bacili |
| HMP | 0,00 | GL732519 Strept... | Streptococcus | cristatus | Bacteria | Firmicutes | Bacili |

Data limited by:
☐ Marking

Data table:
IS Lengtes 3

Marking:
(None)

Fig. 31 IS-profiles (faeces)

Cumulative profiles (faeces)

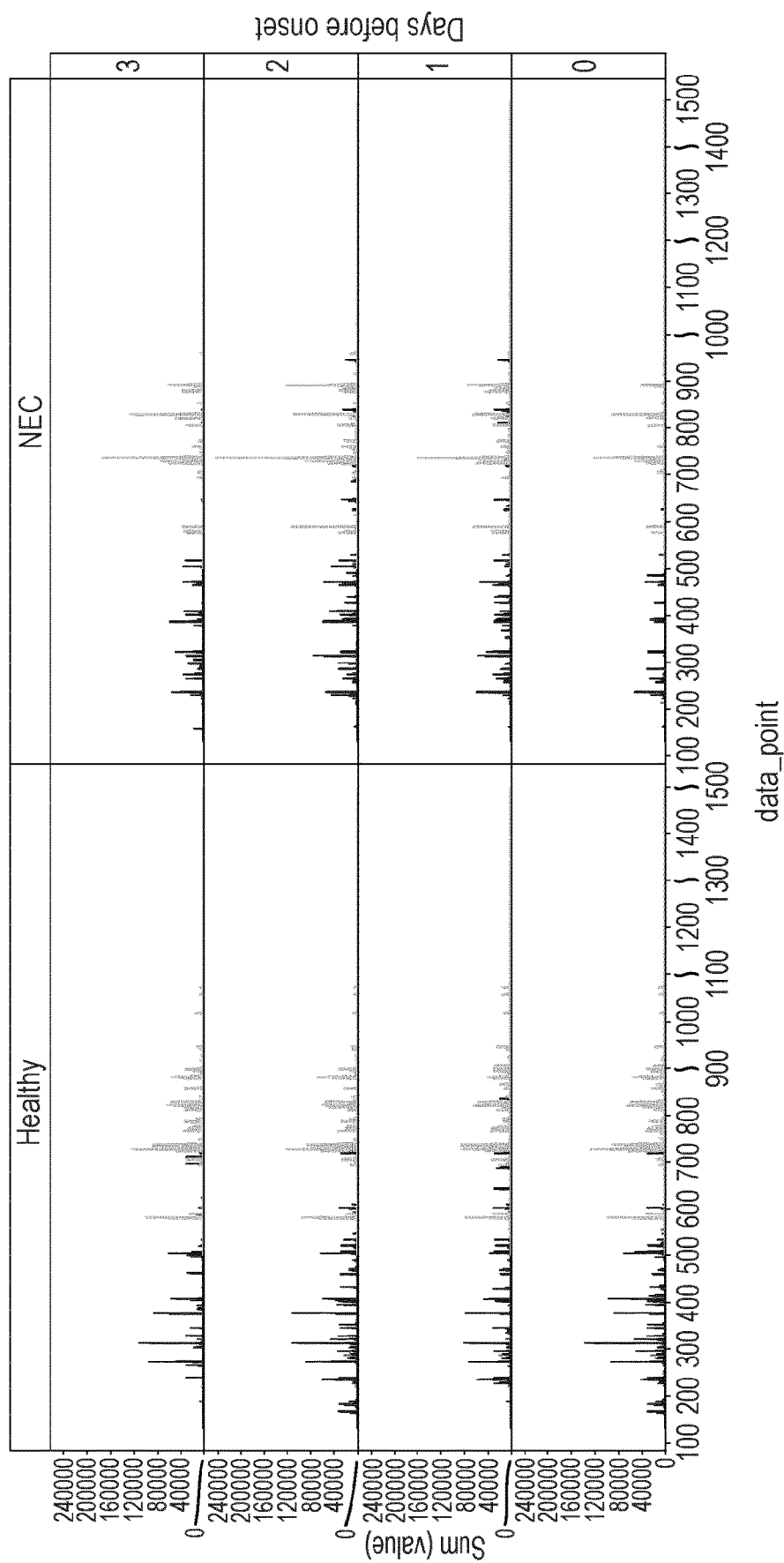

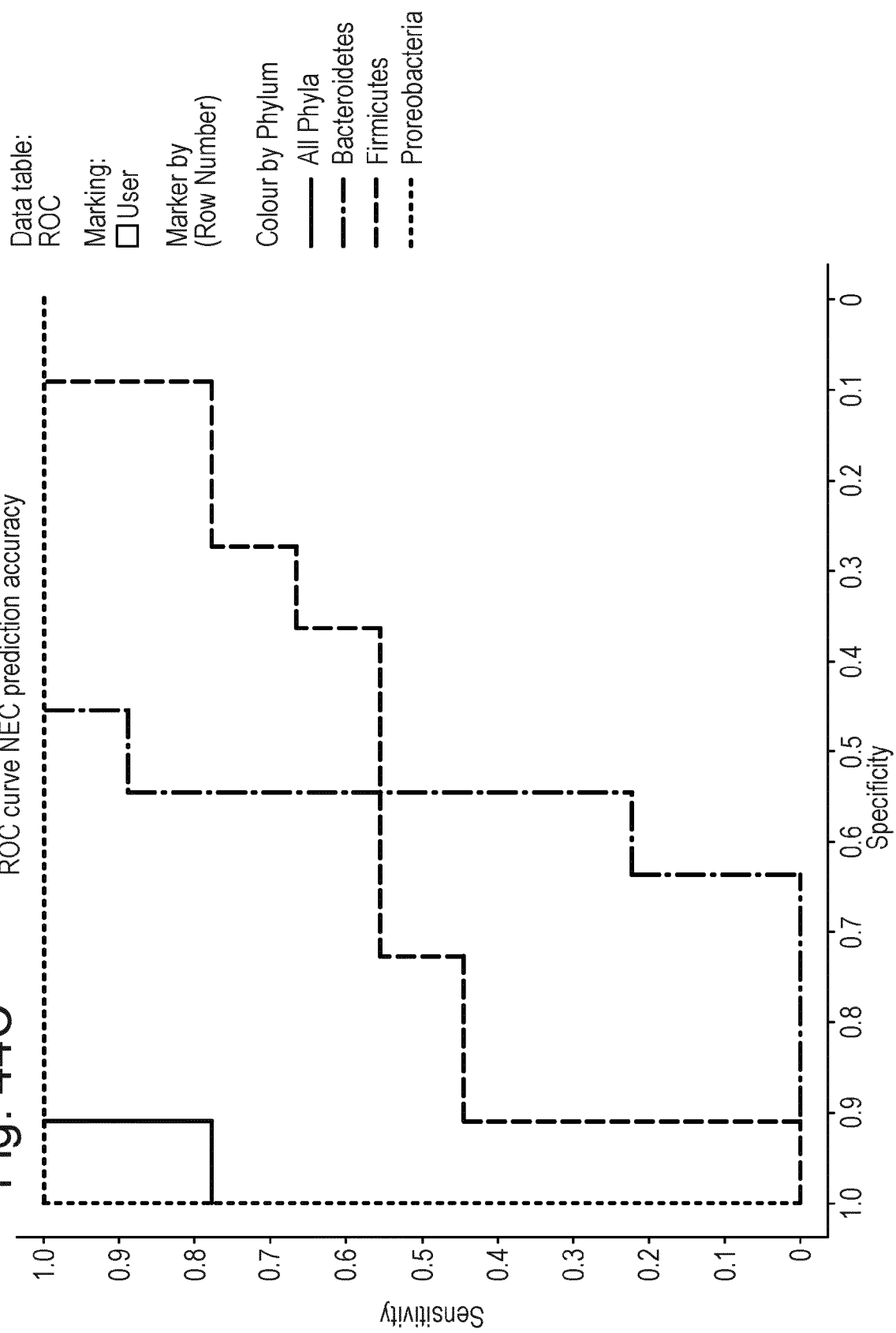

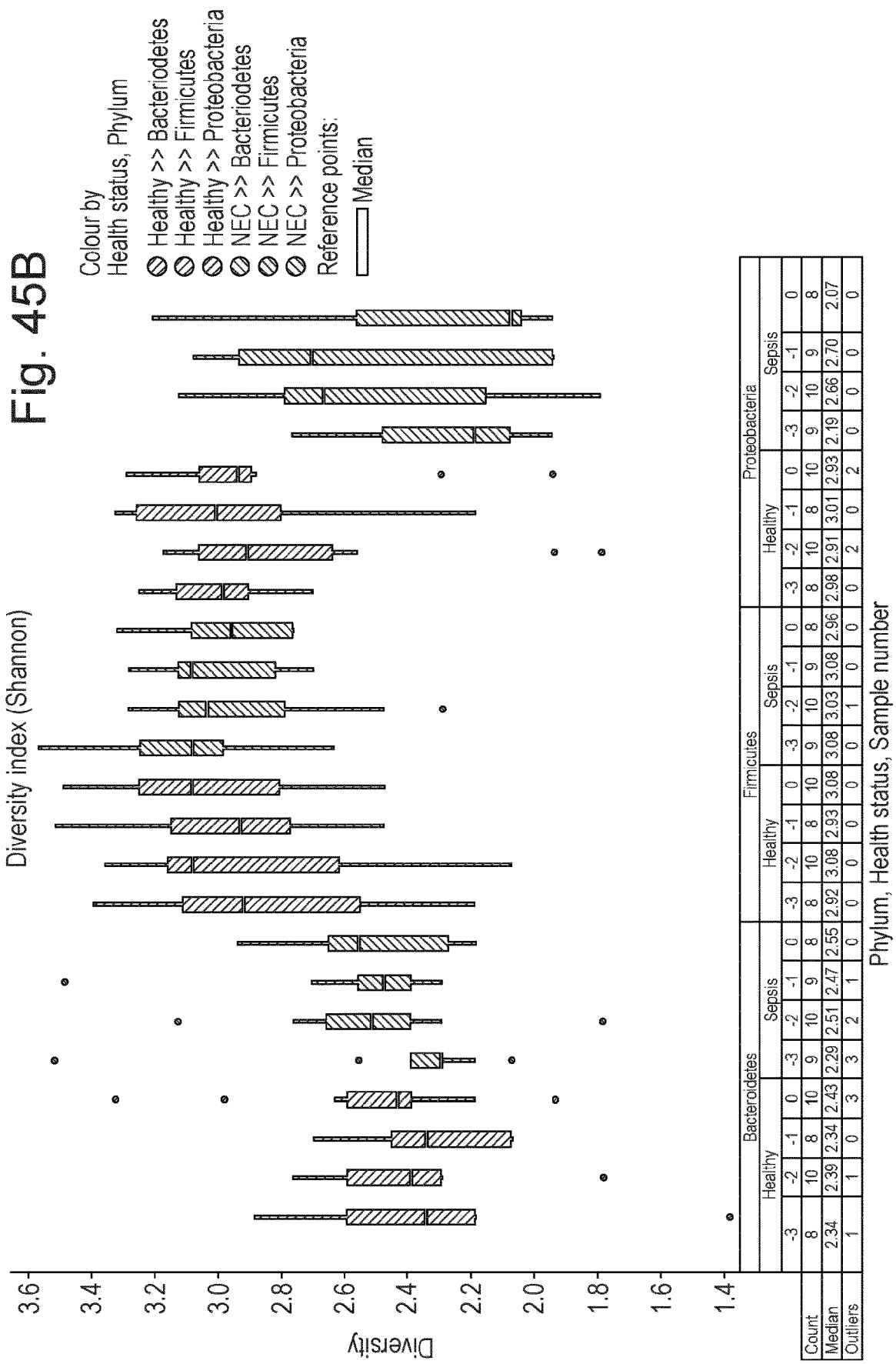

MICROBIAL POPULATION ANALYSIS

CROSS REFERENCE TO RELATED APPLICATIONS

This application is a U.S. National Stage of International Application No. PCT/NL2015/050313, filed May 6, 2015, published in English, which claims the benefit of and priority to European application nos. 14167778.1, filed May 9, 2014 and 14167256.8, filed May 6, 2016.

SEQUENCE LISTING

This application contains a Sequence Listing which has been submitted electronically in ASCII format and which is incorporated by reference in its entirety. Said ASCII file is named P104177US00seqlist_ST25.txt, is 3387 bytes in size and was created on Feb. 1, 2017.

FIELD OF THE INVENTION

The invention is in the field of medical and environmental diagnostics. More specifically, the invention relates to methods of typing and/or monitoring of specific diseases and/or environmental conditions through analysis of the microbial population composition associated with a specific disease condition or environmental condition using polymorphic nucleic acid sequences specific for individual members of the microbial population as a tool for analyzing the microbial population composition. The invention further provides means and methods for calibrating analytical results of microbial population analysis, in particular results of amplification reactions involving amplification of polymorphic nucleic acid sequences, in order to accurately and reproducibly quantify the initial template concentrations in such amplification reactions. The invention further provides methods for typing or analyzing the composition of a population of microorganisms using the said calibration means, and to kits for use in any of the methods of the invention.

BACKGROUND OF THE INVENTION

The use of molecular markers in the assessment and management of disease is becoming more and more common. Some molecular signatures are used diagnostically to help pathologists classify the disease. Molecular markers generally represent biological molecules that originate from the patient's own body cells. But apart from the tissues and organs of the body itself, the microbial community in intimate contact with a patient, such as that of the gastrointestinal tract, provides enormous potential as a reservoir of diagnostically significant information.

Although the correlation between the presence of pathogenic microorganisms and the occurrence of pathogenic disease is diagnostically well accepted, in the case of non-pathogenic disease or disease of unclear pathogenesis, significant correlations with any particular microbial species are rare, and unless a causal relationship between the disease and a specific microbe is established, any correlation may be viewed as having low diagnostic yield.

Analysis of the complex microbial flora of the human intestine is challenging and has hitherto been of limited value in the diagnosis and monitoring of diseases or the effect of therapy. Even PCR-based profiling or "fingerprinting" of microbial populations has thus far aided sparsely in the diagnosis and/or monitoring of diseases. The reason is that these microbial populations differ greatly between individual patients, preventing the ready recognition of specific disease signatures. Although a prevalence of certain species within the colonic microbiome of patients may sometimes be recognized when a comparison is made with healthy subjects, the overall composition of the microbial population is considered to vary too much between individual subjects to allow the identification of disease-specific signatures of the microbiome. As long as it is impossible to assess the meaning of diversity in one population of microorganisms to another, the step from correlation to diagnosing is seriously impeded.

Cultivation techniques have proven inadequate for the purpose of qualitatively describing complex microbial populations, and PCR-based methods are considered to provide a better insight in the true presence of individual members in the community, even if these members are uncultivable. Nonetheless, PCR-based techniques have also shown to have low reproducibility. The reason for this is not entirely clear. The present inventors have noted that two independent PCR amplification reactions performed on different samples are notoriously difficult to compare when attempting to correlate the amount of template present to the amount of products obtained.

Therefore, there is still a need for tools that can improve the reproducibility of PCR techniques applied to mixed microbial populations. Hence, there is also still a need for tools that can aid in classifying disease based on microbial population composition analysis. It is an aim of the present invention to overcome the problems of the prior art microbial profiling techniques. It is further an aim of the present invention to provide microbial profiles that can be used to distinguish healthy from diseased conditions.

SUMMARY OF THE INVENTION

The present inventors have now surprisingly found that disease-specific profiles of the population composition of microorganisms can be obtained, despite inter-patient variability. The present inventors have further found that nucleic acid amplification-based methods for microbial population profiling can actually be used in typing or classifying of certain diseases. The present inventors have further found that embodiments of such typing methods can benefit from an internal amplification standard that allows for the correction of length-specific amplification efficiencies in a single amplification reaction, thereby allowing for the removal of inter-sample variability in the amplification efficiency of sequence-length polymorphisms.

The present inventors have established new methods for nucleic acid amplification-based analysis of complex microbial populations that allow for the determination of initial amounts of specific microbial nucleic acids in a sample and to thereby quantify individual members in a mixed microbial population more accurately and reproducibly. The inventors have further found that a reference database of reference profiles can be determinative in the finding of significant correlations between the microbiome and specific diseases.

In one aspect, the present invention provides a method for diagnosing or monitoring a disease or condition in a patient comprising typing a microbiome from said patient for having a healthy or diseased signature, comprising analyzing the composition of the population of microorganisms in said microbiome based on taxonomic variation in the DNA sequence of the microbial 16S-23S rRNA internal transcribed spacer (ITS) regions in the genomic DNA of said microorganisms, wherein the sequences of conserved DNA regions comprised in the 16S and 23S rRNA sequences flanking said ITS region in the genome of said microorganisms comprise primer binding sites for amplification of said ITS regions, said analyzing comprising the steps of:

a) providing a sample of genomic DNA from the microorganisms in a microbiome;

b) performing a PCR amplification reaction on said sample of genomic DNA using at least one set of PCR amplification primers directed to said flanking conserved DNA regions to thereby amplify and provide amplification products of said ITS regions comprised in said genomic DNA sample;

c) analyzing said amplification products based on length differences in said amplification products to thereby provide a test signature of the composition of the population of microorganisms in said microbiome;

d) comparing said test signature with at least one reference signature of a microbiome of a healthy patient and/or with at least one reference signature of a microbiome of a diseased patient, preferably by clustering of ITS profiles, and classifying the test signature as a signature of a microbiome of a healthy patient or as a signature of a microbiome of a diseased patient, wherein said at least one set of PCR amplification primers comprises:

a set of PCR amplification primers for amplifying the 16S-23S rRNA internal transcribed spacer (ITS) regions in the genomic DNA of microorganisms belonging to the phylum Firmicutes, and a set of PCR amplification primers for amplifying the 16S-23S rRNA internal transcribed spacer (ITS) regions in the genomic DNA of microorganisms belonging to the phylum Bacteroidetes.

In another aspect, the present invention provides a method of typing a microbiome for having a desirable or undesirable signature, comprising analyzing the composition of the population of microorganisms in said microbiome based on taxonomic variation in the DNA sequence of the microbial 16S-23S rRNA internal transcribed spacer (ITS) regions in the genomic DNA of said microorganisms, wherein the sequences of conserved DNA regions comprised in the 16S and 23S rRNA sequences flanking said ITS region in the genome of said microorganisms comprise primer binding sites for amplification of said ITS regions, said analyzing comprising the steps of:

a) providing a sample of genomic DNA from the microorganisms in a microbiome;

b) performing a PCR amplification reaction on said sample of genomic DNA using at least one set of PCR amplification primers directed to said flanking conserved DNA regions to thereby amplify and provide amplification products of said ITS regions comprised in said genomic DNA sample;

c) analyzing said amplification products based on length differences in said amplification products to thereby provide a test signature of the composition of the population of microorganisms in said microbiome;

d) comparing said test signature with at least one reference signature of a desirable microbiome and/or with at least one reference signature of an undesirable microbiome, preferably by clustering of ITS profiles, and classifying the test signature as a signature of a desirable microbiome or as a signature of an undesirable microbiome, wherein said at least one set of PCR amplification primers comprises:

a set of PCR amplification primers for amplifying the 16S-23S rRNA internal transcribed spacer (ITS) regions in the genomic DNA of microorganisms belonging to the phylum Firmicutes, and a set of PCR amplification primers for amplifying the 16S-23S rRNA internal transcribed spacer (ITS) regions in the genomic DNA of microorganisms belonging to the phylum Bacteroidetes.

In preferred embodiments of the above method, said at least one set of PCR amplification primers further comprises:

a set of PCR amplification primers for amplifying the 16S-23S rRNA internal transcribed spacer (ITS) regions in the genomic DNA of microorganisms belonging to the phylum Proteobacteria.

In preferred embodiments of the above method, said set of PCR amplification primers for amplifying the 16S-23S rRNA internal transcribed spacer (ITS) regions in the genomic DNA of the phyla Firmicutes and Bacteroidetes comprises the use of:

a) the forward primer 5'-CTGGATCACCTCCTTTCTAWG-3' (SEQ ID NO: 1) comprising a first fluorescent label, b) the forward primer 5'-CTGGAACACCTCCTTTCTGGA-3' (SEQ ID NO: 2) comprising a second fluorescent label;

c) and three unlabeled reverse primers 5'-AGGCATCCACCGTGCGCCCT-3' (SEQ ID NO: 3); 5'-AGGCATTCACCRTGCGCCCT-3' (SEQ ID NO: 4); and 5'-AGGCATCCRCCATGCGCCCT-3' (SEQ ID NO: 5).

In preferred embodiments of the above method, said set of PCR amplification primers for amplifying the 16S-23S rRNA internal transcribed spacer (ITS) regions in the genomic DNA of the phylum Proteobacteria comprises the use of:

a) the forward primer 5'-CCGCCCGTCACACCATGG-3' (SEQ ID NO: 6)

b) at least one of the reverse primers selected from the group consisting of

5'-AATCTCGGTTGATTTCTTTTCCT-3' (SEQ ID NO: 7),
5'-AATCTCGGTTGATTTCTTCTCCT-3' (SEQ ID NO: 8),
5'-AATCTCTTTTGATTTCTTTTCCTCG-3' (SEQ ID NO: 9),
5'-AATCTCATTTGATGTCTTTTCCTCG-3' (SEQ ID NO: 10),
5'-AATCTCTTTTGATTTCTTTTCCTTCG-3' (SEQ ID NO: 11),
5'-AATCTCTCTTGATTTCTTTTCCTTCG-3' (SEQ ID NO: 12),
5'-AATCTCAATTGATTTCTTTTCCTAAGG-3' (SEQ ID NO: 13), wherein at least one of said primers comprises a fluorescent label.

In preferred embodiments of the above method, said microbiome is the microbiome of the respiratory tract, oral cavity, skin, gastrointestinal tract, or urogenital tract or that of urine, saliva, sputum, pus, wound fluid, or feces, preferably of the human body, or the microbiome associated with soil, waterbodies or plants.

In preferred embodiments of the above method, said undesirable microbiome is a) the intestinal microbiome of a subject suffering from:

a digestive tract or gastrointestinal disorder including inflammatory bowel disease (IBD), diverticulitis, irritable bowel syndrome (IBS), coeliac, lactose intolerance, Necrotising Enterocolitis (NEC), *Clostridium Difficile* Associated Diarrhea and colorectal cancer, or a comorbid disorder selected from the group consisting of attention-deficit/hyperactivity disorder (ADHD), obsessive-compulsive disorder (OCD), anxiety, stress, eating disorder, major depressive disorder (MDD), bipolar disorder, depression, and schizophrenia, a systemic disease including arthritis, sarcoidosis, mixed connective tissue disease, spondylitis ankylopoetica, osteoporosis, juvenile idiopathic arthritis, osteoarthritis, rheumatoid arthritis, sepsis, Behçet's disease, Sjögren's syndrome, fibromyalgia, sclerodermia, Raynaud's phenomenon, and systemic lupus erythematosus, a skin disorder including psoriasis, eczema, acne, or rosacea, b) the skin microbiome of a subject suffering from a skin disorder including psoriasis, eczema, acne, or rosacea, c) a wound microbiome of a subject suffering from chronic wound, including a diabetic ulcer, or ulcer associated with vascular disease, d) a urogenital tract microbiome or vaginal flora of a female having low fertility or having a low probability of success of an in vitro fertilization or embryo transfer procedure, or suffering from bacterial vaginosis, e) an oral microbiome of a subject suffering from an oral, nasal or oropharyncheal disorder including periodontitis, periimplantitis, and oro-nasopharyngeal carcinoma, f) a pulmonary microbiome in a pulmonary sample selected from bronchoalveolar lavage, a sputum sample and a lung biopsy of a subject suffering from a disorder that affects the upper or lower respiratory tract, including respiratory infection, chronic obstructive pulmonary disease (COPD), asthma, cystic fibrosis and lung cancer, g) a microbiome in a liquor sample, a pleural sample, a blood sample, a urine sample, an abscess sample, or a tissue sample of an organ in a subject suspected of suffering from a microbial infection, h) a microbiome in a sample of environmental, plant, animal or food origin or in a sample of a pharmaceutical or chemical product intended to be devoid of microbes or microbial DNA.

In another aspect, the present invention provides a method of analyzing the composition of a microbiome based on taxonomic variation in the DNA sequence of the microbial 16S-23S rRNA internal transcribed spacer (ITS) regions in the genomic DNA of the microorganisms in said microbiome, wherein the sequences of conserved DNA regions comprised in the 16S and 23S rRNA sequences flanking said ITS region in the genomic DNA of said microorganisms comprise primer binding sites for amplification of said ITS regions, said method comprising the steps of:

a) providing a sample of genomic DNA from a microbiome;
b) providing a PCR calibrator system, comprising a set of PCR amplification primers at least one of which primers comprises a label, and a set of at least two PCR calibrators, each PCR calibrator consisting of a DNA fragment comprising a spacer region having a DNA sequence of a given length flanked by upstream and downstream adapter DNA sequences that comprise primer binding sites for binding of said PCR amplification primers wherein said set of PCR amplification primers is for PCR amplifying the spacer region DNA sequence of all PCR calibrators in said set of at least two PCR calibrators, wherein the spacer region DNA sequence comprised in each of said PCR calibrators in said set of at least two PCR calibrators is of a different length, and wherein each PCR calibrator in said set of at least two PCR calibrators is present in equal amount or in a known amount relative to other PCR calibrators in said set;
c) adding said set of at least two PCR calibrators from said PCR calibrator system to said sample of genomic DNA;
d) performing a PCR amplification reaction on said sample of genomic DNA comprising said set of at least two PCR calibrators using said set of PCR amplification primers from said PCR calibrator system as a first set of amplification primers to amplify and provide amplification products of said ITS region(s) comprised in said set of at least two PCR calibrators, and using at least a second set of PCR amplification primers directed to said flanking conserved DNA regions to thereby co-amplify and provide amplification products of said ITS regions comprised in said sample of genomic DNA, and;
e) providing a standard curve by determining the PCR amplification efficiency of each of said at least two PCR calibrators from said PCR calibrator system in said PCR amplification reaction of step d) and expressing said PCR amplification efficiency as a function of the length of the DNA sequence of the ITS region;
f) determining the length-specific amplification efficiency for ITS regions of different length comprised in said genomic DNA sample and amplified in step d) using the standard curve as provided in step e);
g) determining the abundance of microbial 16S-23S rRNA internal transcribed spacer (ITS) regions of different length in said microbiome using the length-specific amplification efficiencies determined in step f), and
h) analyzing the composition of a population of microorganisms based on the abundances of ITS regions of different length determined in step g).

In preferred embodiments of the above method, said standard curve is based on at least five PCR calibrators of different length ranging in length from 50 to 1200 bps.

In preferred embodiments of the above method, said step d) of performing a PCR amplification reaction on said sample of genomic DNA using at least a set of PCR amplification primers directed to said flanking conserved DNA regions comprises the use of a set of PCR amplification primers for amplifying the 16S-23S rRNA internal transcribed spacer (ITS) regions in the genomic DNA of the phyla Firmicutes and Bacteroidetes and a set of PCR amplification primers for amplifying the 16S-23S rRNA internal transcribed spacer (ITS) regions in the genomic DNA of the phylum Proteobacteria.

In preferred embodiments of the above method, said set of PCR amplification primers for amplifying the 16S-23S rRNA internal transcribed spacer (ITS) regions in the genomic DNA of the phyla Firmicutes and Bacteroidetes comprises the use of:
a) the forward primer 5'-CTGGATCACCTCCTTTCTAWG-3' (SEQ ID NO: 1) comprising a first fluorescent label,
b) the forward primer 5'-CTGGAACACCTCCTTTCTGGA-3' (SEQ ID NO: 2) comprising a second fluorescent label;
c) and three unlabeled reverse primers 5'-AGGCATCCACCGTGCGCCCT-3' (SEQ ID NO: 3); 5'-AGGCATTCACCRTGCGCCCT-3' (SEQ ID NO: 4); and 5'-AGGCATCCRCCATGCGCCCT-3' (SEQ ID NO: 5).

In preferred embodiments of the above method, said set of PCR amplification primers for amplifying the 16S-23S rRNA internal transcribed spacer (ITS) regions in the genomic DNA of the phylum Proteobacteria comprises the use of:
a) the forward primer 5'-CCGCCCGTCACACCATGG-3' (SEQ ID NO: 6)
b) at least one of the reverse primers selected from the group consisting of 5'-AATCTCGGTTGATTTCTTTTCCT- 3' (SEQ ID NO: 7), 5'-AATCTCGGTTGATTTCTTCTCCT-3' (SEQ ID NO: 8), 5' AATCTCTTTTGAT-TTCTTTTCCTCG-3' (SEQ ID NO: 9), 5'-AATCTCATTTGATGTCTTTTCCTCG-3' (SEQ ID NO: 10), 5'-AATCTCTTTTGATTTCTTTTCCTTCG-3' (SEQ ID NO: 11), 5'-AATCTCTCTTGATTTCTTTTCCTTCG-3' (SEQ ID NO: 12), 5'-AATCTCAATTGAT-TTCTTTTCCTAAGG-3' (SEQ ID NO: 13), wherein at least one of said primers comprises a fluorescent label.

In other preferred embodiments of the above method, said microbiome is the microbiome of the respiratory tract, oral cavity, skin, gastrointestinal tract, or urogenital tract or that of urine, saliva, sputum, pus, wound fluid, or feces, preferably of the human body, or the microbiome associated with soil, waterbodies or plants.

In another aspect, the present invention provides a method for diagnosing or monitoring a digestive tract or gastrointestinal disorder in a patient, wherein the disorder is selected from the group consisting of digestive tract or gastrointestinal disorders associated with inflammatory bowel disease (IBD), diverticulitis, irritable bowel syndrome (IBS), coeliac, lactose intolerance, Necrotising Enterocolitis (NEC), *Clostridium Difficile* Associated Diarrhea and colorectal cancer, or comorbid disorder selected from the group consisting of attention-deficit/hyperactivity disorder (ADHD), obsessive-compulsive disorder (OCD), anxiety, stress, eating disorder, major depressive disorder (MDD), bipolar disorder, depression, and schizophrenia, said method comprising performing the method of the present invention on a sample of the intestinal flora of a patient, and optionally treating the patient by pharmacological intervention.

In another aspect, the present invention provides method for diagnosing or monitoring a systemic disease in a patient selected from the group consisting of arthritis, sarcoidosis, mixed connective tissue disease, spondylitis ankylopoetica, osteoporosis, juvenile idiopathic arthritis, osteoarthritis, rheumatoid arthritis, sepsis, Behçet's disease, Sjögren's syndrome, fibromyalgia, sclerodermia, Raynaud's phenomenon, and systemic lupus erythematosus, said method comprising performing the method of any one of claims 1-13 on a sample of the intestinal flora of a patient, and optionally treating the patient by pharmacological intervention.

In another aspect, the present invention provides a method for diagnosing or monitoring a skin disorder or chronic wound in a patient, said method comprising performing the method of the present invention on a sample of the skin, wound flora or intestinal flora of a patient, and optionally treating the patient by pharmacological intervention.

In another aspect, the present invention provides a method of determining fertility or the probability of success of an in vitro fertilization or embryo transfer procedure in a female, said method comprising performing the method of the present invention on a sample of the vaginal flora, and optionally treating the patient by pharmacological intervention.

In another aspect, the present invention provides a method for diagnosing or monitoring bacterial vaginosis, said method comprising performing the method of the present invention on a sample of the vaginal flora, and optionally treating the patient by pharmacological intervention, preferably wherein the pharmacological intervention comprises the systemic or topical administration of an antibiotic, preferably metronidazole, clindamycin, amoxicillin-clavulanate or fluconazole.

In another aspect, the present invention provides a method for diagnosing or monitoring an oral, nasal or oropharyncheal disorder selected from periodontitis, periimplantitis, and oro-nasopharyngeal carcinoma said method comprising performing the method of the present invention on a sample of the oral flora, and optionally treating the patient by pharmacological intervention, preferably wherein the pharmacological intervention comprises the systemic, topical or local administration of an antibiotic or antineoplastic agent.

In another aspect, the present invention provides a method for diagnosing or monitoring a disorder that affects the upper or lower respiratory tract, selected from respiratory infection, chronic obstructive pulmonary disease (COPD), asthma, cystic fibrosis and lung cancer, said method comprising performing the method of the present invention on a pulmonary sample selected from bronchoalveolar lavage, a sputum sample and a lung biopsy, and optionally treating the patient by pharmacological intervention, preferably wherein the pharmacological intervention comprises the systemic, topical or local administration of an antibiotic agent, anti-inflammatory agent or antineoplastic agent.

In another aspect, the present invention provides a method for diagnosing or monitoring a microbial infection, said method comprising performing the method of the present invention on a liquor sample, a pleural sample, a blood sample, a urine sample, an abscess sample, or a tissue sample of an organ, and optionally treating the patient by pharmacological intervention, preferably wherein the pharmacological intervention comprises the systemic, topical or local administration of an antibiotic agent.

In another aspect, the present invention provides a method for determining the microbial status of a sample, wherein said sample is of environmental, plant, animal or food origin or a sample of a pharmaceutical or chemical product intended to be devoid of microbes or microbial DNA, said method comprising performing the method of the present invention on a sample from said source, and optionally treating the source from which the sample was obtained, wherein said status is indicative of sterility of said sample, quality of the environment, microbial safety of food, or the health of plant or animal, preferably wherein the treatment comprises the reduction of microbial growth in said sample source or elimination of microbes or microbial DNA from said sample source.

In preferred embodiments of all of the above aspects and embodiments, the test signature is characterized in having an increased or decreased diversity in the phylum Firmicutes, Bacteroidetes and/or Proteobacteria compared to the reference signature as calculated using the Shannon index.

In another aspect, the present invention provides a PCR calibrator system, comprising a set of PCR amplification primers at least one of which primers comprises a label, and a set of at least two PCR calibrators, each PCR calibrator consisting of a DNA fragment comprising a spacer region having a DNA sequence of a given length flanked by upstream and downstream adapter DNA sequences that comprise primer binding sites for binding of said PCR amplification primers wherein said set of PCR amplification primers is for PCR amplifying the spacer region DNA sequence of all PCR calibrators in said set of at least two PCR calibrators, wherein the spacer region DNA sequence comprised in each of said PCR calibrators in said set of at least two PCR calibrators is of a different length, and wherein each PCR calibrator in said set of at least two PCR calibrators is present in equal amount or in a known amount relative to other PCR calibrators in said set.

In a preferred embodiment of said aspect, the said spacer region DNA sequence is the sequence of at least a part of a microbial 16S-23S rRNA internal transcribed spacer (ITS) region, and wherein said adapter DNA sequences in said set of at least two PCR calibrators replace the DNA sequences of the conserved DNA regions comprised in the 16S and 23S rRNA gene sequences upstream and downstream of said ITS region in the microbial genome from which said ITS region originates and wherein said adapter DNA sequences have less than 30% sequence identity with the DNA sequences of said conserved DNA regions.

In another preferred embodiment of said aspect, said spacer region DNA sequence is an artificial or semi-artificial DNA sequence of a given length, wherein each spacer region flanked by upstream and downstream adapter DNA sequences in said set of at least two calibrators has a different length. In a highly preferred embodiment, said spacer region DNA sequence consists of the sequence of a part of a microbial 16S-23S rRNA internal transcribed spacer (ITS) region, more preferably, it is at least a part of the consensus DNA sequence of at least 2, 3, 4, 5, or more microorganisms present in the microbiome that is to be analysed.

In another aspect, the present invention provides a set of at least two PCR calibrators as defined herein above, wherein said set is comprised in a single replicon or single amplifiable template, preferably a DNA plasmid. Such a plasmid, when replicated, allows the provision of said at least two PCR calibrators in exact equal amounts.

In another aspect, the present invention provides a method of analyzing the composition of a microbiome based on taxonomic variation in the DNA sequence of the microbial 16S-23S rRNA internal transcribed spacer (ITS) regions in the genomic DNA of the microorganisms in said microbiome, wherein the sequences of conserved DNA regions comprised in the 16S and 23S rRNA sequences flanking said ITS region in the genomic DNA of said microorganisms comprise primer binding sites for amplification of said ITS regions, said method comprising the steps of:

a) providing a sample of genomic DNA from a microbiome;
b) providing a PCR calibrator system as defined herein above;
c) adding said set of at least two PCR calibrators from said PCR calibrator system to said sample of genomic DNA;
d) performing a PCR amplification reaction on said sample of genomic DNA comprising said set of at least two PCR calibrators using said set of PCR amplification primers from said PCR calibrator system as a first set of amplification primers to amplify and provide amplification products of said ITS region(s) comprised in said set of at least two PCR calibrators, and using at least a second set of PCR amplification primers directed to said flanking conserved DNA regions to thereby co-amplify and provide amplification products of said ITS regions comprised in said sample of genomic DNA, and;
e) providing a standard curve by determining the PCR amplification efficiency of each of said at least two PCR calibrators from said PCR calibrator system in said PCR amplification reaction of step d) and expressing said PCR amplification efficiency as a function of the length of the DNA sequence of the ITS region;
f) determining the length-specific amplification efficiency for ITS regions of different length comprised in said genomic DNA sample and amplified in step d) using the standard curve as provided in step e);
g) determining the abundance of microbial 16S-23S rRNA internal transcribed spacer (ITS) regions of different length in said microbiome using the length-specific amplification efficiencies determined in step f), and
h) analyzing the composition of a population of microorganisms based on the abundances of ITS regions of different length determined in step g).

In a preferred embodiment of a method of analyzing the composition of a microbiome as described above, said standard curve is based on at least five PCR calibrators of different length, preferably said PCR calibrators ranging in length from 50 to 1200 bps.

In In another preferred embodiment of a method of analyzing the composition of a microbiome as described above, said step d) of performing a PCR amplification reaction on said sample of genomic DNA using at least a second set of PCR amplification primers directed to said flanking conserved DNA regions comprises the use of a set of PCR amplification primers for amplifying the 16S-23S rRNA internal transcribed spacer (ITS) regions in the genomic DNA of the phyla Firmicutes and Bacteroidetes and a set of PCR amplification primers for amplifying the 16S-23S rRNA internal transcribed spacer (ITS) regions in the genomic DNA of the phylum Proteobacteria. Preferably, said set of PCR amplification primers for amplifying the 16S-23S rRNA internal transcribed spacer (ITS) regions in the genomic DNA of the phyla Firmicutes and Bacteroidetes comprises the use of:

a) the forward primer 5'-CTGGAT-CACCTCCTTTCTAWG-3' (SEQ ID NO: 1) comprising a first fluorescent label,
b) the forward primer 5'-CTG-GAACACCTCCTTTCTGGA-3' (SEQ ID NO: 2) comprising a second fluorescent label;
c) and three unlabeled reverse primers 5'-AGGCATC-CACCGTGCGCCCT-3' (SEQ ID NO: 3); 5'-AGGCATT-CACCRTGCGCCCT-3' (SEQ ID NO: 4); and 5'-AGG-CATCCRCCATGCGCCCT-3' (SEQ ID NO: 5). Preferably, said set of PCR amplification primers for amplifying the 16S-23S rRNA internal transcribed spacer (ITS) regions in the genomic DNA of the phylum Proteobacteria comprises the use of a) the forward primer 5'-CCGCCCGTCACACCATGG-3' (SEQ ID NO: 6) comprising a first fluorescent label,
b) and seven unlabeled reverse primers 5'-AATCTCGGTTGATTTCTTTTCCT-3' (SEQ ID NO: 7); 5'-AATCTCGGTTGATTTCTTCTCCT-3' (SEQ ID NO: 8); 5'-AATCTCTTTTGATTTCTTTTCCTCG-3' (SEQ ID NO: 9); 5'-AATCTCATTTGATGTCTTTTCCTCG-3' (SEQ ID NO: 10); 5'-AATCTCTTTTGATTTCTTTTCCTTCG-3' (SEQ ID NO: 11); 5'-AATCTCTCTTGAT-TTCTTTTCCTTCG-3' (SEQ ID NO: 12); and 5' AATCT-CAATTGATTTCTTTTCCTAAGG-3' (SEQ ID NO: 13)

In yet another preferred embodiment of a method of analyzing the composition of a microbiome as described above, said microbiome is the microbiome of the respiratory tract, oral cavity, skin, gastrointestinal tract, or urogenital tract, or that of urine, saliva, sputum, pus, wound fluid, or feces, preferably of the human body, or the microbiome associated with soil, waterbodies or plants.

In another aspect, the present invention provides a method for diagnosing or monitoring a digestive tract or gastrointestinal disorder in a patient, wherein the disorder is selected from the group consisting of digestive tract or gastrointestinal disorders associated with inflammatory bowel disease (IBD), diverticulitis, irritable bowel syndrome (IBS), coeliac, lactose intolerance, Necrotising Enterocolitis (NEC), *Clostridium Difficile* Associated Diarrhea and colorectal cancer, or comorbid disorder selected from the group consisting of attention-deficit/hyperactivity disorder (ADHD), obsessive-compulsive disorder (OCD), anxiety, stress, eating disorder, major depressive disorder (MDD), bipolar disorder, depression, and schizophrenia, said method comprising performing the method of analyzing the composition of a microbiome as described above using the PCR calibrator system on a sample of the intestinal flora, and optionally treating the patient by pharmacological intervention.

The term "monitoring" as used herein refers to supervising or controlling the disease state of a subject or a microbial state of an environment. The term includes reference detection of any changes in the disease state of a subject or a microbial state of an environment. Preferably, the monitoring methods in aspects of this invention are applied for monitoring patients in which a change in their disease state is not evident (i.e. the patient does not show obvious signs of a change in the disease state, or the patient is suspected of having a certain disease). The term "monitoring" in this aspect, and in other aspects of this invention, refers to the detection of any changes over time, for instance as part of longitudinal follow up studies to detect changes in the microbiome resulting from therapy or intervention.

In a preferred embodiment of the method as described above, said sample of intestinal flora is a sample obtained from small or large intestine, preferably colon or rectum, more preferably obtained in the form of a feces sample or rectal swab or in the form of a biopsy specimen of gastrointestinal mucosa.

In a further preferred embodiment of a method as described above, IBD is selected from Crohn's disease, colitis ulcerosa, collageneous colitis, lymfocytic colitis, ischemic colitis, microscopic colitis, Behçet's syndrome, diversion colitis, diverticular colitis, eosinophilic colitis, and radiation colitis.

In yet another preferred embodiment of a method for diagnosing or monitoring a digestive tract or gastrointestinal disorder the digestive tract or gastrointestinal disorder is treated by pharmacological intervention with therapeutic agents selected from an anti-inflammatory agent and an antibiotic agent, TNF-alfa inhibitors, including infliximab and adalimumab, and 5-ASA formulations, including sulfasalazine and mesalazine.

In another aspect, the present invention provides a method for diagnosing or monitoring a systemic disease in a patient, wherein the systemic disease is selected from the group consisting of arthritis, sarcoidosis, mixed connective tissue disease, spondylitis ankylopoetica, osteoporosis, juvenile idiopathic arthritis, osteoarthritis, rheumatoid arthritis, sepsis, Behçet's disease, Sjögren's syndrome, fibromyalgia, sclerodermia, Raynaud's phenomenon, and systemic lupus erythematosus, said method comprising performing the method of analyzing the composition of a microbiome as described above using the PCR calibrator system on a sample of said patient, preferably on a sample of the intestinal flora, and optionally treating the patient by pharmacological intervention.

In a preferred embodiment of the method as described above, said sample of intestinal flora is a sample obtained from small or large intestine, preferably colon or rectum, more preferably obtained in the form of a feces sample or rectal swab or in the form of a biopsy specimen of gastrointestinal mucosa.

In yet another preferred embodiment of a method for diagnosing or monitoring a digestive tract or gastrointestinal disorder the digestive tract or gastrointestinal disorder is treated by pharmacological intervention with therapeutic agents selected from an anti-inflammatory agent and an antibiotic agent.

In yet another preferred embodiment of a method for diagnosing or monitoring a digestive tract or gastrointestinal disorder as described above, the comorbid disorder is attention-deficit/hyperactivity disorder (ADHD) and the pharmacological intervention comprises treating the patient with a methylphenidate stimulant, preferably selected from the group consisting of Adderall®, Concerta®, Vyvanse®, and Ritalin.

In yet another preferred embodiment of a method for diagnosing or monitoring a digestive tract or gastrointestinal disorder as described above, the comorbid disorder is selected from obsessive-compulsive disorder (OCD), anxiety, stress, major depressive disorder (MDD), bipolar disorder symptoms, depression, and schizophrenia, and the pharmacological intervention comprises treating the patient with an antidepressant, preferably selective serotonin reuptake inhibitors (SSRIs), more preferably fluoxetine, citalopram, escitalopram, paroxetine, or sertraline; or an antipsychotic selected from the group consisting of aripiprazole, asenapine, clozapine, iloperidone, olanzapine, paliperidone, quetiapine, risperidone, and ziprasidone.

In yet another preferred embodiment of a method for diagnosing or monitoring a digestive tract or gastrointestinal disorder as described above, the eating disorder is anorexia nervosa or bulimia nervosa, and the pharmacological intervention comprises the administration of an antidepressant, preferably selective serotonin reuptake inhibitors (SSRIs), more preferably fluoxetine, citalopram, escitalopram, paroxetine, or sertraline; an antihistamine; or an antipsychotic, preferably selected from the group consisting of aripiprazole, asenapine, clozapine, iloperidone, olanzapine, paliperidone, quetiapine, risperidone, and ziprasidone.

In another aspect, the present invention provides a method for diagnosing or monitoring a skin disorder or chronic wound in a patient, said method comprising performing the method of analyzing the composition of a microbiome as described above using the PCR calibrator system on a sample of the skin or wound flora, and optionally treating the patient by pharmacological intervention.

In a preferred embodiment of the method for diagnosing or monitoring a skin disorder or chronic wound in a patient, said skin disorder is psoriasis, eczema, acne, rosacea, diabetic ulcer, and ulcers associated with vascular disease and wherein the pharmacological intervention comprises the administration of an antibiotic agent or anti-inflammatory agent.

Antibiotic agents in aspects of this invention are preferably selected from the group consisting of amikacin, amoxicillin, anidulafungin, azithromycin, bacitracin, benzylpenicillin, cephalexin, cefazolin, cefotaxime, ceftaroline, ceftazidime, ceftriaxone, cefuroxime, ciprofloxacin, clarithromycin, clindamycin, clotrimazole, co-amoxiclav, dalfopristin, daptomycin, doxycycline, ertapenem, erythromycin, ethambutol, flucloxacillin, fluconazole, fosfomycin, framycetin, fusidic acid, gentamycin, imipenem, isoniazid, itraconazole, ketoconazole, metronidazole, meropenem, miconazole, moxifloxacin, mupirocin, neomycin sulphate, nitrofurantoin, ofloxacin, phenoxymethylpenicillin, piperacillin, piperacillin/tazobactam, pyarazinamide, quinupristin, rifampicin, rifaximin, teicoplanin, tetracycline, tobramycin, tigecycline, trimethoprim, sulphametoxazole, vancomycin and combinations thereof.

Anti-inflammatory agents in aspects of this invention are preferably selected from the group consisting of cortisone, hydrocortisone, prednisone and prednisolone, methylprednisolone, dexamethasone, triamcinolone, mometasone, fluticasone, betamethasone, halometasone, desonide and combinations thereof.

In another aspect, the present invention provides a method of determining fertility or the probability of success of an in vitro fertilization or embryo transfer procedure in a female, said method comprising performing the method of analyzing the composition of a microbiome as described above using the PCR calibrator system on a sample of the vaginal flora, and optionally treating the patient by pharmacological intervention.

In another aspect, the present invention provides a method for diagnosing or monitoring bacterial vaginosis, said method comprising performing the method of analyzing the composition of a microbiome as described above using the PCR calibrator system of the present invention on a sample of the vaginal flora, and optionally treating the patient by pharmacological intervention, preferably the pharmacological intervention comprises the systemic or topical administration of an antibiotic agent, preferably metronidazole or clindamycin.

In another aspect, the present invention provides a method for diagnosing or monitoring an oral, nasal or oropharyncheal disorder selected from periodontitis, periimplantitis, and oro-nasopharyngeal carcinoma, said method comprising performing the method of analyzing the composition of a microbiome as described above using the PCR calibrator system on a sample of the oral flora, and optionally treating the patient by pharmacological intervention, by removal or revision of a dental implant, or by radiotherapy, preferably wherein the pharmacological intervention comprises the systemic, topical or local administration of an antibiotic or antineoplastic agent.

Antineoplastic agents in aspects of this invention are preferably selected from the group consisting of busulfan, cyclophosphamide, ifosfamide, thiotepa; mechlorethamine, melphalan, lomustine, semustine, streptozocin, capecitabine, cladribine, cytarabine, floxuridine, fludarabine, fluorouracil, mercaptopurine, methotrexate, thioguanine, bleomycin sulfate, dactinomycin, daunorubicin, doxorubicin, epirubicin, idarubicin, mitomycin, mitoxantrone, pentostatin, plicamycin, streptozocin, vinblastine, vincristine, vindesine, vinorelbine tartrate, estrogens, androgens, progestins, corticosteroids, aminoglutethimide, chlorotrianisene, flutamide, goserelin, leuprolide, tamoxifen, etoposide, teniposide, paclitaxel, carboplatin, cisplatin, asparaginase, dacarbazine, hydroxyurea, interferons, levamisole, mitotane, procarbazine, tretinoin, and combinations thereof.

In another aspect, the present invention provides a method for diagnosing or monitoring a disorder that affects the upper or lower respiratory tract, selected from respiratory infection, chronic obstructive pulmonary disease (COPD), asthma, cystic fibrosis and lung cancer, said method comprising performing the method of analyzing the composition of a microbiome as described above using the PCR calibrator system on a pulmonary sample selected from bronchoalveolar lavage, a sputum sample and a lung biopsy, and optionally treating the patient by pharmacological intervention, preferably wherein the pharmacological intervention comprises the systemic, topical or local administration of an antibiotic, anti-inflammatory or antineoplastic agent.

In another aspect, the present invention provides a method for diagnosing or monitoring a microbial infection, said method comprising performing the method of analyzing the composition of a microbiome as described above using the PCR calibrator system on a liquor sample, a pleural sample, a blood sample, a urine sample, an abscess sample, or a tissue sample of an organ, and optionally treating the patient by pharmacological intervention, preferably wherein the pharmacological intervention comprises the systemic, topical or local administration of one or more an antibiotic agents.

In another aspect, the present invention provides a method for diagnosing or monitoring a microbial infection, said method comprising performing the method of analyzing the composition of a microbiome as described above using the PCR calibrator system on a liquor sample, a pleural sample, a blood sample, a urine sample, an abscess sample, or a tissue sample of an organ, and optionally treating the patient by pharmacological intervention, preferably wherein the pharmacological intervention comprises the systemic, topical or local administration of one or more antibiotic agents.

In another aspect, the present invention provides a method for determining the microbial status of a sample, wherein said sample is of environmental, plant, animal or food origin, or a sample of a pharmaceutical or chemical product intended to be devoid of microbes or microbial DNA said method comprising performing the method of analyzing the composition of a microbiome as described above using the PCR calibrator system on a sample from said source, and optionally treating the source from which the sample was obtained, wherein said status is indicative of sterility of said sample, quality of the environment, microbial safety of food, or the health of plant or animal, preferably wherein the treatment comprises the reduction of microbial growth in said sample source.

In another aspect, the present invention provides a method of typing the intestinal flora of a subject for having a diverticulitis signature, comprising analyzing the composition of the population of microorganisms in said intestinal flora based on taxonomic variation in the DNA sequence of the microbial 16S-23S rRNA internal transcribed spacer (ITS) regions in the genomic DNA of said microorganisms, wherein the sequences of conserved DNA regions comprised in the 16S and 23S rRNA sequences flanking said ITS region in the microbial genome comprise primer binding sites for amplification of said ITS regions, said analysis comprising the steps of:

a) providing a sample of genomic DNA from the population of microorganisms constituting the intestinal flora of a subject;

b) performing a PCR amplification reaction on said sample of genomic DNA using at least one set of PCR amplification primers directed to said flanking conserved DNA regions to thereby amplify and provide amplification products of said ITS regions comprised in said genomic DNA sample;

c) analyzing said amplification products to thereby provide a test signature of the composition of the population of microorganisms in said intestinal flora;

d) comparing said test signature with a reference signature of a healthy subject and/or a subject suffering from diverticulitis and classifying the test signature as a signature of a healthy subject or as a signature of a subject suffering from diverticulitis.

In a preferred embodiment of a method of typing the intestinal flora of a subject for having a diverticulitis signature as described above, said step b) of performing a PCR amplification reaction on said sample of genomic DNA using at least one set of PCR amplification primers directed to said flanking conserved DNA regions comprises the use of a set of PCR amplification primers for amplifying the 16S-23S rRNA internal transcribed spacer (ITS) regions in the genomic DNA of the phyla Firmicutes and Bacteroidetes and a set of PCR amplification primers for amplifying the 16S-23S rRNA internal transcribed spacer (ITS) regions in the genomic DNA of the phylum Proteobacteria.

In In another preferred embodiment of a method of typing the intestinal flora of a subject for having a diverticulitis signature as described above, said set of PCR amplification primers for amplifying the 16S-23S rRNA internal transcribed spacer (ITS) regions in the genomic DNA of the phyla Firmicutes and Bacteroidetes comprises the use of:

a) the forward primer 5'-CTGGAT-CACCTCCTTTCTAWG-3' (SEQ ID NO: 1) comprising a first fluorescent label, b) the forward primer 5'-CTG-GAACACCTCCTTTCTGGA-3' (SEQ ID NO: 2) comprising a second fluorescent label;

c) and three unlabeled reverse primers 5'-AGGCATC-CACCGTGCGCCCT-3' (SEQ ID NO: 3); 5'-AGGCATT-CACCRTGCGCCCT-3' (SEQ ID NO: 4); and 5'-AGG-CATCCRCCATGCGCCCT-3' (SEQ ID NO: 5).

In yet another preferred embodiment of a method of typing the intestinal flora of a subject for having a diverticulitis signature as described above, said set of PCR amplification primers for amplifying the 16S-23S rRNA internal transcribed spacer (ITS) regions in the genomic DNA of the phylum Proteobacteria comprises the use of:

a) the forward primer 5'-CCGCCCGTCACACCATGG-3' (SEQ ID NO: 6)

b) at least one of the reverse primers selected from the group consisting of 5'-AATCTCGGTTGATTTCTTTTCCT-3' (SEQ ID NO: 7), 5'-AATCTCGGTTGATTTCTTCTCCT-3' (SEQ ID NO: 8), 5'-AATCTCTTTTGAT-TTCTTTTCCTCG-3' (SEQ ID NO: 9), 5'-AATCTCATTTGATGTCTTTTCCTCG-3' (SEQ ID NO: 10), 5'-AATCTCTTTTGATTTCTTTTCCTTCG-3' (SEQ ID NO: 11), 5'-AATCTCTCTTGATTTCTTTTCCTTCG-3' (SEQ ID NO: 12), 5'-AATCTCAATTGAT-TTCTTTTCCTAAGG-3' (SEQ ID NO: 13), wherein at least one of said primers comprises a fluorescent label, preferably a fluorescent label that is different from other taxon-specific fluorescent labels in the reaction mixture.

In another preferred embodiment of a method of typing the intestinal flora of a subject for having a diverticulitis signature as described above, said method comprises the use of a PCR calibrator system as defined herein above, using the method of analyzing the composition of a microbiome as described above using the PCR calibrator system.

In another preferred embodiment of a method of typing the intestinal flora of a subject for having a diverticulitis signature as described above, the signature of a subject suffering from diverticulitis is characterized in having an increased diversity in the phylum Proteobacteria as calculated using the Shannon index.

In another preferred embodiment of a method of typing the intestinal flora of a subject for having a diverticulitis signature as described above, the increased diversity in the phylum Proteobacteria is constituted by an increased diversity in the family Enterobacteriaceae.

In another preferred embodiment of a method of typing the intestinal flora of a subject for having a diverticulitis signature as described above, an increased diversity in the phylum Proteobacteria is indicated by an increase in the presence of at least one of the species selected from the group consisting of *Escherichia coli, Klebsiella pneumoniae, Enterobacter aerogenes, Serratia marcescens, Klebsiella variicola, Providencia stuartii, Desulfovibrio* spp., *Stenotrophomonas* spp. (*Xanthomonas* spp.), *Pseudomonas aeruginosa, Burkholderia* spp. and Aggregatibacter *actinomycetemcomitans*.

In another preferred embodiment of a method of typing the intestinal flora of a subject for having a diverticulitis signature as described above, said sample of intestinal flora is a sample obtained from the small or large intestine, preferably colon or rectum, more preferably obtained in the form of a fecal sample or rectal swab or in the form of a biopsy specimen of gastrointestinal mucosa.

DESCRIPTION OF THE DRAWINGS

FIG. 1 shows PCR calibrator profiles and potential interpretations for correction of nonlinear differences in amplification efficiency of fragments of different length as exemplified in Example 1.

FIG. 2 shows the principle of up-scaling of a partially inhibited sample using the PCR calibrator system as exemplified in Example 1.

FIG. 3 shows the use of the PCR calibrator system in error checking of automated length marker detection as exemplified in Example 1.

FIG. 9 shows schematically how two subject groups were sampled in Example 3. Group A consisted of 38 subjects who underwent an elective colonoscopy. This group collected feces at home 2 to 5 days prior to the procedure. Rectal swabs and biopsies were taken during the procedure. Two swabs were stored for 2 hours at room temperature and at −20° C. afterwards, one swab was immediately snap frozen. The mucosal biopsy was washed in PBS and snap frozen. Group B consisted of 10 patients with inflammatory bowel disease. This group collected feces and one rectal swab at home. Feces was stored in a sterile container and the rectal swab in RTF buffer, both at −20° C. A second rectal swab was obtained on the day of presentation at the outpatient clinic and stored in the same fashion as the first swab.

FIG. 44 relates to the diagnosis, monitoring and prediction of Necrotising Enterocolitis (NEC) in prematurely born children. FIG. 44A shows the IS-Pro profile (individual profile view) of fecal samples of Necrotising Enterocolitis (NEC) patients and control subjects as described in Example 18. FIG. 44C shows ROC curves summarizing the predictive power of a PLS-DA model for clinical status per phylum and for all phyla combined. From this figure it follows that differences between patients and control subjects in the phylum Proteobacteria are exploited to diagnose, monitor and predict Necrotising Enterocolitis (NEC) in prematurely born children.

FIG. 45 relates to the diagnosis, monitoring and, especially, prediction of the occurrence of sepsis in neonates based on analysis of the intestinal microbiota (feces). FIG. 45B shows boxplot comparisons of within-sample diversity as calculated by Shannon index (per phylum) for sepsis patients and control subjects for the experiment as described in Example 19.

DETAILED DESCRIPTION OF THE INVENTION

Definitions

Figure 1A:
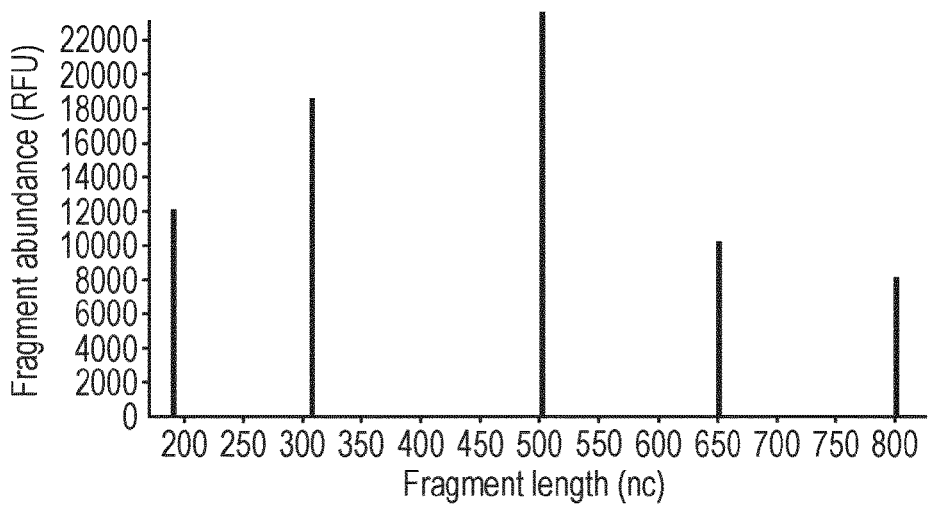
FIG. 1A: Typical digital profile of the five PCR calibrator fragments after amplification and length sorting by capillary gel electrophoresis.

The term "microbiome", as used herein, refers to a population of microorganisms from a particular environment, including the environment of the body or a part of the body, as well as the population of microorganisms inhabiting soils, plants and waterbodies. The term is interchangeably used to address the population of microorganisms itself (sometimes referred to as the microbiota), as well as the collective genomes of the microorganisms that reside in the particular environment.

The term "environment", as used herein, refers to all surrounding circumstances, conditions, or influences to which a population of microorganisms is exposed. The term is intended to include reference to any a subject of study, hence, including environments in a subject, such as a human subject, but particularly refers to environments such as soil, a waterbody or a plant.

The term "disease or condition in a subject" may include reference to disease or condition in an environment, by preferably refers to disease or condition in a human or animal subject.

The terms "IS-pro" and "IS-profiling", as used interchangeably herein, are used in the context of a specific method of analyzing the composition of a microbiome based on taxonomic variation in the DNA sequence of the microbial 16S-23S rRNA internal transcribed spacer (ITS) regions in the genomic DNA of the microorganisms in said microbiome. The technique is described in detail in Budding et al. 2010 (FASEB J., 24(11):4556-64), which publication is incorporated in its entirety by reference herein, and is also described in detail herein below.

The term "intergenic spacer region", as used herein, refers to a genomic sequence located between two genes.

The terms "16S-23S rRNA internal transcribed spacer (ITS) region" and "16S-23S intergenic spacer (IS) region", as used herein, refer to a segment of non-functional DNA situated between structural ribosomal RNA (rRNA) genes on a common precursor transcript. In literature, this region is also synonymously called 16S-23S rDNA intergenic spacer region (IS region) (Budding et al., 2010, cited above), 16S-23S rRNA intergenic spacer region (Mora et al. 2003. Microbiology 149: 807-813), 16S-23S rRNA gene internal transcribed spacer (ITS) region (Wang et al 2008. J Clin Microbiol. 46(11): 3555-3563), 16s/23s ribosomal spacer region (Barry, T. et al. 1991. PCR Methods Appl. 1:51-56. In the genome of *Escherichia coli* CFT073 (Genbank accession AE014075.1), the ITS region separating the 16S and 23S rRNA genes in one of the rrn operons is indicated by nucleotides numbered 236727-237160, comprising 433 bases. In many microbial species the 16S-23S ITS region contains coding sequences for tRNA genes. Multiple rRNA operons (rrn) may be present within the genome of a microorganism, sometimes as many as 15, which often display intragenomic heterogeneity in ITS type. The spacer regions between the 16S and 23S genes in the prokaryotic rRNA genetic loci show a significant level of length and sequence polymorphism across both genus and species lines. Pairs of priming sequences can be selected for the amplification of these polymorphic regions from highly conserved sequences in the 16S and 23S genes occurring adjacent to these polymorphic regions.

The term "16S rRNA gene", as used herein, refers to a DNA sequence or sequences encoding the 16S rRNA molecule.

The term "23S rRNA gene", as used herein, refers to a DNA sequence or sequences encoding the 23S rRNA molecule.

The term "polymorphic DNA target region", as used herein, refers to a DNA region varying in length and/or sequence in different taxonomic groups of microorganisms and that serves as a target for PCR amplification.

The term "conserved region", as used herein, refers to a segment of nucleotide sequence of a gene or amino acid sequence of a protein that is significantly similar between various different nucleotide sequences of a gene. This term is interchangeably used with the term "conserved sequence". The term "conserved DNA region", in particular refers to a DNA region that (i) comprises multiple nucleotides (preferably between 15-30 nucleotides), (ii) flanks a polymorphic DNA target region, (iii) shares a high degree of homology among genomes of microorganisms in a taxonomic group of microorganisms, thus differentiating between organisms of certain taxonomic groups, and (iv) is able to serve as a primer binding site for PCR amplification primers. In the context of this invention, a DNA region is defined as conserved when said sequence exhibits a sequence homology or nucleotide sequence similarity of at least 60%, preferably 70%, more preferably 80%, even more preferably 90% between different microorganisms belonging to a single taxonomic group, wherein said sequence similarity is calculated over the entire length of the nucleic acid sequence(s).

The term "sample", as used herein, refers to any sample suitable for analyzing or typing according to the methods of the present invention. A sample may be collected from an organism (e.g., human or other mammal, plant) or environmental site (e.g. mineral, soil, rock, water). The biological sample can be in any form, including without limitation a solid material such as a tissue, cells, a cell pellet, a cell extract, or a biopsy, or a biological fluid such as urine, blood, stool, saliva, amniotic fluid, exudate from a region of infection or inflammation, or a mouth wash containing buccal cells, urine, cerebrospinal fluid and synovial fluid and organs.

The term "amplification", as used herein, includes methods for copying a target nucleic acid, thereby increasing the number of copies of a selected nucleic acid sequence. Amplification may be exponential or linear. A target nucleic acid may be either DNA or RNA. The sequences amplified in this manner form an "amplification product", "amplimer" or "amplicon", which terms are used interchangeably herein. While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, Saiki, "Amplification of Genomic DNA" in PCR Protocols, Innis et al., Eds., Academic Press, San Diego, Calif. 1990, pp. 13-20; Wharam et al., Nucleic Acids Res., 29(11):E54-E54, 2001; Hafner et al., Biotechniques, 30(4):852-56, 858, 860, 2001: Zhong et al., Biotechniques, 30(4):852-6, 858, 860, 2001.

The terms "amplification product", and "amplicon", as used interchangeably herein, refer to a nucleic acid fragment that is the product of a nucleic acid amplification or replication event, such as for instance formed in the polymerase chain reaction (PCR).

The term "template", as used herein, refers to the nucleic acid from which the target sequence is amplified in a nucleic acid amplification reaction. The term "amplifiable template", as used herein, refers to a template that, when amplified, results in a single amplicon. Amplifiable templates comprise primer binding sites for hybridization of amplification primers.

The term "primer" as used herein refers to a single stranded nucleotide sequence which is capable of acting as a as used herein refers to a single-stranded oligonucleotide capable of acting as a point of initiation of template-directed DNA synthesis under appropriate conditions (e.g., buffer, salt, temperature, and pH) in the presence of nucleotides and an agent for nucleic acid polymerization (e.g., a DNA-dependent or RNA-dependent polymerase). Generally, the sequence of the primer is substantially complementary to a nucleic acid strand to be copied, or at least comprises a region of complementarity sufficient for annealing to occur and extension in the 5 ' to 3' direction therefrom. The primer may be a DNA primer, RNA primer, or a chimeric DNA/RNA primer. Primers are preferably synthetic oligonucleotide sequences of about 12-100 nucleotides in length; preferably, about 30-60 nucleotides in length. The term "primer" may refer to more than one primer, particularly in the case where there is some ambiguity in the information regarding one or both ends of the target region to be amplified. If a "conserved" region shows significant levels of polymorphism in a population, mixtures of primers can be prepared that will amplify such sequences, or the primers can be designed to amplify even mismatched sequences. A primer can be labeled, if desired, by incorporating a label detectable by spectroscopic, photochemical, biochemical, immunochemical, or chemical means. For example, useful labels include radioactive labels, fluorescent labels, electron-dense reagents, enzymes (as commonly used in ELISAs), biotin, or haptens and proteins for which antisera or monoclonal antibodies are available. Preferred labels for use in this invention comprise fluorescent labels, preferably selected from FAM, TET, HEX, Cy5, Cy5.5, Cy3, Cy3.5, Cy7, Alexa® dyes Tamra®, ROX, JOE, FITC, and TRITC.

The term "primer set", as used herein, refers to the primer pair consisting of at least one forward primer and at least one reverse primer used in a PCR amplification reaction.

The term "primer binding site", as used herein, refers to a specific region of the DNA fragment or segment that, as a result of its DNA sequence, is receptive of binding a PCR amplification primer having a complementary DNA sequence through DNA hybridization. A primer binding site preferably ranges in size of between 15-30 nucleotides. The primer binding site comprised in the upstream adapter DNA sequence preferably differs in DNA sequence from the primer binding site comprised in the downstream adapter DNA sequence. Primer binding sites in the adapter DNA sequence preferably differ in DNA sequence from the primer binding site comprised in the conserved regions of the 16S and 23S rRNA genes used for amplifying the ITS regions from the genomic DNA of the microbiome investigated The term "co-amplified", as used herein, refers to the simultaneous amplification of different nucleic acid fragments in a single amplification reaction.

The term "target nucleic acid" as used herein refers to the nucleic acid that intended to be amplified in a nucleic acid amplification reaction, and in particular to the part of the template nucleic acid positioned between and including the primer binding sites.

The term "amplification efficiency", as used herein, refers to the amount of amplification product produced in an amplification reaction from a given initial number of target sequences in a given number of amplification cycles. Thus, the amplification efficiencies of two reaction which differ only in the length of the target sequences are compared by quantitatively measuring the amount of product formed in each reaction. The amplification efficiency is a measure of the efficacy of amplicon formation in a PCR reaction and can be calculated by determining the output amplicon copy number (or product) over the input template copy number. Determination of PCR amplification efficiency is well known to one of skill in the art and is for instance explained in detail in such publications as Lalam, 2006, J Theor Biol. 242(4):947-53.

The term "standard curve", as used herein, refers to an equation or function that describes the measured relationship between the length of a DNA template and the amount of amplification product produced from this template in a PCR amplification reaction in a given number of amplification cycles.

The term "PCR calibrator", as used herein, refers to an amplifiable DNA fragment or segment serving, inter alia, as a reference template for determining the length-dependent amplification efficiency in PCR amplification reactions as described herein, in particular for determining the efficiency of the amplification reaction in amplifying sample templates of different length. At least one PCR calibrator is included in each PCR reaction. PCR calibrators consisting of rrn operons or parts thereof of existing microorganisms, wherein the intergenic region between the 16S and 23S rRNA genes are flanked by there native 16S and 23S rRNA gene sequences or at least by conserved regions thereof, are not part of this invention.

The term "flanked", as used herein, refers to having a defined DNA sequence (i.e. an adapter DNA sequence) contiguous with both ends of a given DNA sequence or segment (i.e. an ITS region DNA sequence).

The terms "upstream" and "downstream", as used herein, refer to a position of a genetic element on a polynucleotide sequence in relation to another genetic element. A first genetic element is upstream to a second genetic element when located in the 5' direction of the second element. A first genetic element is downstream to a second genetic element when located in the 3' direction of the second element.

The term "plasmid", as used herein, refers to a circular, double-stranded unit of DNA that replicates within a cell independently of the chromosomal DNA.

The term "replicon", as used herein, refers to a DNA molecule or RNA molecule, or a region of DNA or RNA, that replicates from a single origin of replication. Preferably, the replicon is a plasmid.

The term "microorganism", as used herein, refers to any unicellular microorganism including bacteria, archaea, protists, fungi, virus, and algae, preferably bacteria. The term "microbial" indicates pertaining to, or characteristic of a microorganism.

The term "intestinal flora", as used herein, refers to the population of microorganisms inhabiting the gastrointestinal tract.

The term "genomic DNA" as used herein refers to any DNA comprising a sequence that is normally present in the genome of a prokaryotic or eukaryotic cell or a virus. The term refers in particular to the full complement of DNA contained in the genome of a cell or organism comprising the full collective gene set of a cell. In obtaining a sample of genomic DNA from a microbiome for quantitative population analysis, preferably the genomic DNA of essentially all cells in the population is isolated and such a genomic DNA sample is also referred to as total DNA. Total genomic DNA extraction procedures from divers microbiomes are known in the art and commercial genomic DNA isolation kits for this purpose can be obtained from various manufacturers.

The term "population", as used herein, refers to a plurality of individual organisms, in the context of this invention, the term refers in particular to a collection of organisms of divers taxonomic affiliation, in particular bacteria.

The term "diversity", as used herein, refers to the extent to which different taxonomic groups of microorganisms are present in a population of microorganism. In order to quantify and compare microbial taxonomic diversity, i.e. "within-sample diversity", diversity calculation using the Shannon index is recommended (Haegeman et al. 2013. ISME J 2013; 7:1092-101). Diversity analysis, including "between sample diversity" analysis may be performed using R software vegan package (Oksanen, J. et al. vegan: Community Ecology Package. R package version 2.0-7 (2013)). Sample diversity may be assessed for instance at the level of an individual phylum, such as on the level of the phylum Firmicutes, Bacteroidetes, or Proteobacteria. Alternatively, the sample diversity may be assessed overall. High diversity is equivalent with a high taxonomic variation, meaning that many different bacterial taxons (e.g. different bacterial species) are represented in the population, while a low diversity is equivalent with a low taxonomic variation, meaning that a population is characterized by relatively few bacterial taxons. In intestinal (fecal) flora, a Shannon index above 3 for the overall microbiota is considered to represent a high bacterial population diversity.

The term "taxonomic variation" refers to the diversity in groups of microorganisms when grouped into species, genera, families, orders, classes and/or phyla in accordance with a biological classification scheme.

The term "typing", as used herein, refers to classifying a test signature as either corresponding to the signature of a first condition or corresponding to the signature of a second condition in a classification scheme, such as a scheme classifying healthy and diseased subjects.

The terms "subject", as used herein, includes reference to a human and non-human animal, preferably a human adult in the age of 18 years or older. The term "healthy subject" refers to a control subject not suffering from a disease of interest, although such a control subject may suffer from a different or related disease. The term "patient" refers to a "subject" who is, or is suspected to be, afflicted with the disease of interest. In the context of Necrotising Enterocolitis (NEC), the subject or patient is preferably a prematurely born subject, more preferably a prematurely born subject having an age between 0 and 18 years, most preferably a prematurely born at a gestational age from 24 to 37 weeks. In the context of sepsis, the subject or patient is preferably a neonate.

The term "neonate", as used herein, refers to a newborn infant less than four weeks old, the term including prematurely born infants.

The term "prematurely born subject", as used herein, refers to a subject that is born at less than 37 weeks gestational age.

The phrase "method for diagnosing or monitoring", in the context of a method for diagnosing or monitoring Necrotising Enterocolitis (NEC) and/or sepsis in a subject, comprises predicting whether Necrotising Enterocolitis (NEC) and/or sepsis will develop in said subject.

The term "signature", as used herein, refers to a profile of amplified nucleic acid fragments representing the diversity in 16S-23S ITS regions from microorgansisms in a genomic DNA sample from a sample population, wherein different ITS regions represent different taxonomic groups of microorganisms, preferably said profile representing the prevalence of the various taxonomic groups of microorganisms in the sample population.

The terms "desirable signature" and "undesirable signature", as used herein, refer in general to a beneficial signature and an unfavorable signature, these signatures representing an elected biological profile such as (i) non-diseased versus diseased, (ii) sterile versus non-sterile, (iii) non-infected vs. infected, (iv) advantageous for plant growth due to the presence of a specific micro-organism vs. disadvantageous due to the absence of said specific micro-organism.

The term "reference signature", as used herein, refers to a signature of a control subject.

The term "phylum", as used herein, refers to a taxonomic rank below kingdom and above class.

I. PCR Calibrator System

Polymerase Chain Reaction (PCR) is a process in which DNA is amplified. Inhibition of PCR can result in false negative results, and can seriously hamper quantification of taxonomic groups in a microbiome. Inhibition can be assessed by using an internal control DNA fragment and primers specific for that fragment. If the internal control DNA fragment is not amplified, it can be deduced that the PCR reaction was inhibited. For microbiome analysis it is not known how PCR inhibition affects the outcome of the analysis, in particular in view of the fact that ITS regions are polymorphic in length. Proper quantitation of initial copy number of all amplicons in samples comprising multiple amplicons (originating from multiple bacteria) requires information on potential length-specific inhibition and is of great significance to e.g. testing for contamination in commercial probiotic mixtures, or for determining the abundance of Streptococcus pneumonia as having a normal levels or the level of infection in a throat microbiome.

Another problem in microbiome analysis, in particular when the IS-pro method is performed using two or more separate PCR reactions (e.g. one for the phyla Firmicutes/Bacteroidetes and one for the phylum Proteobacteria), is that the information generated by these separate PCR reactions needs to be properly merged in order to obtain quantitative results that can be compared or merged. It would be desirous to have an indication of how separate results should be transformed to render them comparable.

The length of DNA fragments generated in an IS-pro reaction cannot directly be inferred from their transition time in capillary electrophoresis. Therefore fragment length markers are routinely incorporated in the PCR reaction prior to electrophoretic analysis of the amplification products. By comparing transition times of such marker fragments to the transition times of unknown microbiome fragments, the length of the unknown fragments can be inferred. This requires correct identification of the marker fragments, which process is automatically performed in the custom IS-pro pre-processing software, but this system would benefit from a supplemental check for correct marker identification.

The presently proposed PCR calibrator system now provides a solution to all the above aspects of sample analysis using the IS-pro method, including (i) reaction inhibition, (ii) length-dependent amplification, (iii) calibration of electrophoresis length markers, and (iv) scaling of profiles of separate IS-pro PCR reactions. This greatly improves reliability and reproducibility of the results of the IS-pro method, rendering the method uniquely suitable for, inter alia, research, clinical diagnostics and quality assurance.

The PCR calibrator system as disclosed herein comprises a set of PCR amplification primers and a set of at least two PCR calibrators.

Preferably the set of amplification primers consists of a single forward primer and a single reverse primer for amplifying all PCR calibrators in the system. At least one of the primers in the set of calibrator primers, preferably the forward primer, comprises a label, preferably a fluorescent label. Since one or more of the IS-pro primers (i.e. the taxonomic group-specific primers used to amplify the sample ITS regions and giving rise to labelled IS-pro amplimers) are in preferred embodiments also fluorescently labelled, it is essential that the fluorescent label in the set of calibrator primers differs from the label(s) of the IS-pro primers.

The PCR calibrator primers are preferably designed such that there is no interference with the actual IS-pro analysis. Hence, random amplification of non-target DNA by non-specific binding of the PCR calibrator primers in a reaction mixture comprising genomic DNA of a complex microbial population should essentially be avoided. An effective PCR reaction that produces essentially no non-specific amplicons requires stable and specific binding between the 3' ends of the primer and its DNA template; in contrast, the 5' end is not critical for PCR. The uniqueness of the 3'-end subsequence of a primer mainly determines the specificity of the primer, although the binding stability is related to the entire primer sequence. The Tm value and Gibbs free energy (ΔG) of the binding between calibrator primer and its target in the adapter sequence are preferably optimized for binding stability in order to minimize non-specific amplicon production in the IS-pro reaction. Moreover, the Tm value of the calibrator primer is preferably compatible with the Tm value of the IS-pro primers. The present inventors have found that using reverse sequences of the conserved regions serving as primer binding sites for the IS-pro primers provide for very suitable primer binding sites for the calibrator primers.

These binding sites are facilitated by means of adapter sequences flanking the PCR calibrator fragments. In a highly preferred embodiment, the set of calibrator primers in the calibrator system of this invention comprises the following primers:

```
                                          (SEQ ID NO: 14)
    MPICf5'- GACCTAGTGGAGGAAAGATAC -3'

(SEQ ID NO: 15)
    MPICr5'- TCCGTAGGTGGCACGCGGGA -3'
``` wherein MPICf represents the PCR calibrator system forward primer, and

MPICr represents the PCR calibrator system reverse primer.

Primer binding sites for the calibrator primers are provided in the form of flanking adapter DNA sequences located upstream and downstream of the PCR calibrator fragments.

The PCR calibrator system as disclosed herein further comprises a set of at least two PCR calibrators, wherein each PCR calibrator represents a semi-artificial fragment of DNA that serves as an amplification template for the calibrator primers. The PCR calibrators comprise a spacer region DNA sequence (preferably representing a microbial 16S-23S rRNA ITS region) of a given length wherein the spacer region DNA sequence comprised in each of said PCR calibrators in said set of at least two PCR calibrators is of a different length. The term "spacer region DNA sequence of a given length" in the context of the PCR calibrators refers to a DNA sequence essentially representing an amplifiable DNA sequence flanked by adaptor sequences that is co-amplified together with the DNA sequence of a 16S-23S rRNA ITS region of a microorganism. The purpose of the spacer region in the calibrator is to provide an amplifiable sequence that is amplified with the same characteristics as the sample amplification template in an IS-pro reaction (i.e., the ITS region). Hence, it is preferred that the sequence of PCR calibrator of a given length resembles the sample amplification template in an IS-pro reaction as closely as possible. It will therefore be understood that in order to prepare such a calibrator of different length, one may start from any existing DNA sequence of a microbial 16S-23S rRNA ITS region of a given length and reduce or increase the length thereof, for instance by shortening that region using restriction enzymes or other molecular biological techniques, or by ligating that region to other ITS regions or parts thereof. Alternatively, an artificial or semi-artificial DNA sequence can be used as the spacer region sequence in the PCR calibrators of this invention, the exact sequence of which is not essential. In preferred embodiments, the PCR calibrator comprises as the spacer region at least a part of a 16S-23S rRNA ITS region of a microorganism. The term "at least a part of a 16S-23S rRNA ITS region of a microorganism" as used herein refers to a DNA sequence of at least 20, preferably at least 30, 40, 50, 60, 70, 100, 150, or 250 consecutive nucleotides having at least 95%, preferably at least 99%, more preferably 100% sequence similarity with (part of) the DNA sequence of a 16S-23S rRNA ITS region of a microorganism selected from the phyla Firmicutes, *Fusobacterium*, Deferribacteres, Spirochaetes, Cyanobacteria, Acidobacteria, Nitrospina, Nitrospirae, Caldithrix, Haloanaerobiales, Verrrucomicrobia, Chlamydiae, Planctomycetes, Gemmimonas, Fibrobacteres, Chlorobi, Bacteroidetes, Proteobacteria, Thermotogae, Corprothermobacter, Synergites, Thermodesulfobacteria, Desulfurobacterium, Aquificae, *Deinococcus-Thermus*, Chloroflexi, Tenericutes and Actinobacteria, preferably from the phyla Bacteroidetes, Firmicutes, Actinobacteria, Proteobacteria, Fusobacteria and Verrrucomicrobia.

In a preferred embodiment, the PCR calibrator system consists of a set of at least 3, 4, more preferably about 5, 6, 7, 8, 9 or 10 PCR calibrators of different length. The various PCR calibrators in the PCR calibrator system preferably all have different lengths, which lengths are more or less equally distributed over the expected length spectrum of the IS-pro amplimers. Preferred lengths for the PCR calibrators in a system of this invention result in calibrator amplicons between 50 and 1200 base pairs, preferably, a 5-calibrator set can consist of calibrators of around 150, 300, 450, 650 and 850 base pairs.

The PCR calibrator system may serve one of multiple purposes as explained above. Although the PCR calibrator system is preferably added to each separate IS-pro PCR reaction that is performed in the course of a single composition analysis, the PCR calibrator system for the purpose of providing a standard curve as defined herein can be used in a parallel PCR reaction, that is performed separately from the taxon-specific IS-pro PCR reaction(s). It is preferred in such cases that the parallel reaction is performed in the presence of a sample of genomic DNA of the microbiome that is studied, because this provides for conditions that allow for the occurrence of the same PCR inhibiting effect for which the IS-pro PCR reaction is to be corrected. If such a parallel reaction is used, it is also essential that at least one PCR calibrator is present in the IS-pro PCR reaction(s) so as to provide an internal control, the amplification efficiency of which can be compared with the amplification efficiency of the PCR calibrator having a corresponding length in the parallel reaction for the standard curve. In this case, both length-dependent correction of amplification efficiency and scaling of amplitude of the amplification (the overall efficiency) can be achieved.

In preferred embodiments, the PCR calibrator system is incorporated in the IS-pro reaction and the PCR calibrators are co-amplified with the sample ITS regions. When amplified in the IS-pro reaction (or in a parallel reaction as the case may be), the PCR calibrator system results in a specific peak profile (see FIG. 1A). This peak profile can be used to perform one or more corrective calculations on the amplification results of the IS-pro reaction.

In a preferred embodiment, each of the at least two PCR calibrators in the set is present in exact equal amounts, although each PCR calibrator may also be present in known amounts relative to any other PCR calibrator in said set. This eases the quantitative analysis of the PCR reaction results. In order to prepare a mixture of PCR calibrators present in equal amounts, the present inventors have found that a copy of each of the calibrator sequences, each including its flanking adaptor sequences, can be inserted in a plasmid, and the plasmid can be cloned and replicated in a suitable host. The plasmid DNA can then be isolated and cut by restriction enzymes having restriction sites located between each PCR calibrator, thereby providing a preparation of PCR calibrators having different length and present in equal amounts.

A set of at least two PCR calibrators as described herein above, wherein said set is comprised in a single replicon or single amplifiable template, preferably a DNA plasmid, is an aspect of this invention.

Inhibition of the PCR Reaction

An advantage of the proposed calibrator system is that it can provide information on inhibition. Inhibition of the PCR reaction can be identified when the PCR calibrator system does not yield a profile. Moreover, if the profile is lower than the PCR calibrator profile that is found in a parallel reaction or in a blank sample (with no target DNA for the regular PCR reaction), it can be assumed that there is inhibition to a certain extent which can be corrected for. This correction may be done by up-scaling the PCR calibrator profile to the same level (peak heights) as found in the blank sample. The same up-scaling factor can then be applied to all other peaks present in the profile (FIG. 2). Finally, a cut-off can be defined for the level of inhibition, based upon which a sample can be accepted or refused for further analysis by an (automated) quality system. Alternatively, if a single internal control PCR calibrator as defined herein is used on concert with a parallel PCR calibrator system for generating the standard curve, an up-scaling factor may also be calculated based on the internal control PCR calibrator that can then be applied to all peaks of the IS-pro profile, while the parallel PCR calibrator system consisting of at least two PCR calibrators of different length amplified in a genomic DNA sample having the same potential inhibiting effect could provide information on the amplification efficiency of the various peaks present in the profile that represent microbial ITS regions of different length.

Amplification Efficiency of Small Vs Large Fragments

Another advantage of the proposed calibrator system is that it can be used to identify differences in amplification efficiency between short and long fragments of DNA. Because all DNA fragments in the PCR calibrator system are present in exactly the same amount (or in defined amounts relative to each other, depending on the embodiment chosen), the peaks that result from fragment analysis after PCR should all be equal in height (or have defined heights relative to each other). However, as shown in FIG. 1A, this may not be the case in practice. The differences in peak heights are caused by dissimilar amplification efficiencies. As can be seen in FIG. 1A, this effect is generally not linear (a straight line connecting the tops of all peaks cannot be drawn). In case that the PCR calibrator system includes more than two fragments (as is the case in the embodiment of FIG. 1), the overall (nonlinear) function of amplification efficiency over fragment length can be estimated. This can be done by means of a multi-linear model, in which peak tops are connected by means of straight lines (FIG. 1B), or by a more sophisticated nonlinear model (FIG. 1C). Finally, the estimated amplification efficiency function can be used to apply a corrective factor to all peaks present in a profile (FIG. 1D). Note: This whole procedure can be combined with a corrective up-scaling factor when samples are partially inhibited as mentioned above.

Error Checking the Pre-Processing Procedure

Figure 3A:
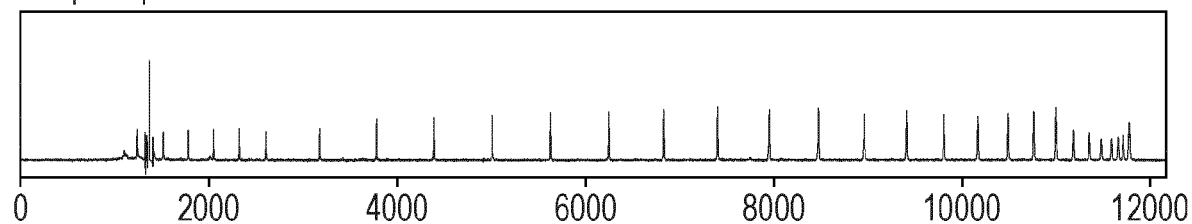
FIG. 3A: Raw capillary gel electrophoresis data for the length marker channel.

Another advantage of the proposed calibrator system is that it can be used to verify correct fragment length determination in the capillary electrophoresis software. To infer fragment lengths from their transition time in capillary gel electrophoresis, a set of fragments of known length is added to the process (so-called length markers). These fragments can be readily seen in the raw capillary gel electrophoresis data (FIG. 3A). Such data are subsequently analyzed by custom pre-processing software. This software tool identifies every fragment belonging to the length marker and assigns a length value to it. It is important to supervise this process independently, as it may have an impact on all subsequent analyses. For this purpose, the presently proposed PCR calibrator system can be used. The PCR calibrator system, the length marker and the IS-pro fragments are in a preferred embodiment all run concurrently in the same capillary in the capillary gel electrophoresis machine. Information of fragment lengths of the length marker can in such instances be used to infer lengths of the other fragments. The PCR calibrator system, internal control and IS-pro fragments, in a preferred embodiment, all have different fluorescent labels, allowing their separate analysis. To evaluate if any errors have occurred in the identification of the length marker peaks during the pre-processing step, the position of the peaks of the PCR calibrator system as detected in the same capillary electrophoresis run can be used. After identification of length marker peaks, all other peaks (from PCR calibrator system and IS-pro) can be assigned length values. As the PCR calibrator peaks have known lengths, they can be used to control the identification of the length marker peaks. To do this, the lengths of the PCR calibrator peaks as assigned by the software tool are compared to their real (known) lengths. If these values correspond, it may be safely assumed that the length marker peaks have been identified correctly.

Scaling of Profiles from Separate PCR Reactions

As stated above, the IS-pro method may, in preferred embodiments, consist of two or more separate PCR reactions for amplifying different taxonomic groups of microorganisms. For some applications of the IS-pro method it is necessary to combine information from these two or more separate PCRs in a quantitative manner, e.g. when abundances of all taxonomic groups in a complex sample are to be investigated. To do this, a reference signal is needed that is the same in both reactions. For this purpose, the PCR calibrator system can be used. By comparing the height of the PCR calibrator peaks in one PCR reaction with their corresponding height in the other reaction, and knowing the amount of calibrator added to the mixtures, quantitatively comparative results can be obtained by up- or downscaling all peaks in one of the samples in the same fashion as was described for partially inhibited samples herein above. After this correction, peak profiles can be compared on a quantitative level.

The advantages of the PCR calibrator system as disclosed herein will become more apparent from the Examples below.

II. IS Pro Analysis

The present invention provides in another aspect a method of analyzing the composition of a microbiome based on taxonomic variation in the DNA sequence of the microbial 16S-23S rRNA internal transcribed spacer (ITS) regions in the genomic DNA of the microorganisms in said microbiome.

The method is previously described as the IS-pro method in Budding et al. 2010, and an exemplary method is described in great detail in Example 2, below. IS-pro involves bacterial species differentiation by the length of the 16S-23S rDNA interspace region with taxonomic classification by phylum-specific fluorescent labelling of PCR primers.

Amplifying the 16S-23S rRNA intergenic spacer region from microorganisms is well known in the art. In order to achieve this, the sequences of conserved DNA regions comprised in the 16S and 23S rRNA gene sequences flanking the intergenic region in the genomic DNA of the microorganism are used as primer binding sites for amplification of the polymorphic DNA region on which the taxonomic diversity analysis of IS-pro is based.

Prokaryotic microorganisms, including bacteria and archaea, comprise in their genome one or more copies of the rrn operon comprising the genes for the 5S, 16S and 23S ribosomal RNAs. In most prokaryotes the ribosomal genes in the operon are in the order 16S-23S-5S and are co-transcribed in a single polycistronic RNA that is processed to provide the RNA species present in the mature ribosome. The rRNA 16S and 23S genes have acquired paramount relevance for the study of bacterial evolution and phylogeny, and the presence of variable and conserved regions in both genes is well documented (Neefs et al., 1993. Nucleic Acids Research 21(13): 3025-3049; Baker et al. 2003. J. Microbiol. Meth. 55: 41-555; Van de Peer et al., 1996. Nucleic Acids Research 24(17): 3381-3391; Gurtler and Stanisich, 1996. Microbiology 142: 3-16). The spacer between the 16S and 23S genes contains regions with secondary structures and sometimes tRNA genes. The variation found among relatively close taxa is known to be very high for the spacers of the rRNA operons. The extreme divergence in size and sequence of the spacers among different groups of prokaryotes, together with their location between highly conserved rRNA genes, makes them ideally suited as taxonomic markers. The 16S-23S rRNA intergenic spacer region is amplified using primers directed to conserved regions in the ribosomal gene sequences. More preferably, the conserved DNA regions are those located nearest to the 3'-end of the 16S rRNA gene and nearest to the 5'-end of the 23S rRNA gene.

Amplification of ribosomal sequences is described in detail in Devereux and Wilkinson 2004 (Molecular Microbial Ecology Manual, Second Edition 3.01: 509-522, 2004). The pivotal point for the purpose of microbiome analysis using phylum-specific probes is the primer design. Primers can be designed that selectively amplify rRNA genes of phylogenetically defined groups. Selection of primers can often be guided by comparison of sequences in a database. Many selective rRNA gene primers have been described in the literature. PRIMROSE (Ashelford et al. 2002. Nucl Acids Res 30: 3481-3489) is a program that uses sequences from the Ribosomal Database Project to identify and determine the phylogenetic range of oligonucleotides that may be used as rRNA probes or primers. ProbeBase (Loy et al. 2003. Nucl Acids Res. 31, 514-516) is a database of published rRNA probes with information on target site and specificity. The Ribosomal Database Project II (Maidak et al. 2001. Nucl Acids Res 29:173-174) and the ARB package (Ludwig et al. 2004. Nucleic Acids Research 32(4):1363-1371) provide software for in silico evaluation of intended specificities of ribosomal primers, including those for 16S and 23S rRNAs, against known rRNA sequences.

The present inventors have found that the amplification of the phylum of Proteobacteria is very beneficially performed by carrying out a multiplex PCR in order to provide sufficient taxonomic resolution within the proteobacterial phylum. By simultaneously amplifying multiple sequences in a single reaction, a process referred to as multiplex polymerase chain reaction (PCR), deep resolution can be obtained. Although alternative proteobacterial primers may be used in embodiments of aspects of this invention, the following primer set is preferably used in several embodiments as indicated herein:

```
Primers Proteobacteria
Forward:
                                       (SEQ ID NO: 6)
ProtISf    5'- CCGCCCGTCACACCATGG -3'

Reverse:
                                       (SEQ ID NO: 7)
DPISr1     5'- AATCTCGGTTGATTTCTTTTCCT -3'

(SEQ ID NO: 8)
DPISr2     5'- AATCTCGGTTGATTTCTTCTCCT -3'

(SEQ ID NO: 9)
DPISr3     5'- AATCTCTTTTGATTTCTTTTCCTCG -3'

(SEQ ID NO: 10)
DPISr4     5'- AATCTCATTTGATGTCTTTTCCTCG -3'

(SEQ ID NO: 11)
DPISr5     5'- AATCTCTTTTGATTTCTTTTCCTTCG -3'

(SEQ ID NO: 12)
DPISr6     5'- AATCTCTCTTGATTTCTTTTCCTTCG -3'

(SEQ ID NO: 13)
DPISr7     5'- AATCTCAATTGATTTCTTTTCCTAAGG -3'
```

This primer set in any combination of the forward primer together with at least two of the reverse primers, is an aspect of this invention. Hence in one aspect, the present invention provides a set of oligonucleotide primers for amplifying sequences of the 16S-23S intergenic region of the phylum Proteobacteria from a sample of microbial genomic DNA, said set comprising the forward primer indicated herein above as ProtISf in combination with at least 2 reverse primers selected from the group consisting of reverse primers indicated herein above as DPISr1, DPISr2, DPISr3, DPISr4, DPISr5, DPISr6, and DPISr7. In a preferred embodiment, at least one of said primers comprises a detectable label.

Although the present invention is described in the context of the 16S-23S rRNA intergenic spacer, the skilled person will understand that variations to other intergenic spacer regions, including intergenic spacer regions in eukaryotic rRNA operons are within the ambit of this invention. In fact, any microorganism taxonomically distinguishable on the basis of a polymorphic DNA region flanked by conserved DNA regions, homologous sequences of which are present in all microorganisms may be subjected to analysis to using methods of this invention.

Preferred microorganisms in aspects of this invention belong to bacterial phyla selected from the group consisting of Firmicutes, *Fusobacterium*, Deferribacteres, Spirochaetes, Cyanobacteria, Acidobacteria, Nitrospina, Nitrospirae, Caldithrix, Haloanaerobiales, Verrrucomicrobia, Chlamydiae, Planctomycetes, Gemmimonas, Fibrobacteres, Chlorobi, Bacteroidetes, Proteobacteria, Thermotogae, Corprothermobacter, Synergites, Thermodesulfobacteria, Desulfurobacterium, Aquificae, *Deinococcus-Thermus*, Chloroflexi, Tenericutes and Actinobacteria. More preferred phyla targeted in methods of this invention comprise Bacteroidetes, Firmicutes, Actinobacteria, Proteobacteria, Fusobacteria and Verrrucomicrobia. Highly preferred are Bacteroidetes, Firmicutes, Actinobacteria and Proteobacteria. Any microbiome comprising prokaryotes belonging to these phyla constitutes a preferred microbiome in aspects of this invention.

These phyla are known to the person skilled in the art and have been described, inter alia, in Schloss 2004 (Microb. Mol. Biol. Rev. 6 (4): 686-691), or in the Bergey Manual, Second Edition 2004, Release 5.0.

The microbiomes may be present in any environment. Environments according to the present invention include for example environments present in humans, plants, animals, water, food (like dairy products), yeast cultures (e.g. used in industry) or soil. More specifically, environments such as the (gastro)intestinal tract, vaginal tract, skin, lung, sputum, colon, mouth, teeth pockets, ascetic fluid, feces, purulence, abscess, wound fluid, wound, blood, or a cardiovascular system are envisaged.

The sampling of the above environments, for the purpose of obtaining a representative sample for analysis, may be performed using any suitable method available to one of skill in the art. For example, a sputum specimen may be obtained when the population of microorganisms in the lungs is to be analyzed. A sample of intestinal flora can for example be obtained in the form of a fecal sample, a biopsy of the gastrointestinal mucosa, or a rectal swab. The present inventors have found that the use of a rectal swab provides more consistent results than other methods of sampling the intestinal flora using the IS-pro technique. Hence, an aspect of this invention is a method of performing a sampling of the intestinal flora for IS-pro analysis using a rectal swab, preferably without bead beating.

DNA samples for taxonomic composition analysis with diagnostic purpose from any environment may be obtained by using generally known techniques for DNA isolation. The total genomic DNA may be purified from study environments or from sampling devices probed in said environments by using, for instance, a combination of physical and chemical methods. Very suitably commercially available systems for DNA isolation are used, such as the NucliSENS® easyMAG® nucleic acid extraction system (bioMérieux, Marcy l'Etoile, France) or the MagNA Pure® 96 System (Roche Diagnostics GmbH, Mannheim, Germany).

The genomic DNA sample is analyzed by a PCR-based profiling technique referred to herein as IS-pro as described in Budding et al., 2010 (cited above). In IS-pro, distinct 16S-23S ITS DNA sequences of different length amplified from the sample of genomic DNA are separated by capillary gel electrophoresis, providing a profile of distinct peaks each representing a separate 16S-23S ITS DNA sequence having a characteristic length (in number of nucleotides or base pairs). Each peak is considered to represent a single ITS region. Since genomes may comprise multiple rrn operons with different ITS region sequence, not every peak represents a distinct species of microbe. Hence, peaks are designated as operational taxonomic units (OTUs). In order to improve resolution and separate more peaks from the population, phylum-specific ITS regions can be recognized by using phylum-specific fluorescent labeling. Analysis of the profiles results in the identification of dominant OTUs within phyla and enables identification of variation within these phyla. The person skilled in the art will understand that conserved DNA regions of microorganisms in a taxonomic group other than phylum can be labeled using primers containing said label. Suitable labels are described herein above.

It is preferred, but not essential to aspects of this invention that the PCR calibrator system as described herein is used as part of the IS-pro method. Although the PCR calibrator system of this invention is beneficial to the reliability and reproducibility of the method, useful analytical and diagnostic results are obtained in many analytic and diagnostic embodiments described herein without the use of the calibrator system.

Methods of the present invention may be used to type, diagnose, investigate, analyse and monitor such diverse microbiomes as those associated with the gut or gastrointestinal tract, the skin, the urogenital tract, the oral cavity, and the pulmonary system, and diagnose, monitor or predict disease. The methods may be used for diagnostic purpose such as for diagnosing, monitoring or predicting (incl. early detection of) a microbial infection, and may even be used for environmental diagnostics, such as for determining the microbial status of a sample source, wherein said sample source is of environmental, plant, animal or food origin, or a sample of a pharmaceutical or chemical product intended to be devoid of microbes or microbial DNA and wherein specific profiles of ITS regions (or the absence thereof) are indicative of sterility of said sample, quality of the environment, microbial safety of a food, pharmaceutical product, the quality of a chemical product or the health of plant or animal.

III. Machine Learning Algorithms for Predicting Clinical Status of Samples

Diagnosis, monitoring or typing can be performed by assessing the absence or presence of specific peaks, the abundance thereof, or the peak volume, or by applying machine learning algorithms on at least one, preferably at least 2, 3, 4, 5, 6, 7, 8, 9, or 10 signatures or profiles, preferably having been typed previously as desirable (e.g. healthy) and/or undesirable (e.g. diseased) signatures or profiles. Suitable machine learning algorithms include Support Vector Machines, Random Forest or partial least squares discriminant analysis (the result of the latter is for example displayed herein as ROC curves). The skilled person is aware of these and other machine learning programs and knows how to apply them on generated data sets in order provide a tool for diagnosis, monitoring or typing in methods as described herein. One machine learning algorithm, the partial least squares discriminant analysis (PLS-DA), is described herein below.

Partial Least Squares Discriminant Analysis (PLS-DA)

A partial least squares discriminant analysis (PLS-DA) regression model can be used for predicting whether a target or test sample belongs to a desirable signature or to a non-desirable signature; for example whether it belongs to a diseased subject or to a healthy subject. PLS-DA is a supervised classification method, which aims to find linear transformations of a matrix of predictors and categorical responses so as to maximize their covariance. [Rajilić-Stojanović M, Biagi E, Heilig H G, et al. 2011. Gastroenterology 141:1792-801]. The PLS-DA model can be constructed on the basis of four different datasets: one for each of the three separate phylum groups and one for the overall microbial composition, by pooling all phyla. Under the assumption that the more discriminant variables are the ones with a higher variance, a preliminary variable selection can be performed by filtering out low variance predictors.

PLS-DA model validation can be carried out by a 10-fold cross-validation procedure. In practice, the dataset is split into 90% of samples for model construction (i.e. the training set) with the aim to predict the other 10% (i.e. the test set). This procedure is repeated for 10 iterations, where each sample serves as a test sample exactly once. Accuracy rates, specificity and sensitivity are computed for the samples that are used as a test set in every iteration, and the model predictive power is further assessed using a receiver operating characteristic (ROC) curve, a function of the true positive rate (TPR or sensitivity) and false positive rate (FPR or 1-specificity).

PLS-DA provides a quantitative estimate of the discriminatory power of each descriptor by means of VIP (variable importance for the projection) parameters. VIP values rank the descriptors by their ability to discriminate different groups and are therefore considered an appropriate quantitative statistical parameter. The VIP criterion can be used to rank the different OTUs based on their contribution to the response variable (for example, clinical status such as diverticulitis: present or absent) and PLS components. Only the OTUs with the highest contribution (VIP score>1.2) are considered. The OTUs resulting from this selection are translated to most likely bacterial species by comparison to a database consisting of >1500 bacterial species and their associated IS lengths. PLS-DA analysis can be performed using the DiscriMiner package in R (version 2.15.2). All data visualizations can be performed with the Spotfire® software package (TIBCO, Palo Alto, Calif., USA).

IV. The present invention also envisions that a sample of interest is collected and provided by a user, such as a patient or medical practitioner, to a testing facility for determining a signature of the microbiome as described herein. The methods of the present invention may then be performed by the testing facility on the sample provided by the user, and the resulting test signature may subsequently be returned by the testing facility to the user that has provided the test sample.

The present invention furthermore envisions a system wherein a user in possession of a test signature, is able to provide the test signature to an analysis facility for providing a diagnostic test result based on the test signature. The analysis facility is preferably a computer system comprising one or more of a database of reference signatures stored on a computer-readable storage medium, a computer program comprising instructions configured to cause a computer system to perform the operations of comparing test signatures with reference signatures, and machine learning algorithms for predicting the diagnostic status of signatures based on comparison with a learned set of reference signatures, such as for predicting the diagnostic test result of a clinical sample, for instance as described in great detail herein above, and in the Examples herein below. The test signature may be provided to the analysis facility in the form of an electronic input message, optionally following a user authentication process, such as a verification process based on a pin code or biometric code.

The computer system of the analysis facility generates an electronic output message containing the predicted diagnostic test result and this message may be stored on a computer-readable storage medium, and/or the message may be communicated to a user-specified device, such as a smartphone or tablet. The communication between the computer system and the user-specified device may be via a wireless network system, the internet, email, sms, WhatsApp, or dedicated apps, and access to the contents of the output message is optionally again subject to secure access using a user authentication process, such as a verification process based on a pin code or biometric code.

Embodiments of this invention are inter alia:

Embodiment 1

A PCR calibrator system, comprising a set of PCR amplification primers at least one of which primers comprises a label, and a set of at least two PCR calibrators, each PCR calibrator consisting of a DNA fragment comprising a spacer region having a DNA sequence of a given length flanked by upstream and downstream adapter DNA sequences that comprise primer binding sites for binding of said PCR amplification primers wherein said set of PCR amplification primers is for PCR amplifying the spacer region DNA sequence of all PCR calibrators in said set of at least two PCR calibrators, wherein the spacer region DNA sequence comprised in each of said PCR calibrators in said set of at least two PCR calibrators is of a different length, and wherein each PCR calibrator in said set of at least two PCR calibrators is present in equal amount or in a known amount relative to other PCR calibrators in said set.

Embodiment 2

A PCR calibrator system according to embodiment 1, wherein said spacer region DNA sequence is the sequence of at least a part of a microbial 16S-23S rRNA internal transcribed spacer (ITS) region, and wherein said adapter DNA sequences in said set of at least two PCR calibrators replace the DNA sequences of the conserved DNA regions comprised in the 16S and 23S rRNA gene sequences upstream and downstream of said ITS region in the microbial genome from which said ITS region originates and wherein said adapter DNA sequences have less than 30% sequence identity with the DNA sequences of said conserved DNA regions.

Embodiment 3

A set of at least two PCR calibrators as defined in embodiment 1 or 2, wherein said set is comprised in a single replicon or single amplifiable template, preferably a DNA plasmid.

Embodiment 4

A method of analyzing the composition of a microbiome based on taxonomic variation in the DNA sequence of the microbial 16S-23S rRNA internal transcribed spacer (ITS) regions in the genomic DNA of the microorganisms in said microbiome, wherein the sequences of conserved DNA regions comprised in the 16S and 23S rRNA sequences flanking said ITS region in the genomic DNA of said microorganisms comprise primer binding sites for amplification of said ITS regions, said method comprising the steps of:

a) providing a sample of genomic DNA from a microbiome;
b) providing a PCR calibrator system as defined in embodiment 1 or 2;
c) adding said set of at least two PCR calibrators from said PCR calibrator system to said sample of genomic DNA;
d) performing a PCR amplification reaction on said sample of genomic DNA comprising said set of at least two PCR calibrators using said set of PCR amplification primers from said PCR calibrator system as a first set of amplification primers to amplify and provide amplification products of said ITS region(s) comprised in said set of at least two PCR calibrators, and using at least a second set of PCR amplification primers directed to said flanking conserved DNA regions to thereby co-amplify and provide amplification products of said ITS regions comprised in said sample of genomic DNA, and;
e) providing a standard curve by determining the PCR amplification efficiency of each of said at least two PCR calibrators from said PCR calibrator system in said PCR amplification reaction of step d) and expressing said PCR amplification efficiency as a function of the length of the DNA sequence of the ITS region;
f) determining the length-specific amplification efficiency for ITS regions of different length comprised in said genomic DNA sample and amplified in step d) using the standard curve as provided in step e);
g) determining the abundance of microbial 16S-23S rRNA internal transcribed spacer (ITS) regions of different length in said microbiome using the length-specific amplification efficiencies determined in step f), and
h) analyzing the composition of a population of microorganisms based on the abundances of ITS regions of different length determined in step g).

Embodiment 5

The method of embodiment 4, wherein said standard curve is based on at least five PCR calibrators of different length ranging in length from 50 to 1200 bps.

Embodiment 6

The method of embodiment 4 or 5, wherein said step d) of performing a PCR amplification reaction on said sample of genomic DNA using at least a second set of PCR amplification primers directed to said flanking conserved DNA regions comprises the use of a set of PCR amplification primers for amplifying the 16S-23S rRNA internal transcribed spacer (ITS) regions in the genomic DNA of the phyla Firmicutes and Bacteroidetes and a set of PCR amplification primers for amplifying the 16S-23S rRNA internal transcribed spacer (ITS) regions in the genomic DNA of the phylum Proteobacteria.

Embodiment 7

The method of embodiment 6, wherein said set of PCR amplification primers for amplifying the 16S-23S rRNA internal transcribed spacer (ITS) regions in the genomic DNA of the phyla Firmicutes and Bacteroidetes comprises the use of:

a) the forward primer 5'-CTGGATCACCTCCTTTCTAWG-3' (SEQ ID NO: 1) comprising a first fluorescent label,
b) the forward primer 5'-CTGGAACACCTCCTTTCTGGA-3' (SEQ ID NO: 2) comprising a second fluorescent label;
c) and three unlabeled reverse primers 5'-AGGCATCCACCGTGCGCCCT-3' (SEQ ID NO: 3); 5'-AGGCATTCACCRTGCGCCCT-3' (SEQ ID NO: 4); and 5'-AGGCATCCRCCATGCGCCCT-3' (SEQ ID NO: 5).

Embodiment 8

The method of embodiment 6 or 7, wherein said set of PCR amplification primers for amplifying the 16S-23S rRNA internal transcribed spacer (ITS) regions in the genomic DNA of the phylum Proteobacteria comprises the use of:
a) the forward primer 5'-CCGCCCGTCACACCATGG-3' (SEQ ID NO: 6)
b) at least one of the reverse primers selected from the group consisting of 5'-AATCTCGGTTGATTTCTTTTCCT-3' (SEQ ID NO: 7), 5'-AATCTCGGTTGATTTCTTCTCCT-3' (SEQ ID NO: 8), 5'-AATCTCTTTTGATTCTTTTCCTCG-3' (SEQ ID NO: 9), 5'-AATCTCATTTGATGTCTTTTCCTCG-3' (SEQ ID NO: 10), 5'-AATCTCTTTTGATTTCTTTTCCTTCG-3' (SEQ ID NO: 11), 5'-AATCTCTCTTGATTTCTTTTCCTTCG-3' (SEQ ID NO: 12), 5'-AATCTCAATTGATTCTTTTCCTAAGG-3' (SEQ ID NO: 13), wherein at least one of said primers comprises a fluorescent label.

Embodiment 9

The method of any one of embodiments 4-8, wherein said microbiome is the microbiome of the respiratory tract, oral cavity, skin, gastrointestinal tract, or urogenital tract or that of urine, saliva, sputum, pus, wound fluid, or feces, preferably of the human body, or the microbiome associated with soil, waterbodies or plants.

Embodiment 10

A method for diagnosing or monitoring a digestive tract or gastrointestinal disorder in a patient, wherein the disorder is selected from the group consisting of digestive tract or gastrointestinal disorders associated with inflammatory bowel disease (IBD), diverticulitis, irritable bowel syndrome (IBS), coeliac, lactose intolerance, Necrotising Enterocolitis (NEC), *Clostridium Difficile* Associated Diarrhea and colorectal cancer, or comorbid disorder selected from the group consisting of attention-deficit/hyperactivity disorder (ADHD), obsessive-compulsive disorder (OCD), anxiety, stress, eating disorder, major depressive disorder (MDD), bipolar disorder, depression, and schizophrenia, said method comprising performing the method of any one of embodiments 4-9 on a sample of the intestinal flora, and optionally treating the patient by pharmacological intervention.

Embodiment 11

Method according to embodiment 10, wherein said sample of intestinal flora is a sample obtained from small or large intestine, preferably colon or rectum, preferably in the form of a biopsy specimen of gastrointestinal mucosa or in the form of a feces sample, more preferably wherein said sample is obtained using a rectal swab.

Embodiment 12

Method according to embodiment 10 or 11, wherein IBD is selected from Crohn's disease, colitis ulcerosa, collageneous colitis, lymfocytic colitis, ischemic colitis, microscopic colitis, Behçet's syndrome, diversion colitis, diverticular colitis, eosinophilic colitis, and radiation colitis.

Embodiment 13

Method according to any one of embodiments 10-12, wherein the digestive tract or gastrointestinal disorder is treated by pharmacological intervention with therapeutic agent selected from anti-inflammatory agents, and antibiotic agents, TNF-alfa inhibitors, including infliximab and adalimumab, and 5-ASA formulations, including sulfasalazine and mesalazine.

Embodiment 14

Method according to any one of embodiments 10-12, wherein the comorbid disorder is attention-deficit/hyperactivity disorder (ADHD) and the pharmacological intervention comprises treating the patient with a methylphenidate stimulant, preferably selected from the group consisting of Adderall®, Concerta®, Vyvanse®, and Ritalin.

Embodiment 15

Method according to any one of embodiments 10-12, wherein the comorbid disorder is selected from obsessive-compulsive disorder (OCD), anxiety, stress, major depressive disorder (MDD), bipolar disorder symptoms, depression, and schizophrenia, and the pharmacological intervention comprises treating the patient with an antidepressant, preferably selective serotonin reuptake inhibitors (SSRIs), more preferably fluoxetine, citalopram, escitalopram, paroxetine, or sertraline; or an antipsychotic selected from the group consisting of aripiprazole, asenapine, clozapine, iloperidone, olanzapine, paliperidone, quetiapine, risperidone, and ziprasidone.

Embodiment 16

Method according to any one of embodiments 10-12, wherein the eating disorder is anorexia nervosa or bulimia nervosa, and the pharmacological intervention comprises the administration of an antidepressant, preferably selective serotonin reuptake inhibitors (SSRIs), more preferably fluoxetine, citalopram, escitalopram, paroxetine, or sertraline; an antihistamine; or an antipsychotic, preferably selected from the group consisting of aripiprazole, asenapine, clozapine, iloperidone, olanzapine, paliperidone, quetiapine, risperidone, and ziprasidone.

Embodiment 17

A method for diagnosing or monitoring a systemic disease in a patient, said method comprising performing the method of any one of embodiments 4-9 on a body sample of said patient, and optionally treating the patient by pharmacological intervention.

Embodiment 18

Method according to embodiment 17, wherein said systemic disease is selected from the group consisting of arthritis, sarcoidosis, mixed connective tissue disease, spondylitis ankylopoetica, osteoporosis, juvenile idiopathic arthritis, osteoarthritis, rheumatoid arthritis, sepsis, Behçet's disease, Sjögren's syndrome, fibromyalgia, sclerodermia, Raynaud's phenomenon, and systemic lupus erythematosus, said method comprising performing the method of any one of embodiments 4-9 on a sample of the intestinal flora.

Embodiment 19

A method for diagnosing or monitoring a skin disorder or chronic wound in a patient, said method comprising performing the method of any one of embodiments 4-9 on a sample of the skin or wound flora, and optionally treating the patient by pharmacological intervention.

Embodiment 20

Method according to embodiment 19, wherein said skin disorder is psoriasis, eczema, acne, or rosacea, or wherein said chronic wound is a diabetic ulcer, or ulcer associated with vascular disease and wherein the pharmacological intervention comprises the administration of an antibiotic or anti-inflammatory agent, preferably a topical corticosteroid selected from cortisone, hydrocortisone, prednisone and prednisolone, methylprednisolone, dexamethasone, triamcinolone, mometasone, fluticasone, betamethasone, halometasone and desonide, preferably wherein the antibiotic agent is provided in the form of an antibiotic ointment, preferably selected from fusidin cream, flammazin cream, bactroban ointment, baneocin ointment, erythromycin unguent, chlorhexidin cream, and mupirocin cream.

Embodiment 21

A method of determining fertility or the probability of success of an in vitro fertilization or embryo transfer procedure in a female, said method comprising performing the method of any one of embodiments 4-9 on a sample of the vaginal flora, and optionally treating the patient by pharmacological intervention.

Embodiment 22

A method for diagnosing or monitoring bacterial vaginosis, said method comprising performing the method of any one of embodiments 4-9 on a sample of the vaginal flora, and optionally treating the patient by pharmacological intervention, preferably wherein the pharmacological intervention comprises the systemic or topical administration of an antibiotic, preferably metronidazole, clindamycin, amoxicillin-clavulanate or fluconazole.

Embodiment 23

A method for diagnosing or monitoring an oral, nasal or oropharyncheal disorder selected from periodontitis, periimplantitis, and oro-nasopharyngeal carcinoma said method comprising performing the method of any one of embodiments 4-9 on a sample of the oral flora, and optionally treating the patient by pharmacological intervention, preferably wherein the pharmacological intervention comprises the systemic, topical or local administration of an antibiotic or antineoplastic agent.

Embodiment 24

A method for diagnosing or monitoring a disorder that affects the upper or lower respiratory tract, selected from respiratory infection, chronic obstructive pulmonary disease (COPD), asthma, cystic fibrosis and lung cancer, said method comprising performing the method of any one of embodiments 4-9 on a pulmonary sample selected from bronchoalveolar lavage, a sputum sample and a lung biopsy, and optionally treating the patient by pharmacological intervention, preferably wherein the pharmacological intervention comprises the systemic, topical or local administration of an antibiotic agent, anti-inflammatory agent or antineoplastic agent.

Embodiment 25

A method for diagnosing or monitoring a microbial infection, said method comprising performing the method of any one of embodiments 4-9 on a liquor sample, a pleural sample, a blood sample, a urine sample, an abscess sample, or a tissue sample of an organ, and optionally treating the patient by pharmacological intervention, preferably wherein the pharmacological intervention comprises the systemic, topical or local administration of an antibiotic agent.

Embodiment 26

A method for determining the microbial status of a sample, wherein said sample is of environmental, plant, animal or food origin or a sample of a pharmaceutical or chemical product intended to be devoid of microbes or microbial DNA, said method comprising performing the method of any one of embodiments 4-9 on a sample from said source, and optionally treating the source from which the sample was obtained, wherein said status is indicative of sterility of said sample, quality of the environment, microbial safety of food, or the health of plant or animal, preferably wherein the treatment comprises the reduction of microbial growth in said sample source or elimination of microbes or microbial DNA from said sample source.

Embodiment 27

A method of typing the intestinal flora of a subject for having a diverticulitis signature, comprising analyzing the composition of the population of microorganisms in said intestinal flora based on taxonomic variation in the DNA sequence of the microbial 16S-23S rRNA internal transcribed spacer (ITS) regions in the genomic DNA of said microorganisms, wherein the sequences of conserved DNA regions comprised in the 16S and 23S rRNA sequences flanking said ITS region in the microbial genome comprise primer binding sites for amplification of said ITS regions, said analysis comprising the steps of:
a) providing a sample of genomic DNA from the population of microorganisms constituting the intestinal flora of a subject;
b) performing a PCR amplification reaction on said sample of genomic DNA using at least one set of PCR amplification primers directed to said flanking conserved DNA regions to thereby amplify and provide amplification products of said ITS regions comprised in said genomic DNA sample;
c) analyzing said amplification products to thereby provide a test signature of the composition of the population of microorganisms in said intestinal flora;
d) comparing said test signature with a reference signature of a healthy subject and/or a subject suffering from diverticulitis and classifying the test signature as a signature of a healthy subject or as a signature of a subject suffering from diverticulitis.

Embodiment 28

The method of any one of embodiment 27, wherein the signature of a subject suffering from diverticulitis is characterized by increased peak area or peak height in the capillary gel electrophoresis peak profile for DNA fragments having a length in the range from 400-450 nucleotides, wherein said peak profile is produced by capillary electrophoretic analysis of said amplification products.

Embodiment 29

A method of typing the intestinal microbiome of a subject for having the signature of a microbiome associated with a disease selected from a digestive tract or gastrointestinal disorder, or systemic disease as defined in any one of embodiments 10-18, said method comprising analyzing the composition of the population of microorganisms in the intestinal microbiome based on taxonomic variation in the DNA sequence of the microbial 16S-23S rRNA internal transcribed spacer (ITS) regions in the genomic DNA of said microorganisms, wherein the sequences of conserved DNA regions comprised in the 16S and 23S rRNA sequences flanking said ITS region in the microbial genome comprise primer binding sites for amplification of said ITS regions, said analysis comprising the steps of:
a) providing a sample of genomic DNA from the population of microorganisms constituting the intestinal microbiome of a subject;
b) performing a PCR amplification reaction on said sample of genomic DNA using at least one set of PCR amplification primers directed to said flanking conserved DNA regions to thereby amplify and provide amplification products of said ITS regions comprised in said genomic DNA sample;
c) analyzing said amplification products to thereby provide a test signature of the composition of the population of microorganisms in said intestinal microbiome;
d) comparing said test signature with a reference signature of a healthy subject and/or a subject suffering from the digestive tract or gastrointestinal disorder, or systemic disease and classifying the test signature as a signature of a healthy subject or as a signature of a subject suffering from a digestive tract or gastrointestinal disorder, or systemic disease.

Embodiment 30

The method of embodiment 29, wherein said digestive tract or gastrointestinal disorder, or systemic disease is selected from Crohn's disease, colitis ulcerosa, collageneous colitis, lymfocytic colitis, ischemic colitis, microscopic colitis, Behçet's syndrome, diversion colitis, diverticular colitis, eosinophilic colitis, radiation colitis, diverticulitis, irritable bowel syndrome (IBS), coeliac, lactose intolerance, Necrotising Enterocolitis (NEC), *Clostridium Difficile* Associated Diarrhea, colorectal cancer, attention-deficit/hyperactivity disorder (ADHD), obsessive-compulsive disorder (OCD), anxiety, stress, eating disorder, major depressive disorder (MDD), bipolar disorder, depression, schizophrenia, arthritis, sarcoidosis, mixed connective tissue disease, spondylitis ankylopoetica, osteoporosis, juvenile idiopathic arthritis, osteoarthritis, rheumatoid arthritis, sepsis, Behçet's disease, Sjögren's syndrome, fibromyalgia, sclerodermia, Raynaud's phenomenon, and systemic lupus erythematosus.

Embodiment 31

A method of typing a sample of the skin or wound flora of a subject for having the signature of a skin disorder or chronic wound, said method comprising analyzing the composition of the population of microorganisms in the intestinal microbiome based on taxonomic variation in the DNA sequence of the microbial 16S-23S rRNA internal transcribed spacer (ITS) regions in the genomic DNA of said microorganisms, wherein the sequences of conserved DNA regions comprised in the 16S and 23S rRNA sequences flanking said ITS region in the microbial genome comprise primer binding sites for amplification of said ITS regions, said analysis comprising the steps of:
a) providing a sample of genomic DNA from the population of microorganisms constituting the intestinal microbiome of a subject;
b) performing a PCR amplification reaction on said sample of genomic DNA using at least one set of PCR amplification primers directed to said flanking conserved DNA regions to thereby amplify and provide amplification products of said ITS regions comprised in said genomic DNA sample;
c) analyzing said amplification products to thereby provide a test signature of the composition of the population of microorganisms in said intestinal microbiome;
d) comparing said test signature with a reference signature of a healthy subject and/or a subject suffering from a skin disorder or chronic wound and classifying the test signature as a signature of a healthy subject or as a signature of a subject suffering from a skin disorder or chronic wound preferably wherein said skin disorder is psoriasis, eczema, acne, or rosacea, or wherein said chronic wound is a diabetic ulcer, or ulcer associated with vascular disease.

Embodiment 32

A method of typing a sample of a subject for determining fertility or the probability of success of an in vitro fertilization or embryo transfer procedure in a female, for diagnosing or monitoring bacterial vaginosis, for diagnosing or monitoring an oral, nasal or oropharyncheal disorder selected from periodontitis, periimplantitis, and oro-nasopharyngeal carcinoma for diagnosing or monitoring a disorder that affects the upper or lower respiratory tract, selected from respiratory infection, chronic obstructive pulmonary disease (COPD), asthma, cystic fibrosis and lung cancer,
said method comprising analyzing the composition of the population of microorganisms in said sample obtained from said subject based on taxonomic variation in the DNA sequence of the microbial 16S-23S rRNA internal transcribed spacer (ITS) regions in the genomic DNA of said microorganisms, wherein the sequences of conserved DNA regions comprised in the 16S and 23S rRNA sequences flanking said ITS region in the microbial genome comprise primer binding sites for amplification of said ITS regions, said analysis comprising the steps of:
a) providing a sample of genomic DNA from the population of microorganisms constituting the intestinal microbiome of a subject;
b) performing a PCR amplification reaction on said sample of genomic DNA using at least one set of PCR amplification primers directed to said flanking conserved DNA regions to thereby amplify and provide amplification products of said ITS regions comprised in said genomic DNA sample;
c) analyzing said amplification products to thereby provide a test signature of the composition of the population of microorganisms in said intestinal microbiome;

d) comparing said test signature with a reference signature of a beneficial sample having the desired signature and classifying the test signature.

Embodiment 33

The method of any one of embodiments 25-32, wherein said step b) of performing a PCR amplification reaction on said sample of genomic DNA using at least one set of PCR amplification primers directed to said flanking conserved DNA regions comprises the use of a set of PCR amplification primers for amplifying the 16S-23S rRNA internal transcribed spacer (ITS) regions in the genomic DNA of the phyla Firmicutes and Bacteroidetes and a set of PCR amplification primers for amplifying the 16S-23S rRNA internal transcribed spacer (ITS) regions in the genomic DNA of the phylum Proteobacteria.

Embodiment 34

The method of embodiment 33, wherein said set of PCR amplification primers for amplifying the 16S-23S rRNA internal transcribed spacer (ITS) regions in the genomic DNA of the phyla Firmicutes and Bacteroidetes comprises the use of:
a) the forward primer 5'-CTGGAT-CACCTCCTTTCTAWG-3' (SEQ ID NO: 1) comprising a first fluorescent label,
b) the forward primer 5'-CTG-GAACACCTCCTTTCTGGA-3' (SEQ ID NO: 2) comprising a second fluorescent label;
c) and three unlabeled reverse primers 5'-AGGCATC-CACCGTGCGCCCT-3' (SEQ ID NO: 3); 5'-AGGCATT-CACCRTGCGCCCT-3' (SEQ ID NO: 4); and 5'-AGG-CATCCRCCATGCGCCCT-3' (SEQ ID NO: 5).

Embodiment 35

The method of embodiment 33 or 34, wherein said set of PCR amplification primers for amplifying the 16S-23S rRNA internal transcribed spacer (ITS) regions in the genomic DNA of the phylum Proteobacteria comprises the use of:
a) the forward primer 5'-CCGCCCGTCACACCATGG-3' (SEQ ID NO: 6)
b) at least one of the reverse primers selected from the group consisting of 5' AATCTCGGTTGATTTCTTTTCCT-3' (SEQ ID NO: 7), 5'-AATCTCGGTTGATTTCTTCTCCT-3' (SEQ ID NO: 8), 5'-AATCTCTTTTGAT-TTCTTTTCCTCG-3' (SEQ ID NO: 9), 5'-AATCTCATTTGATGTCTTTTCCTCG-3' (SEQ ID NO: 10), 5'-AATCTCTTTTGATTTCTTTTCCTTCG-3' (SEQ ID NO: 11), 5'-AATCTCTCTTGATTTCTTTTCCTTCG-3' (SEQ ID NO: 12), 5'-AATCTCAATTGAT-TTCTTTTCCTAAGG-3' (SEQ ID NO: 13), wherein at least one of said primers comprises a fluorescent label, preferably wherein said fluorescent label differs from fluorescent labels of other phylum-specific primers in said reaction.

Embodiment 36

The method of any one of embodiments 25-35, wherein the signature of a subject suffering from diverticulitis is characterized in having an increased diversity in the phylum Proteobacteria as calculated using the Shannon index.

Embodiment 37

The method according to embodiment 36, wherein the increased diversity in the phylum Proteobacteria is due to an increased diversity in the family Enterobacteriaceae.

Embodiment 38

The method of embodiment 36, wherein an increased diversity in the phylum Proteobacteria is indicated by an increase in the presence of at least one of the species selected from the group consisting of *Escherichia coli*, *Klebsiella pneumoniae*, *Enterobacter aerogenes*, *Serratia marcescens*, *Klebsiella variicola*, *Providencia stuartii*, *Desulfovibrio* spp., *Stenotrophomonas* spp. (*Xanthomonas* spp.), *Pseudomonas aeruginosa*, *Burkholderia* spp. and *Aggregatibacter actinomycetemcomitans*.

Embodiment 39

The method of any one of embodiments 25-38, comprising the use of a PCR calibrator system as defined in embodiment 1 or 2 in accordance with a method as described in any one of embodiments 4-9.

Embodiment 40

The method of any one of embodiments 25-39, wherein step a) of providing a sample of genomic DNA from the population of microorganisms constituting the intestinal flora of a subject comprises the sampling of the intestinal flora using a rectal swab.

Embodiment 41

A method of sampling the intestinal flora for analyzing the taxonomic composition of microorganisms microbiome based on taxonomic variation in the DNA sequence of the microbial 16S-23S rRNA internal transcribed spacer (ITS) regions in the genomic DNA of said microorganisms, wherein said sample of intestinal flora is obtained by using a rectal swab.

Embodiment 42

A set of oligonucleotide primers for amplifying sequences of the 16S-23S intergenic region of the phylum Proteobacteria from a sample of microbial genomic DNA, said set comprising the forward primer having the sequence 5'-CCGCCCGTCACACCATGG-3' (SEQ ID NO: 6) and at least 2 reverse primers selected from the group of primers indicated having the sequence 5'-AATCTCGGTTGAT-TTCTTTTCCT-3' (SEQ ID NO: 7), 5'-AATCTCGGTT-GATTTCTTCTCCT-3' (SEQ ID NO: 8), 5'-AATCTCTTTT-GATTTCTTTTCCTCG-3' (SEQ ID NO: 9), 5'-AATCTCATTTGATGTCTTTTCCTCG-3' (SEQ ID NO: 10), 5'-AATCTCTTTTGATTTCTTTTCCTTCG-3' (SEQ ID NO: 11), 5'-AATCTCTCTTGATTTCTTTTCCTTCG-3' (SEQ ID NO: 12), 5'-AATCTCAATTGAT-TTCTTTTCCTAAGG-3' (SEQ ID NO: 13), wherein preferably at least one of said primers comprises a detectable label.

For the purpose of clarity and a concise description features are described herein as part of the same or separate embodiments, however, it will be appreciated that the scope of the invention may include embodiments having combinations of all or some of the features described herein. For instance, the primers and probes as described herein, such as the phylum-specific Proteobacteria primers, may optionally be used in any of the aspects described herein. Likewise, the calibrator system is envisioned as a preferred embodiment in any of the methods and products described.

The invention will now be illustrated by the following example, which is provided by way of illustration and not of limitation and it will be understood that many variations in the methods described and the amounts indicated can be made without departing from the spirit of the invention and the scope of the appended claims.

EXAMPLES

Example 1. PCR Calibrator System

This example describes in more detail an embodiment of the PCR calibrator system of the invention.

Single copies of 5 PCR calibrators varying in length from 190, 300, 480, 630, and 820 nucleotides, each calibrator including adaptor sequences for binding of amplification primers, was inserted into a plasmid, pUC18. The PCR calibrators were based on one of the 16S-23S ITS sequences of the bacteria *Bacillus cereus, Staphylococcus epidermidis, Parabacteroides distasonis, Veillonella parvula, Staphylococcus lugdunensis* and *Escherichia coli*. The adaptor sequences consisted of sequences complementary to the primers MPICf (5'-GACCTAGTGGAGGAAAGATAC-3' (SEQ ID NO: 14); forward primer, labeled with a fluorescent label) and MPICr (5'-TCCGTAGGTGGCACGCGGGA-3' (SEQ ID NO: 15); reverse primer, unlabeled).

The individual PCR calibrator sequences with flanking adaptors were divided in the plasmid by restriction sites for the restriction enzymes Not1, Nde1 and Sca1. The plasmid was cloned and replicated in *E. coli* cells of the strain DH5a. Plasmid DNA was then isolated and the individual PCR calibrator fragments were released by digestion with the restriction enzyme. This resulted in a mixture of 5 PCR calibrators, each having different length and present in exact equal amounts.

The PCR calibrators were amplified using the primers MPICf and MPICr described above in the presence of a representative (inhibiting) genomic DNA sample (genomic DNA from intestinal flora), and in an non-inhibiting control environment (demineralized water). Amplifications were carried out on a GeneAmp® PCR system 9700 (Applied Biosystems, Foster City, Calif.). Cycling conditions for PCR were 72° C. for 2 min; 35 cycles of 94° C. for 30 s, 56° C. for 45 s, and 72° C. for 1 min; and a final extension at 72° C. for 5 min. The PCR mixture, with a final volume of 25 µl, contained 10 µl of buffered DNA (test) or demineralized water (control), 1× superTaq buffer (SphaeroQ, Gorinchem, the Netherlands), 200 µM deoxynucleoside triphosphate, 0.04% BSA, 1 U of superTaq, and 0.13 µM of each of the two primers.

Following amplification, and optional purification of the amplification products, 5 µl of the PCR product was mixed separately with 19.9 µl formamide and 0.1 µl Mapmaker 1000 ROX labeled size marker (BioVentures, Murfreesboro, Tenn., USA). Subsequently, DNA fragment analysis was performed on both samples with an ABI Prism 3130XL Genetic Analyzer (Applied Biosystems). All data were pre-processed with the IS-pro proprietary software suite (IS-Diagnostics, Amsterdam, the Netherlands). This process resulted in profiles consisting of peaks with a specific length, measured in nucleotides, reflecting lengths of IS fragments, and a specific height, measured in relative fluorescence units (RFU), reflecting quantity of PCR product.

FIG. 1A shows the profile as obtained for the test sample containing the five PCR calibrator fragments after amplification and length sorting by capillary gel electrophoresis. It is clear that fragments of different length were amplified with different efficiency and yielded peaks of differing height.

Figure 1B:
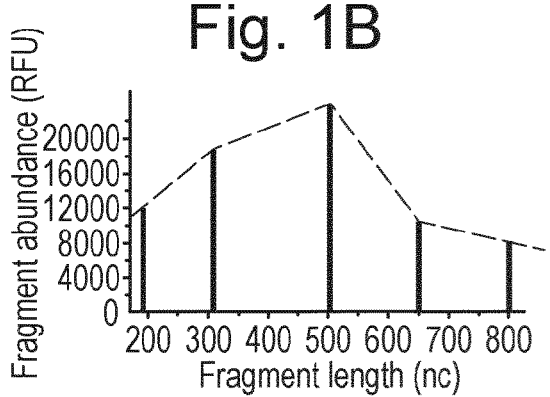
FIG. 1B. Multi-linear model of amplification efficiency profile.
Figure 1C:
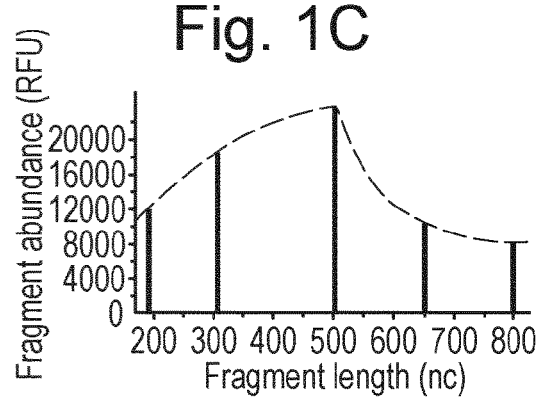
FIG. 1C. Non-linear model of amplification efficiency.
Figure 1D:
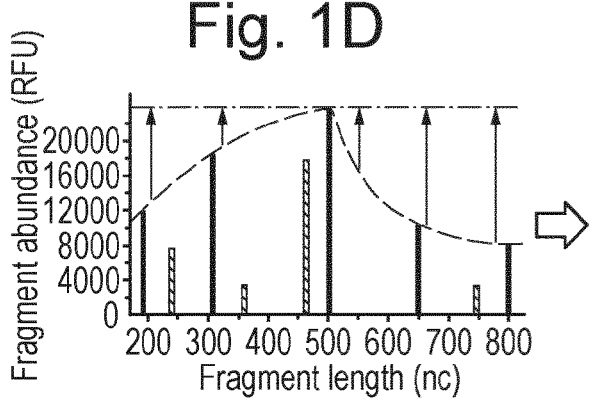
FIG. 1D. Example of the application of a corrective factor as estimated by the amplification function on all peaks in a profile.
Figure 1E:
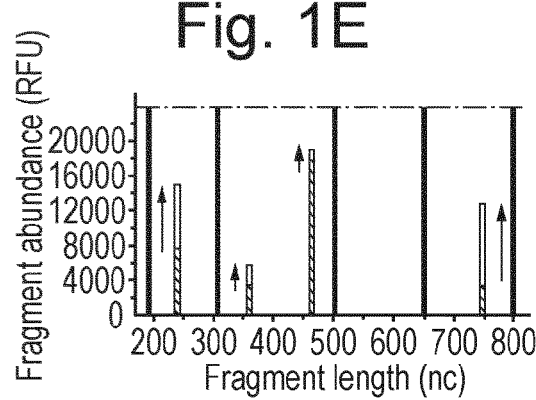
FIG. 1E: Example of fragments that gain a height correction dependent on their position on the x-axis, corresponding with their fragment length.

It is shown in FIG. 1B how this profile is used to provide a multi-linear model for correction of the amplification efficiency of fragments of all sizes. It is shown in FIG. 1C how this profile is used to provide a non-linear model for correction of the amplification efficiency of fragments of all sizes. It is considered that the non-linear model for correction of amplification efficiency leads to more accurate estimations of amplification efficiency. It is further shown in FIG. 1D how a corrective factor as estimated by the amplification function is applied to all peaks in an IS-pro profile. This corrective factor is applied to each peak, and is equivalent to the distance between the amplification efficiency function and the highest point of that function for the fragment length of the peak to be corrected (left panel). When applied to a profile using equal amounts of calibrator, all PCR calibrator fragments will be equal in height. Other fragments will gain a height correction dependent on their position on the x-axis, corresponding with their fragment length (FIG. 1E).

The use of the PCR calibrator system for upscaling of partially inhibited samples is explained in FIG. 2. In panel A, a blank (uninhibited) sample is displayed, while in panel B, a test (inhibited) sample is displayed. When the height of PCR calibrator peaks in a (partially) inhibited sample are compared to those in a blank sample, a correction factor can be applied over the entire range of fragment length towards the height of the PCR calibrator peaks as observed in the uninhibited (blank) sample.

Figure 3B:
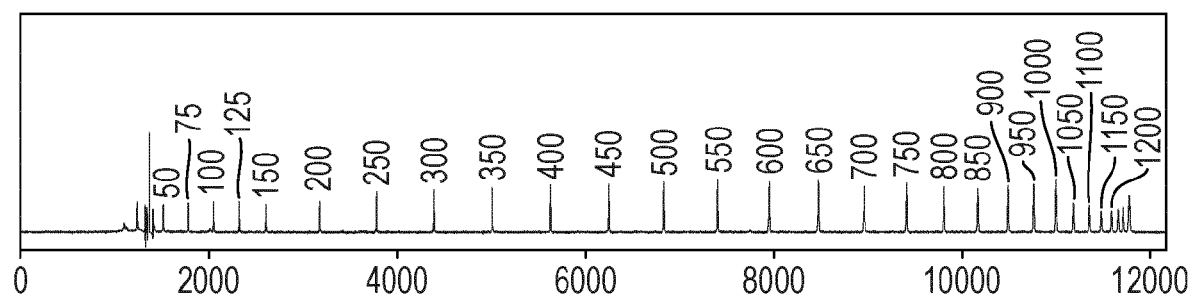
FIG. 3B: Length marker peaks are identified and assigned their respective length by an automated pre-processing software system.
Figure 3C:
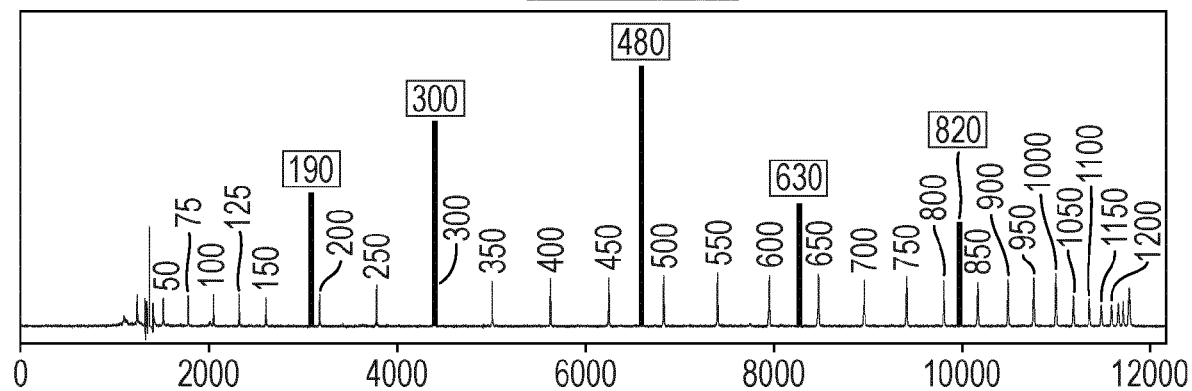
FIG. 3C: Raw capillary gel electrophoresis data for the length markers including the PCR calibrator channel.

The use of the PCR calibrator system for error checking of automated length marker detection (by pre-processing software) is explained in FIG. 3. FIG. 3A shows the raw data for the length markers following capillary gel electrophoresis. The red peak pattern is the fluorescent signal of individual markers where the x-axis represents the transition time across the capillary matrix. The intensity of the signal is displayed on the Y-axis, and represents the amount of fluorescent product. FIG. 3B is a graphic presentation of the profile after pre-processing using dedicated software to identify individual peaks and assign to each peak its respective length. FIG. 3C shows a graphic presentation of the same profile wherein the fluorescence channel of the PCR calibrator peaks is included. The PCR calibrators have been run in the capillary together with the length marker. The software assigns lengths to the PCR calibrator peaks based on its detection of the length marker. These assigned PCR calibrator lengths can then be compared to the known (true) lengths of the PCR calibrator fragments. If the assigned and true lengths are the same, the software has preformed the length marker detection correctly.

Example 2. Typing Diverticulitis in a Subject Using PCR-Based Profiling

This experiment was part of a multicenter randomized clinical trial investigating the cost-effectiveness of treatment strategies with or without antibiotics for uncomplicated acute diverticulitis. We carried out this prospective cohort study in three centers (one academic hospital and two teaching hospitals).

Subjects

Eligible diverticulitis patients were consecutive trial subjects from the three including centers of 18 years or older with a first episode of acute left-sided uncomplicated modified Hinchey 1A or 1B (Wasvary H, Turfah F, Kadro O, et al. 1999. Am Surg 65:632-5) diverticulitis demonstrated by computed tomography (CT). Informed consent was obtained from these trial subjects.

The control subjects were derived from an existing database of a mixed population of adult patients evaluated in another academic hospital for a range of gastrointestinal complaints, notably with no diagnosis of diverticulitis. Diverticulosis is a common finding at colonoscopy, with a prevalence of DD that increases with age from less than 10% in people younger than 40 years to 50-66% in octogenarians. The lifetime risk to develop diverticulitis is less than 25% in these patients. Possibly a continuum in the microbiota composition exists in patients with diverticulosis and diverticulitis. To incorporate the possibility to distinguish mild diverticulitis from diverticulosis the control group also included patients with diverticulosis.

The indications for and/or the diagnoses after colonoscopy in the control subjects were the following: follow-up after polypectomy (n=1), anaemia e.c.i. (n=1), benign neoplasm (n=3), malignant neoplasm (n=1), Morbus Crohn (n=4), ulcerative colitis (n=2), indeterminate colitis (n=1), irritable bowel syndrome (n=2), abdominal pain e.c.i. (n=1), surveillance for familial cancer susceptibility (n=3) and diverticulosis (n=6).

Rectal Swabs

In the diverticulitis patients, sampling of the intestinal flora by means of a rectal swab was performed by using standard medical methods immediately at presentation on the emergency ward, and prior to starting antibiotics when allocated to this treatment. The control subjects had their rectal swab taken prior to colonoscopy which was performed to evaluate their gastrointestinal complaints or for other indications. Swabs were gathered in sterile containers with 1 ml of reduced transport fluid (RTF) medium (Syed S A, Loesche W J. 1972. Appl Microbiol 24:638-44) and stored at −20° C. within two hours of collection.

DNA Isolation and PCR Amplification

After thawing of the samples, total DNA isolation was carried out on all samples by an automated isolation procedure (EasyMag®, Biomerieux/MP96, Roche). The principle behind the isolation includes lysis with guanidine isothiocyanate based buffers followed by automated DNA extraction with magnetic beads. The DNA was eluted in 110 μl buffer and stored at 4° C. until use for polymerase chain reaction (PCR) amplification. For all samples the procedure as described by Budding et al. 2010 was used. This procedure consisted of two multiplex PCRs: a first PCR for the phyla Firmicutes, Bacteroidetes, Actinobacteria, Fusobacteria and Verrucomicrobia was performed with 10 μl of eluted DNA. Two labeled forward primers and three universal unlabeled reverse primers were used for the amplification of the interspacer (IS) region between 16S and 23S. The labeled primers were specific for the phylum Bacteriodetes and for the combined cluster of phyla Firmicutes/Actinobacteria/Fusobacteria/Verrrucomicrobia, respectively. A second, separate PCR was performed for the phylum Proteobacteria. For this reaction, 5 μl of eluted genomic DNA was added to the same PCR mix as used for the first PCR, only with differing primers: one labeled forward primer and six reverse primers for amplification of the IS region between 16S and 23S in Proteobacteria, as described herein above. After amplification, 5 μl of each PCR product was mixed separately with 19.9 μl formamide and 0.1 μl Mapmaker 1000 ROX labelled size marker (BioVentures, Murfreesboro, Tenn., USA). Subsequently, DNA fragment analysis was performed on both samples with an ABI Prism 3130XL Genetic Analyzer (Applied Biosystems).

Data Analysis

Log 2 Transformation and Phylum Abundance

All data were pre-processed with the IS-pro proprietary software suite (IS-Diagnostics, Amsterdam, the Netherlands). This process resulted in profiles consisting of a set of 1071 peaks with a specific length, measured in nucleotides, reflecting lengths of IS fragments, and a specific height, measured in relative fluorescence units (RFU), reflecting quantity of PCR product. In order to further analyze the data, we considered each peak in a profile as an operational taxonomic unit (OTU) and its corresponding intensity as its abundance. All intensities were log 2 transformed. Log 2 transformation of complex profiles compacts the range of variation in peak heights, reducing the dominance of high peaks and including less abundant species of the microbiota in downstream analyses. This results in improved consistency of estimated correlation coefficient, lower impact of inter-run variation and improved detection of less prominent species. This conversion was used in all downstream analyses such as calculating within-sample and between-sample microbial diversity. The clustered heat map was made by generating a correlation matrix of all log 2 transformed profile data followed by clustering with the unweighted pair group method with arithmetic mean (UPGMA).

Diversity Analysis

Diversity was calculated both per phylum and per the overall microbial composition (by pooling all phyla together). Within-sample diversity was calculated as the Shannon index, that was recently shown to be a robust estimate of microbial diversity (Haegeman B, Hamelin J, Moriarty J, et al. 2013. ISME J 7:1092-101). Dissimilarities between samples, or between-sample diversity, was represented in a dissimilarity matrix that was built using the cosine distance measure. Given two vectors of attributes (two profiles in our case), A and B, the cosine dissimilarity is represented using a dotproduct and magnitude as:

$$\text{dissimilarity} = 1 - \cos(\theta) = 1 - \frac{\sum_{i=1}^{n} A_i \times B_i}{\sqrt{\sum_{i=2}^{n} (A_i)^2} \times \sqrt{\sum_{i=1}^{n} (B_i)^2}}$$

The resulting dissimilarity matrix was summarized and visualized in a low-dimensional space using principal coordinate analysis (PCoA). Diversity analysis was performed using the vegan software package in R.

Partial Least Squares Discriminant Analysis (PLS-DA)

A partial least squares discriminant analysis (PLS-DA) regression model was used for the prediction of clinical status of samples; i.e. whether it belonged to a diverticulitis patient or to a control subject. PLS-DA is a supervised classification method, which aims to find linear transformations of a matrix of predictors and categorical responses so as to maximize their covariance. [Rajilić-Stojanović M, Biagi E, Heilig H G, et al. 2011. Gastroenterology 141: 1792-801] The PLS-DA model was constructed on the basis of four different datasets: one for each of the three separate phylum groups and one for the overall microbial composition, by pooling all phyla. Under the assumption that the more discriminant variables are the ones with a higher variance, we performed a preliminary variable selection by filtering out low variance predictors. Only the top 25% most variable predictors were considered in the analysis.

PLS-DA model validation was carried out by a 10-fold cross validation procedure. In practice, the dataset was split into 90% of samples for model construction (i.e. the training set) with the aim to predict the other 10% (i.e. the test set). This procedure was repeated for 10 iterations, where each sample served as a test sample exactly once. Accuracy rates, specificity and sensitivity were computed for the samples that were used as a test set in every iteration, and the model predictive power was further assessed using a receiver operating characteristic (ROC) curve, a function of the true positive rate (TPR or sensitivity) and false positive rate (FPR or 1-specificity).

PLS-DA provides a quantitative estimate of the discriminatory power of each descriptor by means of VIP (variable importance for the projection) parameters. VIP values rank the descriptors by their ability to discriminate different groups and are therefore considered an appropriate quantitative statistical parameter. We used the VIP criterion to rank the different OTUs based on their contribution to the response variable (clinical status, i.e. diverticulitis: yes or no) and PLS components. Only the OTUs with the highest contribution (VIP score>1.2) were considered. The OTUs resulting from this selection were translated to most likely bacterial species by comparison to a database consisting of >1500 bacterial species and their associated IS lengths. PLS-DA analysis was performed using the DiscriMiner package in R (version 2.15.2). All data visualizations were performed with the Spotfire® software package (TIBCO, Palo Alto, Calif., USA).

Results

Bacterial Phylum Abundance and Profile Clustering

The Firmicutes to Bacteroidetes ratio is commonly used to describe and characterize a dysbiosis of the gut microbiota in different disease states, such as irritable bowel syndrome (IBS) and obesity (Ley et al. 2006. Nature 444: 21-28; Hastie, Tibshirani, & Friedman. The Elements of Statistical Learning. New York: Springer-Verlag 2001]. Since these two phyla are being amplified in the same PCR reaction, we could compare their relative abundance between patients and controls. The phylogenetic characterization of samples from control subjects uncovered that Bacteroidetes represented 51% and Firmicutes 49% of the total abundance in the Firmicutes/Bacteroidetes PCR. Exactly the same proportions were found for the patient group. The total load of bacteria of the Proteobacteria phylum was relatively similar between patients and controls (10.2±1.9 log 2 RFU and 10.1±2.0 log 2 RFU for patients and controls, respectively; p=0.20, Mann-Whitney U-test).

Figure 4:
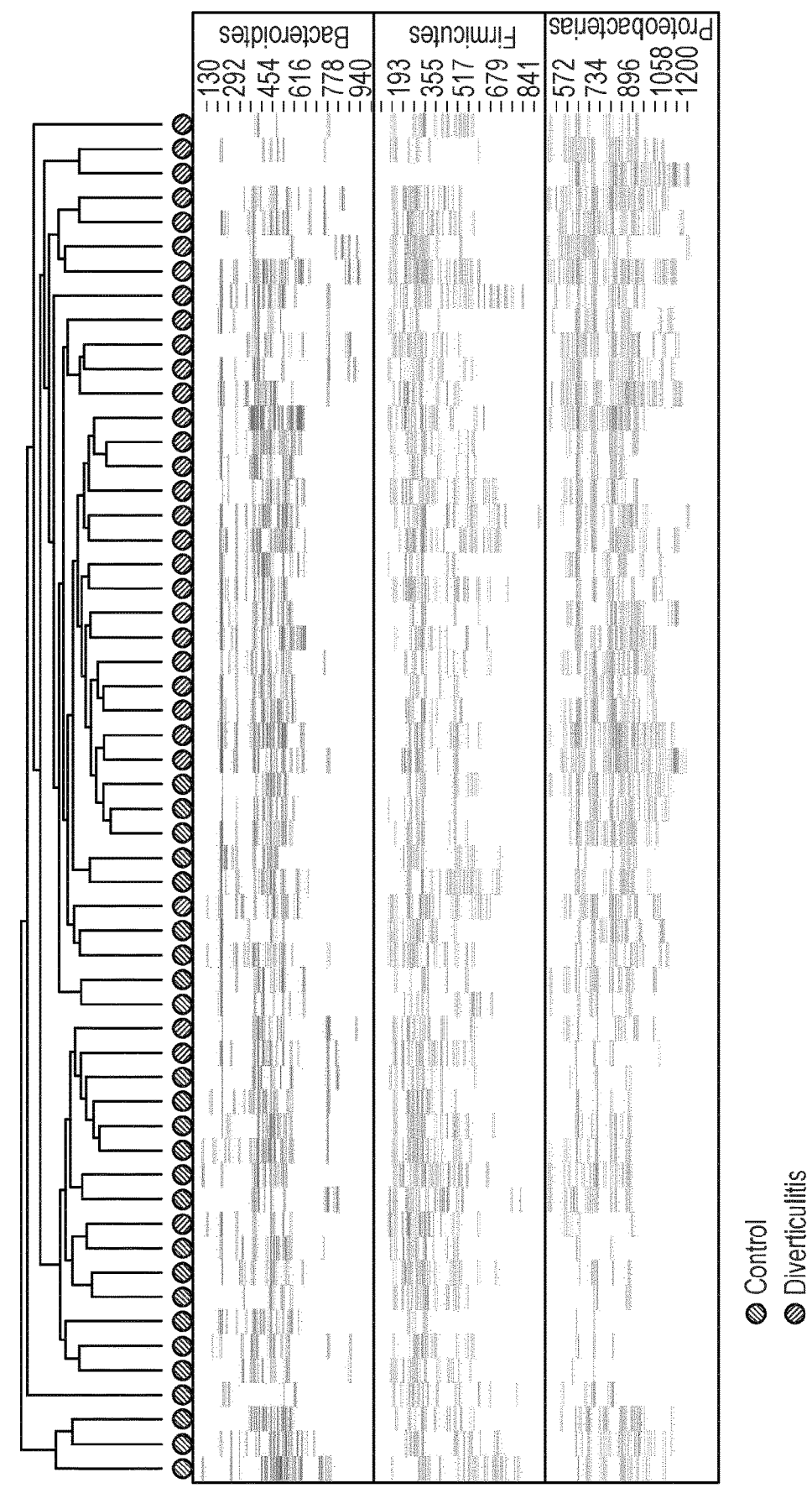
FIG. 4 shows a heat map of all profiles sorted and colored by phylum for the experiment as described in Example 2.

A heat map was generated from all IS-profiles separated by phylum. IS-profiles showed a general separation of samples from diverticulitis patients and controls when clustering was performed by Proteobacteria profile (FIG. 4).

Microbial Diversity and Composition in Diverticulitis Patients Versus Controls

Figure 5:
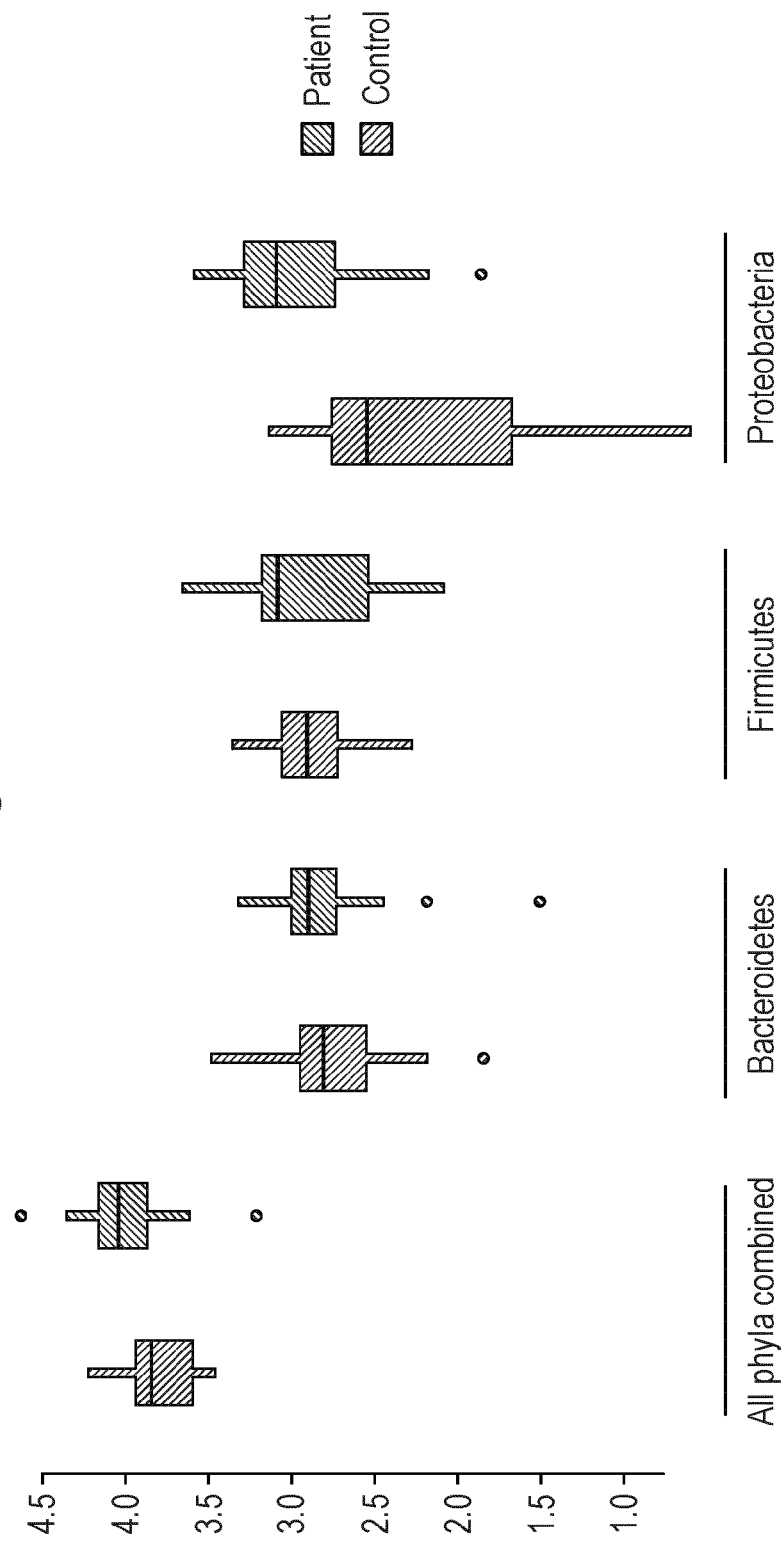
FIG. 5 shows boxplot comparisons of within-sample diversity as calculated by Shannon index (all phyla combined and per phylum) for diverticulitis patients and control subjects for the experiment as described in Example 2.

While diversity of the phyla Bacteroidetes or Firmicutes did not differ between patients and controls, the Shannon index indicated that the diversity of the Proteobacteria phylum was significantly higher in patients compared to controls (2.6 (IQR 1.07) and 3.2 (IQR 0.5) for controls and patients respectively; p<0.00002, Mann-Whitney U-test), which also affected the difference in diversity measured when considering all phyla together (3.9 (IQR 0.3) and 4.1 (IQR 0.3) for controls and patients respectively; p<0.002, Mann-Whitney U-test) (FIG. 5).

Figure 6:
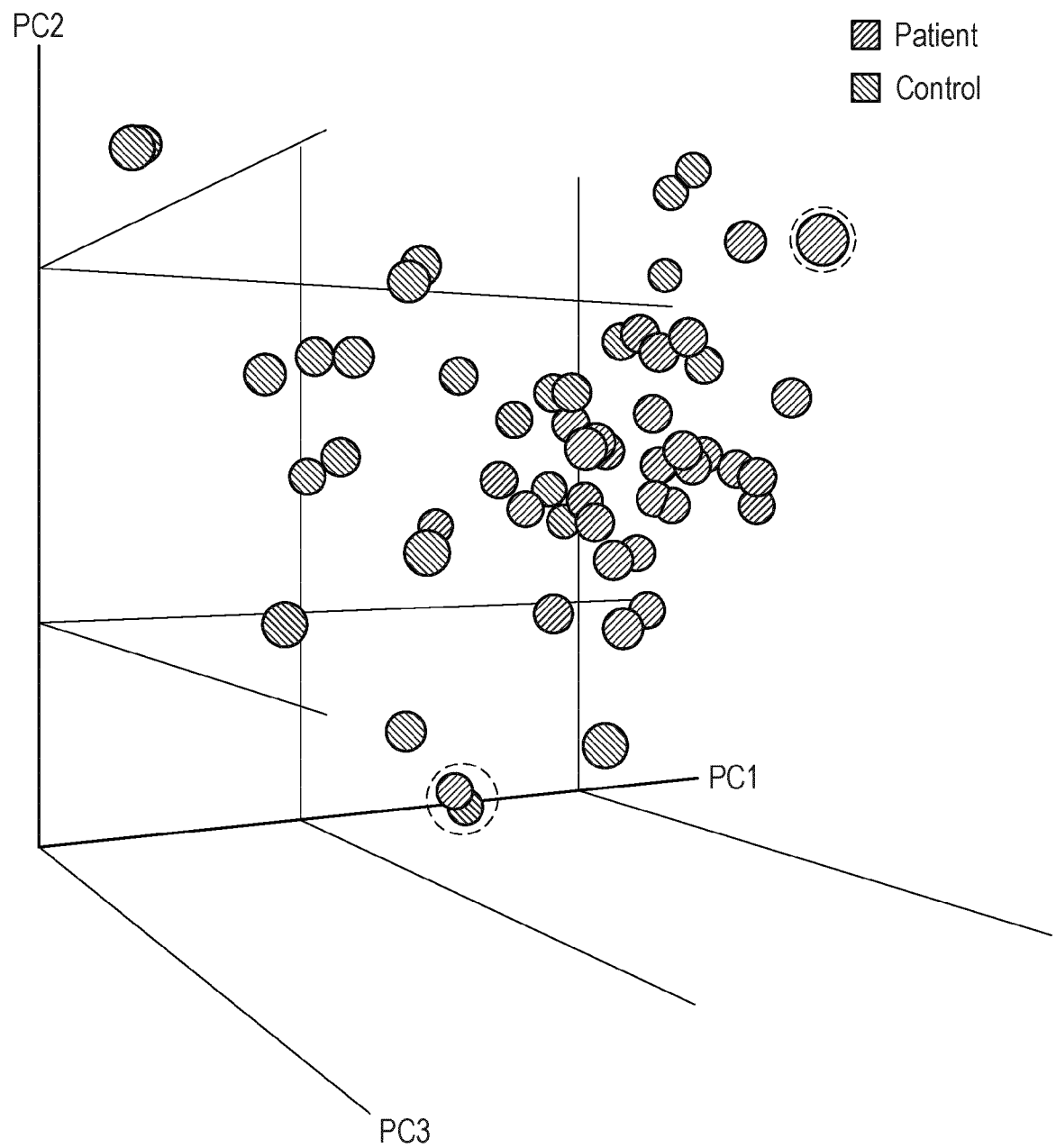
FIG. 6 shows a Principle Coordinate Analysis (PCoA) scatterplot to express between-sample diversity and displays clustering of diverticulitis patients separate from control subjects for the phylum Proteobacteria as explained in Example 2. Three wrongly classified samples are encircled.

Differences in overall bacterial community composition were assessed using cosine distances between samples. PCoA did not segregate diverticulitis patients and controls into different groups for the phyla Bacteroidetes and Firmicutes. However, patients could be clustered separately from controls in a 3-dimensional space based on their Proteobacteria profiles (FIG. 6).

Discriminative Ability of PLS-DA

Figure 7:
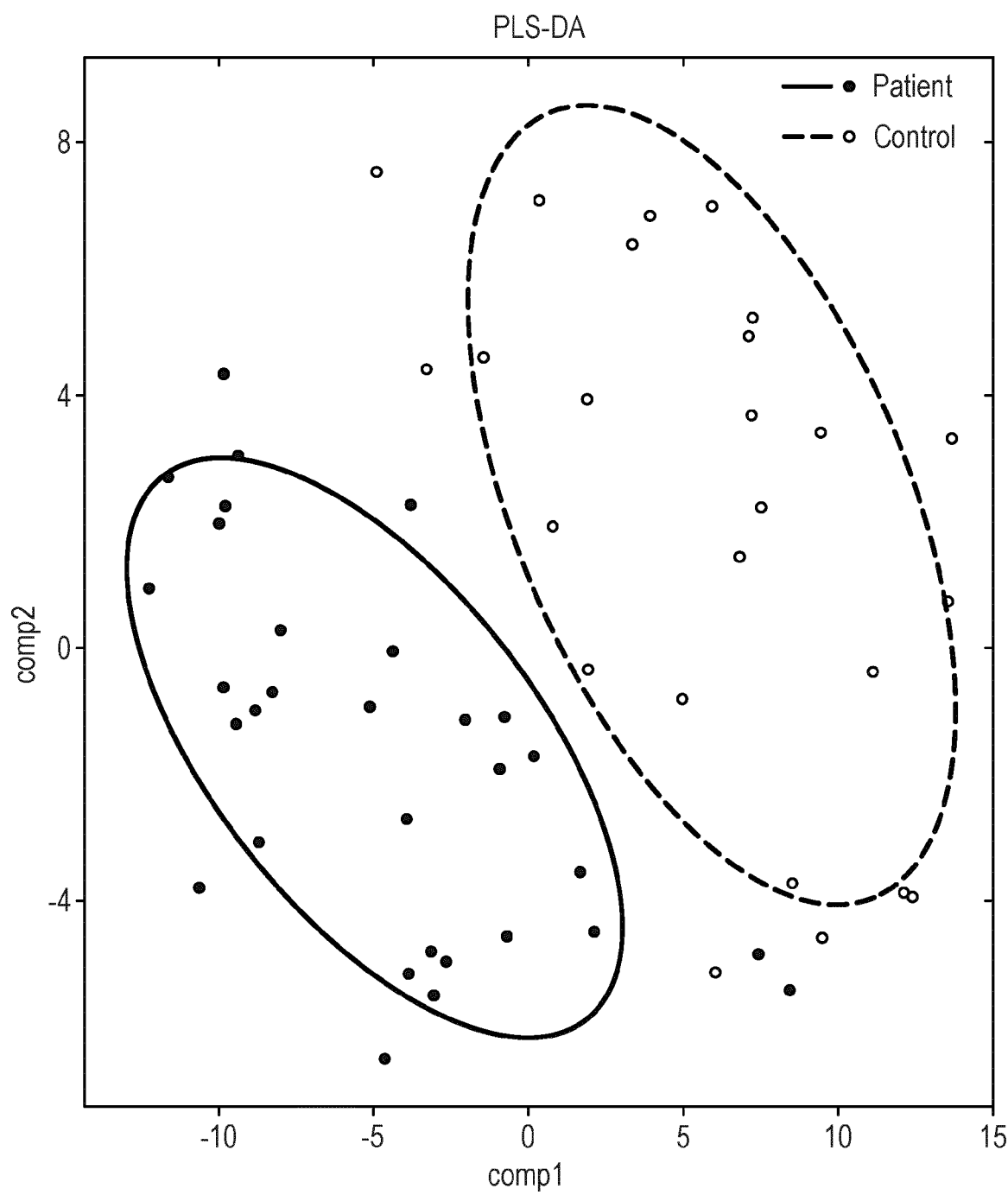
FIG. 7 shows the partial least square-discriminant analysis (PLS-DA) scores plot for the phylum Proteobacteria as explained in Example 2.

The use of an unsupervised approach for classification (PCoA) already demonstrated diagnostic potential of Proteobacteria profiles in predicting the health status of a given patient. This potential was born out in a supervised analysis, using PLS-DA known to be suitable for high-dimensional data (Rajilić-Stojanović et al. 2011. Gastroenterology 141: 1792-801; Pérez-Enciso et al. 2003. Hum Genet 112:581-92; Nguyen et al. 2002. Bioinformatics 18:39-50). The PLS-DA model used 268 OTUs, representing the 25% most variable OTUs, as predictors and the clinical status of the samples (i.e. diverticulitis: yes or no) as the response variable. In order to quantify the discriminative ability of the model we first considered the full datasets (three individual phylum datasets, and one composed of all phyla). Taking the Bacteroidetes or Firmicutes data as input resulted in low predictive accuracy rates (55% and 53% for Bacteroidetes and Firmicutes, respectively; data not shown). Taking the Proteobacteria data as input resulted in a predictive accuracy rate of 95% (FIG. 7). Three out of 56 samples were misclassified: one control and two patients, whose samples are the encircled ones in the PCoA scatterplot (FIG. 6). Resulting specificity was thus calculated to be 96% with a sensitivity of 94%. Taking the combined dataset, composed of all three phyla, as input resulted in an accuracy rate of 96% with two misclassified controls, corresponding to a specificity of 92% and 100% sensitivity. The misclassified controls were two subjects with diverticulosis. The most discriminative OTUs were found to derive largely from the family Enterobacteriaceae (Table 1).

TABLE 1

Most discriminative OTUs based on a Variable Importance for Projection value >1.2

| Species | Family |
| --- | --- |
| E. coli | Enterobacteriaceae |
| K. pneumoniae | Enterobacteriaceae |
| Enterobacter aerogenes | Enterobacteriaceae |
| S. marcescens | Enterobacteriaceae |
| Klebsiella variicola | Enterobacteriaceae |
| Providencia stuartii | Enterobacteriaceae |
| Desulfovibrio sp. | Desulfovibrionaceae |
| Xanthomonas | Xanthomonadaceae |
| Stenotrophomonas | Xanthomonadaceae |
| Pseudomonas aeruginosa | Pseudomonadaceae |
| Burkholderia sp. | Burkholderiaceae |
| Aggregatibacter actinomycetemcomitans | Pasteurellaceae |
| Unknown Proteobacteria species* | Unknown |

*11 types of unknown Proteobacteria species were identified.

Prediction of Diverticulitis Using the PLS-DA Model

Figure 8A:
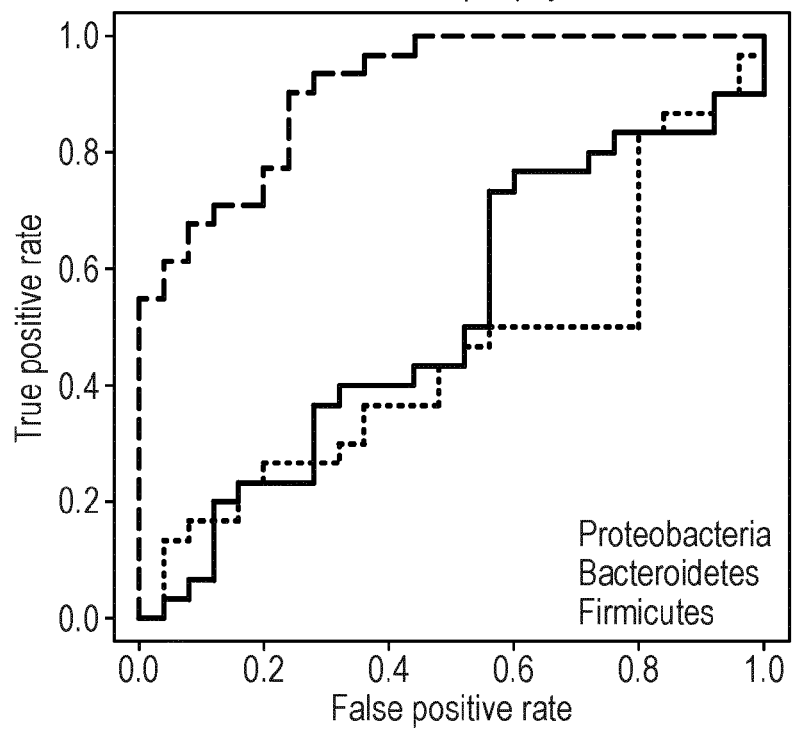
FIG. 8 shows ROC curves summarizing the predictive power of the PLS-DA model as described in Example 2 for clinical status per phylum (A) and for all phyla combined (B).
Figure 8B:
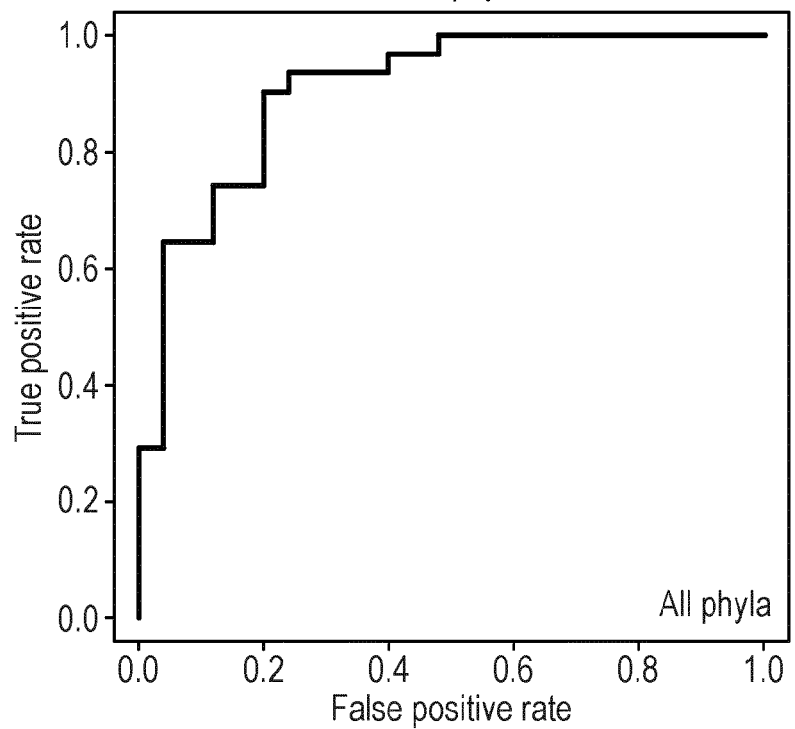

The predictive ability of the model was assessed by cross-validation. The dataset was randomly divided into 10 subsets, such that in each iteration one subset was chosen to serve as a test set. The prediction results from all iterations were then pooled together and enabled us to estimate the performance of the model by means of predictive power. Taking account of the Bacteroidetes or the Firmicutes phylum only resulted in a low predictive accuracy. For both the Bacteroidetes and the Firmicutes the cross-validated accuracy rate was 51%. Considering only the Proteobacteria, we reached a cross-validated accuracy rate of 80%. Six controls and five patients were wrongly classified, which resulted in a specificity of 76% and a sensitivity of 84%. When we combined the three phyla, we could reach a diagnostic accuracy rate of 84% (spec=80%; sens=87%). FIG. 8 summarizes the predictive power of the PLS-DA model by means of ROC curves.

The results of this study indicate that the fecal microbiota diversity of patients with a first episode of acute uncomplicated left-sided diverticulitis differs significantly from control subjects from a general gastroenterological practice, with the Proteobacteria phylum defining this difference. Furthermore, predictive diagnostics based on complex microbiota data seems feasible for diagnosing diverticulitis, with a diagnostic accuracy rate of 84%. The most discriminative species derived from the family Enterobacteriaceae.

Several studies have identified characteristics of the intestinal microbiota that may be associated with disease, but clinical diagnostic tools based on microbiome analysis still need to be developed. Whereas most studies into microbiota composition in health and disease identified correlations, here we demonstrate an approach in which microbiota composition may be used as a clinical predictor. By employing a supervised algorithm in combination with cross-validation, we show how microbiota analysis may move towards prediction instead of correlation. PLS regression provides a dimension reduction strategy in situations where a set of response variables need to be related to a set of predictor variables. It is considered a supervised learning method since it uses the dependent (clinical status in this study) as well as the independent variables (OTUs) to construct variable selection and importance ranking. PLS-DA refers to the particular case where the response variable is a set of binary variables describing the categories of a categorical variable, e.g. disease states. This model is commonly used in the field of chemometrics and in the analysis of microarray expression data, as it is especially suited to deal with a much larger number of predictors than observations and with multi-colinearity. In this study we encountered similar challenges; the number of OTUs is much larger than the number of samples and some of them are highly correlated. Due to the properties mentioned above, we found this approach also very appropriate to apply to IS-pro data. The VIP criterion was previously used in PLS-DA microarray analyses to assess which genes were useful to discriminate between different groups.

Specific shifts in the phylum Proteobacteria—other than general measures like diversity—have not been found to be associated with disease before. This might be caused by the fact that Proteobacteria generally have a low relative abundance in the intestinal microbiota. Because almost all current approaches to analyze the intestinal microbiota use universal bacterial amplification as a starting point, low abundant phyla such as the Proteobacteria remain relatively under explored as other, more prevalent taxa will dominate the PCR reaction and following analyses. In contrast, the IS-pro molecular technique comprises two separate phylum-specific PCR reactions: one for the amplification of Bacteroidetes/Firmicutes and another for the specific amplification of Proteobacteria. While the separation of the different phyla in two PCRs prevents us from addressing all three phyla together when presenting their relative abundances—consequently hampering direct comparisons of abundances—it does allow us to zoom in and analyze the Proteobacterial community composition in-depth.

Brook et al. retrospectively studied the aerobic and anaerobic microbiology of 110 specimens from the peritoneal cavity after intestinal perforation and in 22 specimens from abdominal abscesses of patients with complicated diverticulitis [Brook I, Frazier E H. 2000. J Med Microbiol 49:827-30] With conventional culture techniques they identified *E. coli* and *Streptococcus* spp as the predominant aerobic and facultative bacteria and the most frequently isolated anaerobes were *Bacteroides* spp (*B. fragilis* group), *Peptostreptococcus, Clostridium* and *Fusobacterium* spp. The only study up to date with PCR based sequencing of the microbiota in diverticulitis patients was conducted by Gueimonde et al. [Gueimonde M, Ouwehand A, Huhtinen H, et al. 2007. World J Gastroenterol 13:3985-9] They identified a significant higher occurrence of *Bifidobacterium longum* and *Bifidobacterium animalis* in patients with diverticulitis, and their overall conclusion was that aberrancies in mucosa associated microbiota are present in different intestinal diseases. However, in their study only nine diverticulitis patients were included. Resected mucosal samples were compared with those of 21 colon cancer patients and four inflammatory bowel disease patients, but no healthy controls. Surprisingly, they looked only at the genus *Bifidobacterium* and did not analyze the entire profile; they stated they used the bifidobacterial microbiota as an indicator of alterations in the mucosal colonisation pattern. The bifidobacterial microbiota however, is known to constitute only a small fraction of the intestinal microbial composition in adults.

Currently, antibiotics are often used in the conservative treatment of uncomplicated diverticulitis despite the lack of sound evidence. Cyclic administration of rifaximin has been proven to be effective in reducing symptoms and complications and possibly prevents recurrence in patients after complicated diverticulitis. Relatively new therapies, such as probiotic therapy, are proposed as well for the management of diverticular disease (DD). Indeed, a few small open label studies already show promising results. Considering that antibiotic and probiotic treatments are regularly prescribed to DD patients, it is striking that relatively few studies have been performed to improve our understanding of the composition of the colonic microbiota. The pathophysiology of diverticulitis was assumed to be clear and well understood but actually astonishingly little is known about causal factors for this disease. Our understanding of the effect of changes in microbiota abundance, diversity and composition is limited. Our study therefore, is a first step in further elucidating the etiopathogenesis of diverticular disease and its inflammatory complications.

Since a clinical diagnosis of diverticulitis can not be made with a high certainty without imaging, it seems appropriate to evaluate a test intended for making a specific clinical diagnosis against a patient group with variable clinical presentation. By taking a cross-section of patients in a general gastroenterological practice instead of a healthy control group, the specificity of the prediction becomes more meaningful.

This study has some limitations. First, we have data on only a small study group. As a result we are not able to estimate and optimize predictive ability robustly. The performance of a predictive tool is prone to be overestimated in its own study cohort. For diagnostics by microbiome to be applied in daily practice a study like this one should be externally validated and followed by a larger study to confirm results and calculate sensitivity and specificity more robustly. Second, as a consequence of a small sample size, we were not able to firmly compare diverticulitis patients with subjects with diverticulosis. It has been hypothesized that DD patients have a changed colonic microbiome. From an etiopathogenetic point of view, it would be informative to know to what extent the microbiome in diverticulosis resembles the microbiome in diverticulitis or health. Indeed, the two controls that were misclassified, were subjects with diverticulosis. This seems to underline a shift in microbiota related to diverticular disease. The present tool may reveal a gradual shift in microbiota composition from patients with diverticulosis towards diverticulitis. In the present study, species identification was done by in-silico comparison of fragment lengths. This technique generally gives consistent results.

The present study demonstrates that the diagnosis of diverticulitis can be done by microbiome analysis with relatively good accuracy. More generally, this study illustrates a proof of concept of how diagnostics based on complex microbiota data in a broader sense may be applied. Thus, the fecal microbiota can be used as diagnostic tool for diverticulitis, with patient stratification directing a personalized treatment strategy, whether or not to prescribe antibiotics, the type of antibiotic, and even to monitor disease course. Clinical application as a diagnostic tool also reduces the need for imaging to diagnose diverticulitis.

Example 3. A Convenient Method for Reproducible Sampling of the Intestinal Microbiota in a Clinical Setting This study was set up as a descriptive study to compare rectal swabs for sampling of the intestinal microbiota with sampling of feces specimens and mucosal biopsies. Two rounds of investigations were held. In the first, patients who underwent an elective colonoscopy were asked to bring in feces one week before the procedure, and rectal swabs and biopsies were taken during the procedure. Because colonoscopy involves extensive intestinal preparation, in a second round patients with inflammatory bowel disease were asked to sample feces and to obtain one rectal swab at home; a second rectal swab was obtained on the day they brought in the feces (FIG. 9).

Subjects were included that either underwent an elective colonoscopy between February and June 2011 (for sets of rectal swabs, mucosal biopsies and fecal samples in prepped patients) or presented for commonly scheduled control at the inflammatory bowel disease (IBD) outpatient clinic in October 2012 (for sets of rectal swabs and feces in unprepped patients). In the first group, the only exclusion criterion was a contraindication for taking mucosal biopsies.

Samples

Rectal swabs were taken with FLOQSwabs® 552C (Copan, Calif., USA), which were inserted into the anal canal, beyond the anal verge (±3 cm). All patients who underwent colonoscopy were prepped according to a standardized protocol with a laxative preparation consisting of high-volume polyethylene glycol (PEG) solution (Kleanprep®, Helsinn, Lugano, Switzerland). Mucosal biopsy specimens were collected with a flexible video endoscope (Olympus GmbH, Hamburg, Germany) and a flexible biopsy forceps (Wilson-Cook; European Endoscopy Group, Fujinon Medical Holland, Veenendaal, The Netherlands). Mucosal biopsy specimens were harvested from sigmoid colon at 20-30 cm from the anal verge. Per subject, one mucosal sample was washed twice in 500 µl PBS (pH 7) before snap-freezing in liquid nitrogen and a second sample was deposited in a container filled with 500 µl PBS and snap frozen in liquid nitrogen. All samples were stored at −20° C. In the colonoscopy group, rectal swabs were collected at the time of colonoscopy, just prior to the endoscopic procedure. Two rectal swabs were deposited in a container with 500 µl Reduced Transport Fluid (RTF) buffer 9 and kept at room temperature for 2 hours prior to storage at −20° C. One swab was immediately snap frozen in liquid nitrogen (with no RTF buffer).

In the IBD outpatient group, two rectal swabs were gathered. One was taken by the patients themselves, at home, one day prior to presentation and stored in RTF buffer at −20° C. The other was taken at the outpatient clinic and stored in the same fashion. Both swabs were stored in a container with 500 µl RTF buffer at −20° C.

In both the colonoscopy and the IBD outpatient group, fecal samples were gathered within five days before presentation at the outpatient clinic for endoscopy or routine control. Samples were gathered in sterile containers and were stored at −20° C. within 2 h after collection and kept frozen until further analysis.

DNA Isolation

DNA was isolated from feces and mucosal biopsies as described in Budding et al. 2010 (cited above). In short, for mucosal samples, the first step consisted of lysis of tissue and bacteria with the QIAAMP® DNA mini Kit (Qiagen, Hilden, Germany) followed by DNA extraction with the NucliSENS® easyMag® automated DNA isolation machine (Biomérieux, Marcy l'Etoile, France). For fecal samples, 100-400 mg of feces was used as input for the fecal DNA extraction protocol of the easyMag® machine as described by the manufacturer. For DNA isolation from swabs, one ml of NucliSENS® lysisbuffer, containing guanidine thiocyanate, was added to each vial containing a swab tip and the mixture was shaken at 1400 rpm (Thermomixer® comfort, Eppendorf, Hamburg, Germany) for five minutes. For a subset of 14 snap frozen swabs, an additional bead-beating step was evaluated. For these swabs, after five minutes of shaking at 1400 rpm, the mixture was divided into two parts. To one part, approximately 100 µg of Zirconia 0.1 silica beads were added and bead-beating was performed for 60 seconds. Afterwards, all samples were centrifuged for four minutes at 12.000 g and added to the easyMag® container. DNA extraction was performed on the easyMag® machine with the Specific A protocol as described by the manufacturer.

IS-Profiling of the Intestinal Microbiota

The intestinal microbiota analysis was performed by IS-pro as described in Budding et al. 2010. IS-pro involves bacterial species differentiation by the length of the 16S-23S rDNA interspace region with taxonomic classification by phylum-specific fluorescent labelling of PCR primers.

Amplification of IS Regions

Five primers are used for amplification of IS regions. Two fluorescently labelled forward primers are phylum-specific, for the 16S rDNA region: one FAM-labeled primer, specific for Firmicutes, Actinobacteria, Fusobacteria and Verrucomicrobia and one HEX-labelled primer specific for Bacteroidetes. Three unlabeled reverse primers are specific for the 23S rDNA region. The combination of these primers provides very broad coverage for Firmicutes, Actinobacteria, and Bacteroidetes. The primers are used in a multiplex PCR, which amplifies the 16S-23S IS region. The length of this IS region and its PCR product is species-specific.

The fluorescent label provides identification of all fragments at the phylum level.

Amplifications were carried out on a GeneAmp® PCR system 9700 (Applied Biosystems, Foster City, Calif.).

Cycling conditions for PCR were 72° C. for 2 min; 35 cycles of 94° C. for 30 s, 56° C. for 45 s, and 72° C. for 1 min; and a final extension at 72° C. for 5 min. Each PCR mixture, with a final volume of 25 µl, contained 10 µl of buffered DNA, 1x superTaq buffer (SphaeroQ, Gorinchem, the Netherlands), 200 µM deoxynucleoside triphosphate, 0.04% BSA, 1 U of superTaq, and 0.13 µM of each of the 5 primers.

IS-Fragment Analysis

Figure 10:
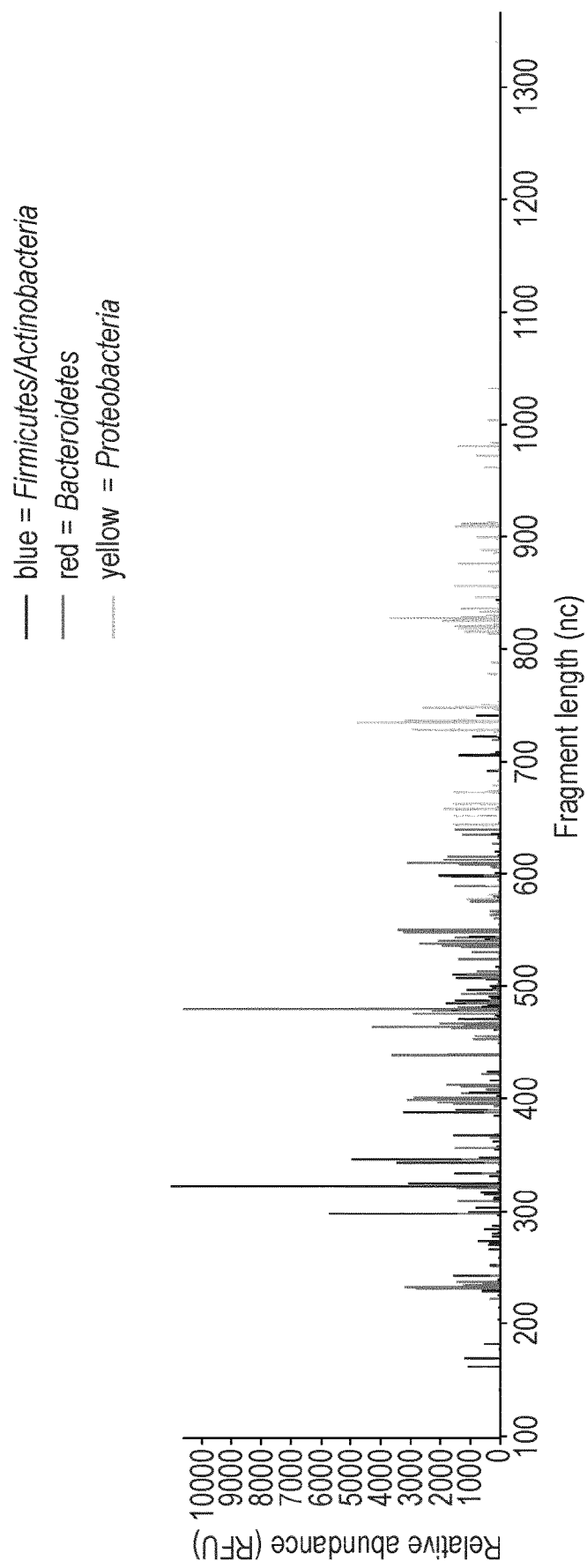
FIG. 10 shows a sample IS-profile in the context of Example 3. The x-axis represents IS fragment length, the y-axis represents relative abundance of fragments in relative fluorescent units (RFU). Colors of fragments correspond to bacterial phyla. Blue peaks represent Firmicutes/Actinobacteria, red peaks represent Bacteroidetes and yellow peaks represent Proteobacteria. Each peak may be regarded as an operational taxonomic unit (OTU).

After PCR, 5 µl of PCR product was mixed with 19.8 µl formamide and 0.2 µl Mapmaker 1000 ROX-labeled size marker (BioVentures, Murfreesboro, Tenn., USA). DNA fragment analysis was performed on an ABI Prism 3130XL Genetic Analyzer (Applied Biosystems). Results are presented as color-labeled peak profiles (FIG. 10). These peaks can be regarded as operational taxonomical units (OTU's) and we will refer to them as such henceforth in the text. All data were further analyzed with the Spotfire® software package (TIBCO, Palo Alto, Calif., USA).

Statistical Analysis

All statistical analyses were performed described previously 10. Comparisons between all samples (swab vs duplicate swab, swab vs snap frozen swab, swab vs feces, swab vs mucosal biopsy and feces vs mucosal biopsy) were made by calculating squared correlation coefficients for all possible pairs of samples. When duplicate swabs stored in RTF from the colonoscopy group were compared to other samples, averaged profiles of the duplicate swabs stored in RTF were used.

Comparisons were grouped in intra and inter individual comparisons, the former group comprising all comparisons between samples from the same individual, the latter group comprising all other comparisons. Median and inter quartile range (IQR) were calculated for each comparison group.

Results

Study Population

A total of 38 subjects was included in the colonoscopy group, 23 male and fifteen female. The indications for colonoscopy were suspected benign neoplasm (8), diverticulosis (6), screening for familial tumours (5), IBD (5) and general gastrointestinal complaints (7). Not all sample types could be harvested from all subjects and in some samples the PCR reaction was inhibited. The total number of samples obtained was: 35 snap frozen rectal swabs, 37 sets of rectal swabs in RTF, 33 dry mucosal biopsies, 35 mucosal biopsies in sodium chloride 0.9% and 19 fecal samples.

Ten subjects were included in the IBD outpatient group, two male (both with ulcerative colitis) and eight female (four with ulcerative colitis, four with Crohn's disease). Two subjects presented with active disease, eight with disease in remission. The total number of samples was: ten swabs and ten fecal samples taken at home by the patients themselves and ten swabs taken at the outpatient clinic by their physician.

Effect of Bead-Beating for DNA Isolation

As it has been described that DNA isolation protocols for fecal samples that include bead-beating give higher DNA yields of certain groups of bacteria (Salonen et al. 2010 J Microbiol Methods 81:127-134), we compared this procedure to automated DNA isolation for swab samples. With a mixed effects model, accounting for both fixed and random effects, we found bead-beating to have a significant negative impact on DNA recovery from Bacteroidetes: Bacteroidetes peaks in DNA isolated without a bead beating step were on average 1.85 times higher than the equivalent peaks in DNA isolated with a bead beating step (p=0.015). For Firmicutes there was also a trend towards a negative impact of bead beating. Firmicutes peaks from DNA without bead beating were on average 1.45 times higher than equivalent peaks generated from DNA with a bead beating step (p=0.051) (data not shown).

Effect of Storage and Processing of Rectal Swabs

To evaluate the effect of a non-stringent sample storage protocol, where storage of samples at room temperature for two hours was allowed, we compared microbiota profiles of snap-frozen rectal swabs to profiles of rectal swabs that had been stored in RTF for two hours before freezing at −20° C. As storage conditions may affect Gram positive and Gram negative bacteria differently, we analyzed data separately for Firmicutes and Bacteroidetes. Correlations were calculated for profiles derived from snap frozen swab samples versus the averaged profiles of duplicate swab samples stored in RTF at room temperatures before freezing.

Figure 11A:
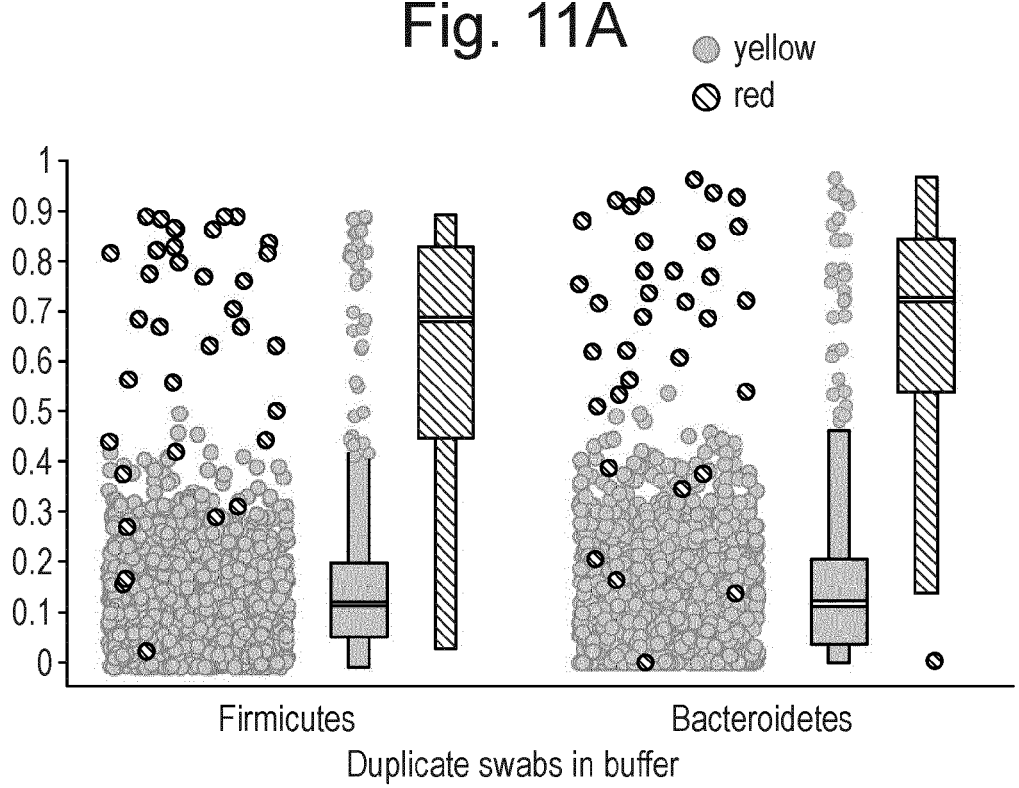
FIG. 11 shows various comparisons of microbiota profiles expressed as R squared in the context of Example 3. All comparisons were done separately for Firmicutes/Actinobacteria (left) and Bacteroidetes (right). Figures show comparisons of all profiles. Red dots represent comparisons of samples of the same subject (intra-subject correlation). Yellow box plots are based on all correlations, red box plot on intra-subject correlations only. A: Duplicate swab profiles stored in RTF buffer. B: Swab stored in RTF buffer vs. snap frozen swabs. C: Swabs stored in buffer vs. mucosal biopsies. D: Swabs stored in buffer vs. fecal samples. E: fecal samples vs. mucosal biopsies.
Figure 11B:
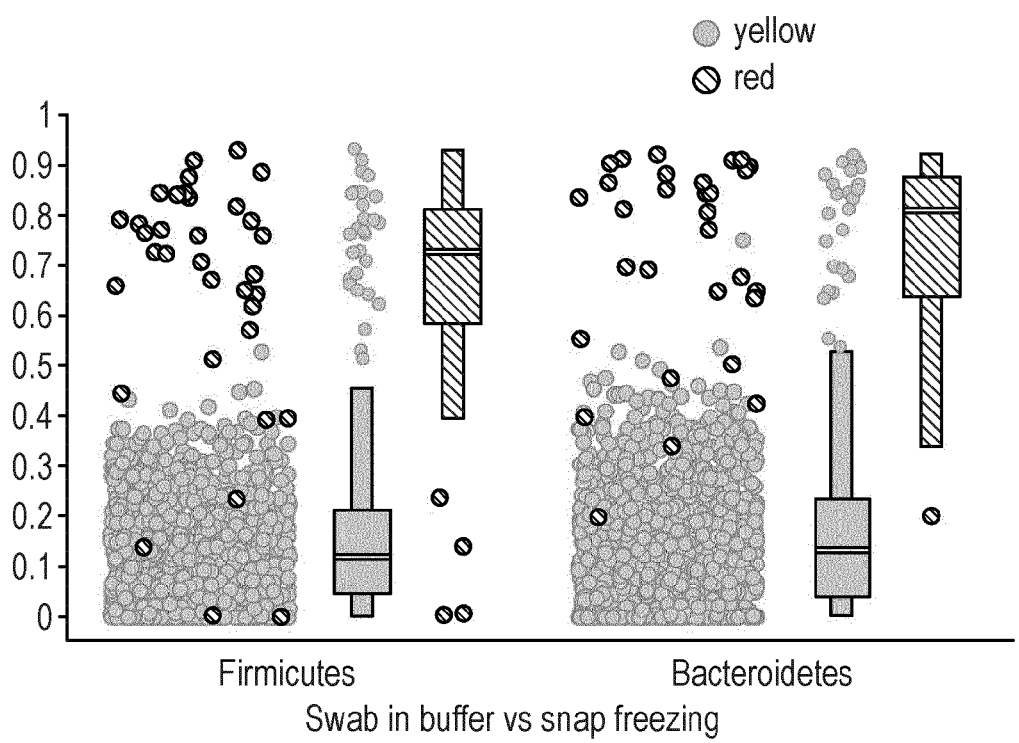

For both Firmicutes and Bacteroidetes, intra-individual comparisons showed high similarities as measured by a high median $R^2$. Inter individual comparisons were low, as was expected (FIG. 11B). For all measured values in the above and subsequent sections, reference is made to Table 2.

TABLE 2

Median R squared and Inter Quartile Range (IQR) values for all comparisons. IQR values are indicated in brackets. Rows A and B indicate either intra-individual comparisons (A) or inter-individual comparisons (B).

| Comparator 1 | Comparator 2 | Firmicutes | Bacteroidetes |
|---|---|---|---|
| Swab | Snap frozen swab | A 0.73 (0.23) | 0.81 (0.24) |
|  |  | B 0.12 (0.16) | 0.13 (0.20) |
|  | Duplicate swab | A 0.70 (0.38) | 0.72 (0.31) |
|  |  | B 0.13 (0.15) | 0.12 (0.17) |
|  | Swab at home | A 0.55 (0.26) | 0.82 (0.23) |
|  |  | B 0.14 (0.03) | 0.05 (0.14) |
|  | Faeces | A 0.17 (0.18) | 0.36 (0.35) |
|  |  | B 0.10 (0.12) | 0.36 (0.20) |
|  | Mucosal biopsy | A 0.15 (0.21) | 0.32 (0.44) |
|  |  | B 0.10 (0.11) | 0.13 (0.19) |
| Swab at home | Faeces | A 0.23 (0.52) | 0.75 (0.39) |
|  |  | B 0.10 (0.12) | 0.05 (0.20) |
| Faeces | Mucosal biopsy | A 0.12 (0.28) | 0.33 (0.35) |
|  |  | B 0.12 (0.14) | 0.13 (0.16) |
|  | Swab at home | A 0.23 (0.52) | 0.75 (0.39) |
|  |  | B 0.10 (0.12) | 0.05 (0.20) |

Reproducibility

To test the reproducibility of the swabbing procedure, we compared duplicate swabs obtained from the same patients (n=37). These duplicate swabs were stored in RTF buffer at room temperature for 2 hours. Profiles were compared pairwise with Pearson correlation and results were analyzed separately for Firmicutes and Bacteroidetes. In this analysis too, intra-subject correlations were high for both Firmicutes and Bacteroidetes, whereas inter individual correlations were low (FIG. 11A). These data indicate that reproducibility of rectal swabs within the same patients was very good.

To test whether self-sampling by patients at home would yield comparable results to swabs taken in a standardized fashion at the outpatient clinic, we compared these in ten individuals. Again, profiles were compared pairwise and results were analyzed separately for Firmicutes and Bacteroidetes. This analysis too showed high intra-subject correlations and low inter-subject correlations (FIG. 11A). This showed that self-collected swabs by patients at home were highly comparable to clinically collected swabs when stored in the same fashion.

Comparison of Different Sample Types

Figure 11C:
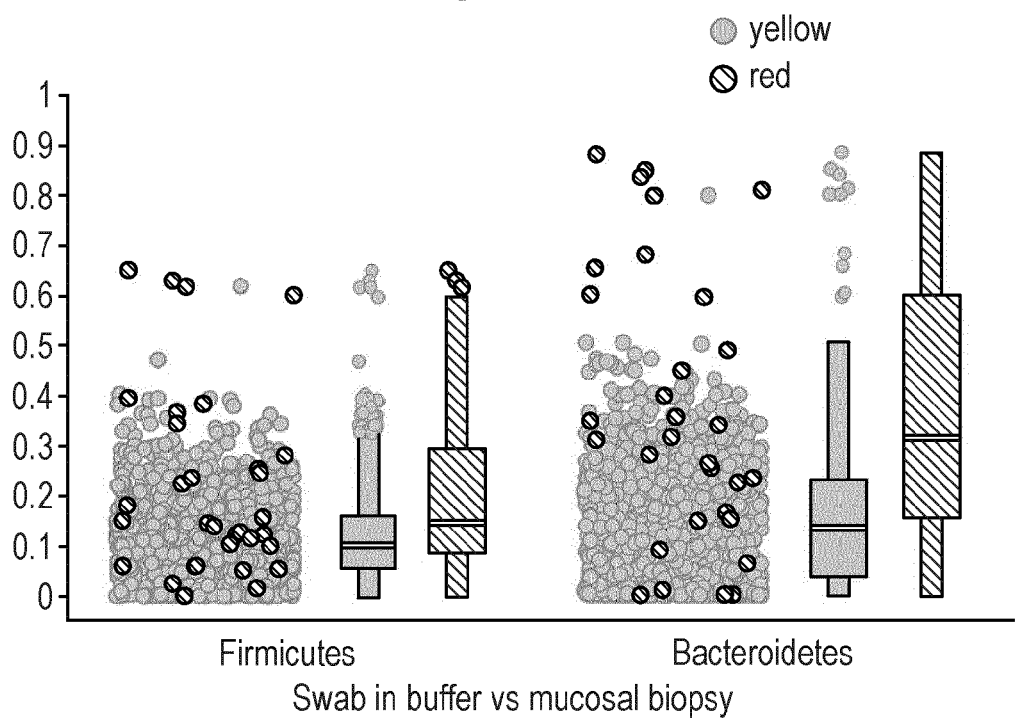
Figure 11D:
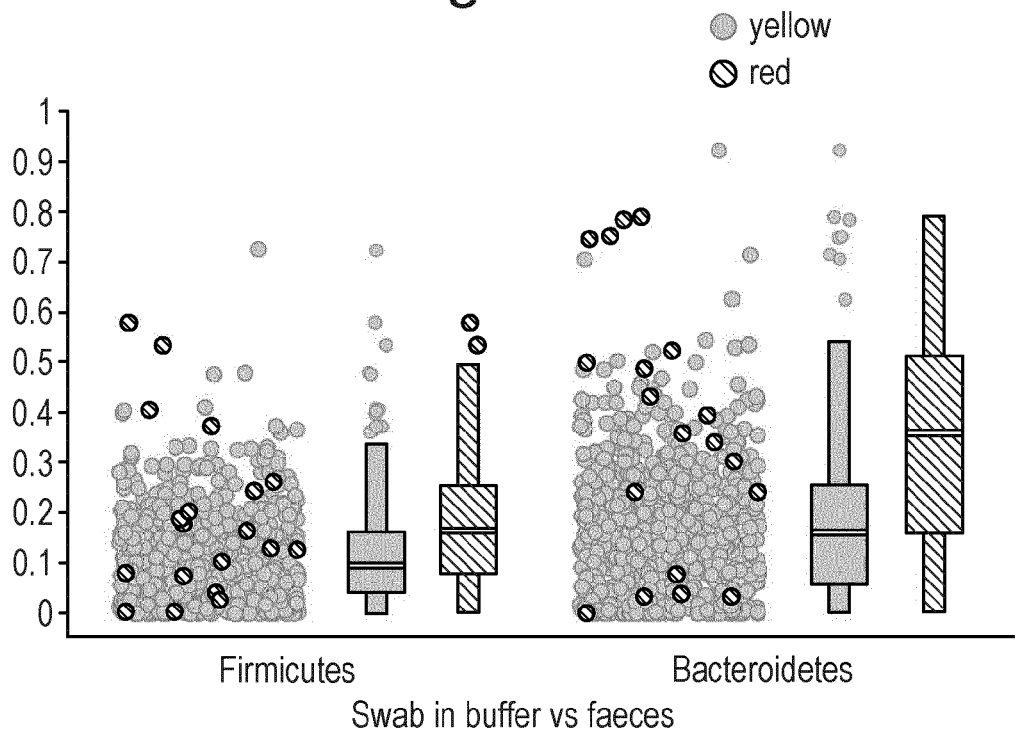
Figure 12A:
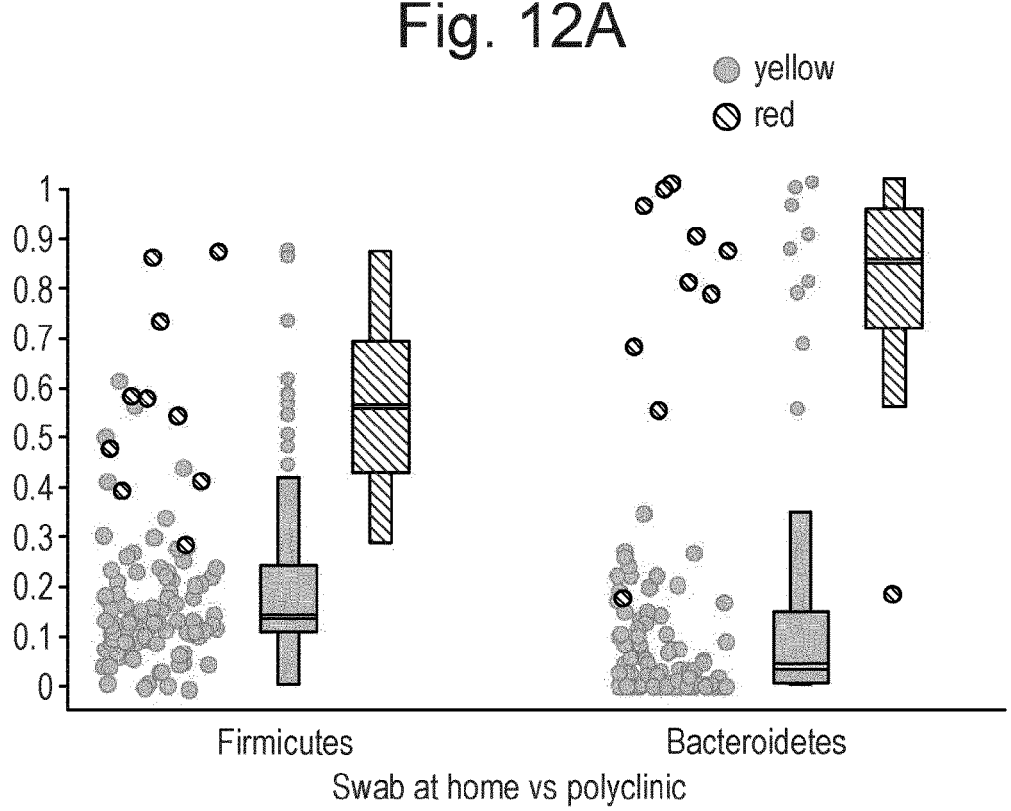
FIG. 12 shows comparisons of microbiota profiles in the IBD polyclinic group expressed as R squared in the context of Example 3. All comparisons have been done separately for Firmicutes/Actinobacteria (left) and Bacteroidetes (right). Figures show comparisons of all profiles. Red dots represent comparisons of samples of the same subject (intra-subject correlation). Yellow box plots are based on all correlations, red box plots on intra-subject correlations only. A: Swabs taken by patients at home vs. swabs taken by the physician at the polyclinic. B: Swabs vs. fecal samples
Figure 12B:
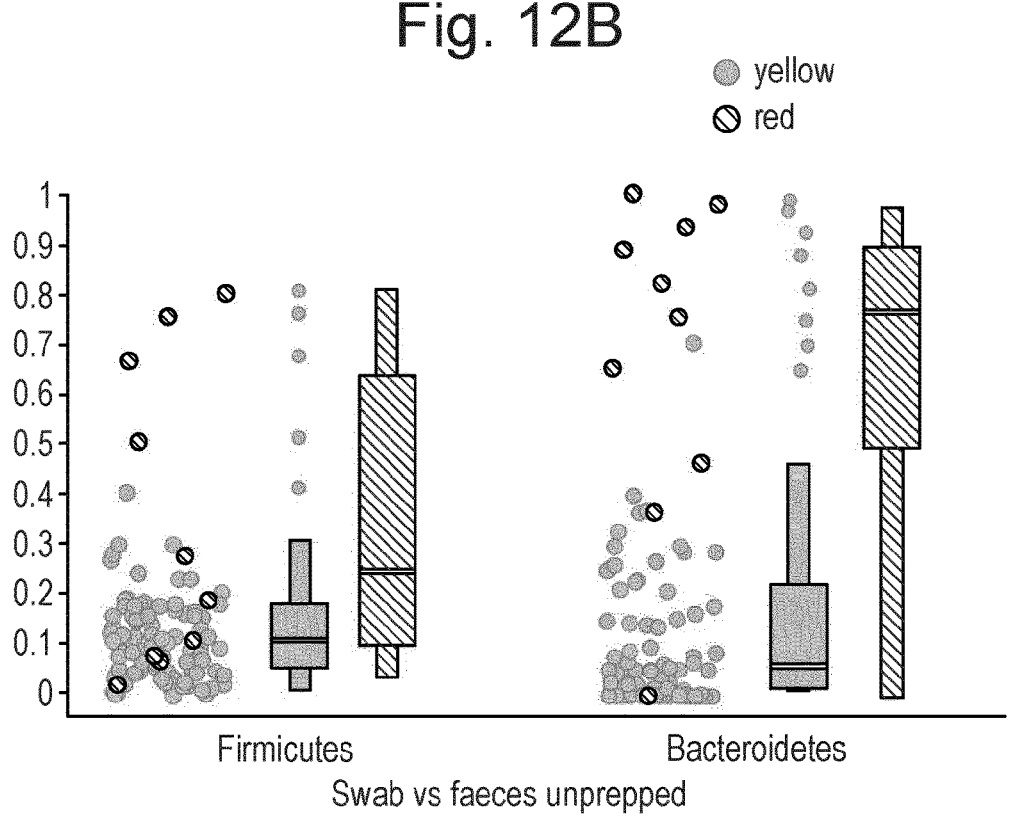

Finally, rectal swabs, fecal samples and mucosal biopsies were compared to each other. First, rectal swab microbiota profiles were compared to fecal microbiota profiles in nineteen subjects of the colonoscopy group and in all ten subjects of the IBD outpatient group. In the colonoscopy group, correlations between swab and fecal profiles were generally low. Bacteroidetes generally had a slightly higher correlation than Firmicutes (FIG. 11D). In the IBD outpatient group, all correlations were markedly higher, especially for the Bacteroidetes, which had a median value of $R^2$ similar to that found for duplicate swab profiles. As expected, inter subject correlations were low in both groups. These data show that fecal profiles resemble swab profiles, but not in people who have undergone bowel prepping (FIG. 12B).

Next, we compared swab samples to mucosal biopsy samples taken by colonoscopy in 32 subjects. This comparison showed that correlation of swab profiles to mucosal profiles was low, similar to the correlation of swab samples to fecal samples in this prepped patient group. Bacteroidetes profiles showed a higher similarity than Firmicutes profiles (FIG. 11C).

Finally, as we found rectal swab microbiota profiles to be distinct from mucosal and fecal microbiota profiles in the colonoscopy group, we were interested in the similarity between fecal microbiota and mucosal microbiota.

Figure 11E:
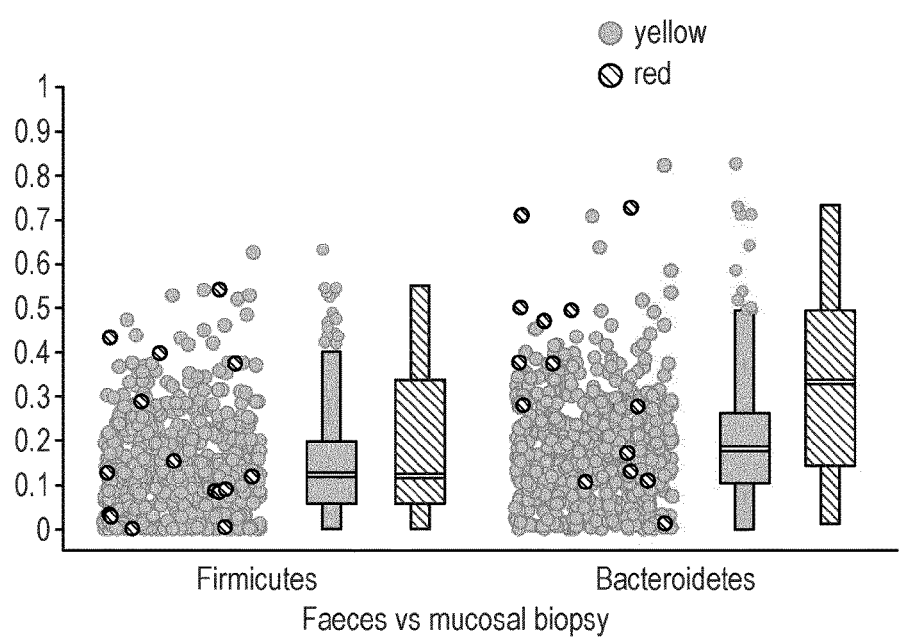

To compare these we used the same analysis as above. We found that correlations between fecal samples and mucosal biopsies were comparably low as the correlations of swab samples to both these sample types. In this comparison too, a higher correlation was found for Bacteroidetes than for Firmicutes (FIG. 11E).

In this Example it is shown that rectal swabs can be conveniently taken and provided a good method to produce highly reproducible microbiota profiles which are similar to fecal sample profiles. It is therefore suggested that rectal swabs may be ideally suited for large scale studies and for routine clinical applications of microbiota profiling. Sampling of the intestinal microbiota by feces sampling or by rectal swabbing, without previous bowel preparation (without extensive bowel lavage is probably the preferred method if analyzing genuine, undisturbed microbiota in a subject (or patient). Rectal swabs are an attractive means of sampling the intestinal microbiota in a clinical setting because they do not have the drawbacks of feces collection and harvest of mucosal biopsies. Subjects do not necessarily need to collect samples themselves as is needed for fecal samples and they do not need to be prepped or undergo invasive procedures. The applicability of rectal swabs in clinical routine settings is highlighted by the fact that rectal swabs are already commonly used in clinical routine for detection of carriage of resistant microorganisms and can be taken at every visit.

It is further shown that short-term storage of rectal swabs in RTF buffer at room temperature had no impact on the composition of the microbiota, thus relaxing requirements for sample collection and storage and making the method applicable in almost any (clinical) setting. It is demonstrated herein that storage of rectal swabs at room temperature for 2 hours in a stabilizing buffer (RTF buffer), does not impact microbiota composition.

It was found that bead beating did not contribute to the DNA yield from rectal swabs. In contrast, bead beating diminished the yield of Bacteroidetes DNA. This was an unexpected, yet reproducible outcome in the context of what has been described for isolation of bacterial DNA from feces. For clinical routine, in which speed and easy implementation is essential, omission of bead-beating can be considered favorable.

It is further shown that swab profiles are indeed similar to feces profiles obtained from unprepped subjects, but decidedly distinct from feces profiles in prepped patients. In these prepped subjects, microbiota profiles in swab samples were also distinct from profiles in mucosal biopsies. Rectal swabs were taken just prior to colonic mucosal biopsies, both after prepping of the subject. The difference in composition between these samples thus seemed to represent a true difference in composition between the rectum/proctum, which was sampled by rectal swabs, and more proximal in the distal sigmoid colon, as sampled by sigmoidal mucosal biopsies.

It was found that rectal swabs were a convenient means of sampling the human gut microbiota. Swabs can be taken 'on demand', whenever a subject presents. The acquired samples resembled fecal microbiota and showed a highly reproducible profile, whether they are gathered at home by patients or by medical professionals in an outpatient setting.

Example 4. IS-Pro for Analysis and Diagnostics in Parodontitis

Parodontitis is an inflammation of the parodontium. It has long been known that bacteria play a causative role in this inflammatory process. In contrast to classic infection and inflammation, which is typically caused by a single causative organism, parodontitis is caused by a consortium of bacteria. The presence of the bacteria in this consortium alone may not cause harm, only in combination with other members of the consortium. The bacteria that may belong to this consortium is not a strictly defined set. Seven species have now convincingly been shown to be important players, but new organisms continue to be found that also play a role in the paropathogenic microbiota. Currently, most diagnostic tests to identify parodontitis are based on quantifying the presence of a defined number of bacteria from the paropathogenic consortium. Given the fact that the putative paropathogenic consortium has not been characterized in its entirety, it is likely that diagnostics tests that are not limited to a predefined set of microbes, may perform better in diagnosing parodontitis.

Here we evaluate the performance of the 16S-23S interspace (IS) based profiling technique IS-pro, for characterizing the population of all bacteria present in a microbial consortium in order to distinguish parodontitis from a healthy control group. We analyze data by classical statistical methods and by predictive modeling and compare results to qPCR on a defined set of seven defined members of the paropathogenic microbiota.

Materials and Methods

Design

This study was set up as a prospective cohort study, including patients with proven parodontitis and subjects with a proven healthy parodontium. Two different methods were compared in their ability to distinguish parodontitis patients from the healthy controls based on parodontal microbiota.

Study Population

Parodontitis patients and control subjects were grouped and the dental and periodontal health status of all subjects was evaluated using standard methods. Ten subjects were included in both the parodontitis and the control group.

Sampling Technique

Sampling sites were isolated with cotton rolls, supragingival plaque was carefully removed with curets and the sites were air dried. Subgingival plaque samples were obtained by inserting sterile paper points into the bottom of the sulcus or pocket. After several seconds, paper points were removed and deposited in a labeled sterile tube containing 1.5 ml Reduced Transport Fluid (RTF) and transported to the laboratory where they were stored at −20° C. until further processing.

DNA Isolation

DNA was isolated from paperpoints by DNA extraction with the NucliSENS® easyMag® automated DNA isolation machine (Biomérieux, Marcy l'Etoile, France). One ml of nucliSENS® lysisbuffer, containing guanidine thiocyanate, was added to each vial containing the paperpoints and the mixture was shaken at 1400 rpm (Thermomixer® comfort, Eppendorf, Hamburg, Germany) by RT for five minutes. Samples were added to the easyMag® container and DNA extraction was performed on the easyMag® machine with the Specific A protocol as described by the manufacturer.

Quantitative Real-Time PCR

The primer/probe sets and real-time PCR conditions were performed as described previously (Boutaga 2005). qPCR was specific for Aggregatibacteractinomycetemcomitans (AA), Treponemadenticola (TD), Fusobacteriumnucelatum (FN), Porphyromonasgingivalis (PG), Parvimonasmicra (PM), Prevotellaintermedia (PI) and Tannerella forsythia (TF). In short, 3 duplex and one monoplex real-time PCR was performed with total reaction volumes of 15 µl, covering all seven species mentioned above. Duplex PCRs consisted of the combinations AA/PI, PM/PG and TF/TD. The monoplex PCR was specific for FN.

IS-Pro

Total microbiota analysis was performed by IS-pro as described herein above. IS-pro involves bacterial species differentiation by the length of the 16S-23S rDNA interspace (IS) region with taxonomic classification by phylum-specific fluorescent labeling of PCR primers. For amplification of bacterial IS regions for IS-pro, two PCRs were performed. One PCR reaction amplifies IS regions of bacteria belonging to the phyla Firmicutes, Actinobacteria, Fusobacteria, Verrucomicrobia and Bateroidetes. The second PCR amplifies IS regions of bacteria belonging to the highly diverse phylum Proteobacteria. For the first reaction, five primers were used as described herein above. Two fluorescently labeled phylum-specific forward primersin the 16S rDNA region: one FAM-labeled primer, specific for Firmicutes, Actinobacteria, Fusobacteria and Verrucomicrobia (herein referred to as the Firmicutes phylum) and one HEX-labeled primer specific for Bacteroidetes (herein referred to as the Bacteroidetes phylum). Three unlabeled reverse primers were specific for the 23S rDNA region. The combination of these primers provides very broad coverage for the phyla mentioned above. The primers are used in a multiplex PCR, which amplifies the 16S-23S IS region. The length of this IS region and its PCR product is species-specific. The fluorescent label provides identification of all fragments at the phylum level. For the second PCR, specific for Proteobacteria, a single FAM labeled forward primer is used in combination with seven reverse primers as described herein above.

Amplifications were carried out on a GeneAmp® PCR system 9700 (Applied Biosystems, Foster City, Calif.). Cycling conditions for PCR were 35 cycles of 94° C. for 30 s, 56° C. for 45 s, and 72° C. for 1 min and a final extension at 72° C. for 11 min. Each PCR mixture, with a final volume of 25 µl, contained 10 µl of buffered DNA, 1x superTaq buffer (SphaeroQ, Gorinchem, the Netherlands), 200 µM deoxynucleoside triphosphate, 0.04% BSA, 1 U of super-Taq, and 0.13 µM of each of the primers.

After PCR, 5 µl of PCR product was mixed with 19.8 µl formamide and 0.2 µl Mapmaker 1500 ROX-labeled size marker (BioVentures, Murfreesboro, Tenn., USA). DNA fragment analysis was performed on an ABI Prism 3500 Genetic Analyzer (Applied Biosystems).

Data Pre-Processing

All data were pre-processed with the IS-pro proprietary software suite (IS-Diagnostics, Amsterdam, the Netherlands). This process resulted in profiles consisting of peaks with a specific length, measured in nucleotides, reflecting lengths of IS fragments, and a specific height, measured in relative fluorescence units (RFU), reflecting quantity of PCR product. In order to further analyze the data, we considered each peak in a profile as an operational taxonomic unit (OTU) and its corresponding intensity as its abundance. All intensities were log 2 transformed. This conversion was used in all downstream analyses such as calculating within-sample and between-sample microbial diversity.

Heat Maps and Diversity Analysis

Dendrograms of heat maps were constructed by first generating correlation matrices based on Pearson product-moment correlation coefficients (IS-pro) or Euclidian distance (qPCR) and subsequent clustering by UPGMA. Diversity was calculated both per phylum and per the overall microbial composition (by pooling all phyla together). Within-sample diversity was calculated as the Shannon index, that was recently shown to be a robust estimate of microbial diversity. Diversity analysis was performed using the vegan software package in R.

Partial Least Squares Discriminant Analysis (PLS-DA)

A partial least squares discriminant analysis (PLS-DA) regression model was used for the prediction of clinical status of samples; i.e. whether it belonged to a parodontitis patient or to a control subject. PLS-DA is a supervised classification method, which aims to find linear transformations of a matrix of predictors and categorical responses so as to maximize their covariance. The PLS-DA model was constructed on the basis of four different datasets: one for each of the three separate phylum groups and one for the overall microbial composition, by pooling all phyla. Under the assumption that the more discriminant variables are the ones with a higher variance, a preliminary variable selection was performed by filtering out low variance predictors. Only the top 25% most variable predictors were considered in the analysis.

The Variable Importance for Projection (VIP) criterion was used to rank the different OTUs based on their contribution to the response variable (clinical status) and PLS components. PLS-DA provides a quantitative estimate of the discriminatory power of each descriptor by means of VIP (variable importance for the projection) parameters. VIP values rank the descriptors by their ability to discriminate different groups and is therefore considered an appropriate quantitative statistical parameter. Only the OTUs with the highest contribution (VIP score>1.2) were considered. The OTUs resulting from this selection were translated to most likely bacterial species by comparison to a database consisting of >1500 bacterial species and their associated IS lengths. PLS-DA analysis was performed using the DiscriMiner package in R (version 2.15.2). All data visualizations were performed with the Spotfire® software package (TIBCO, Palo Alto, Calif., USA).

Results
Quantative Real-Time PCR

Figure 13:
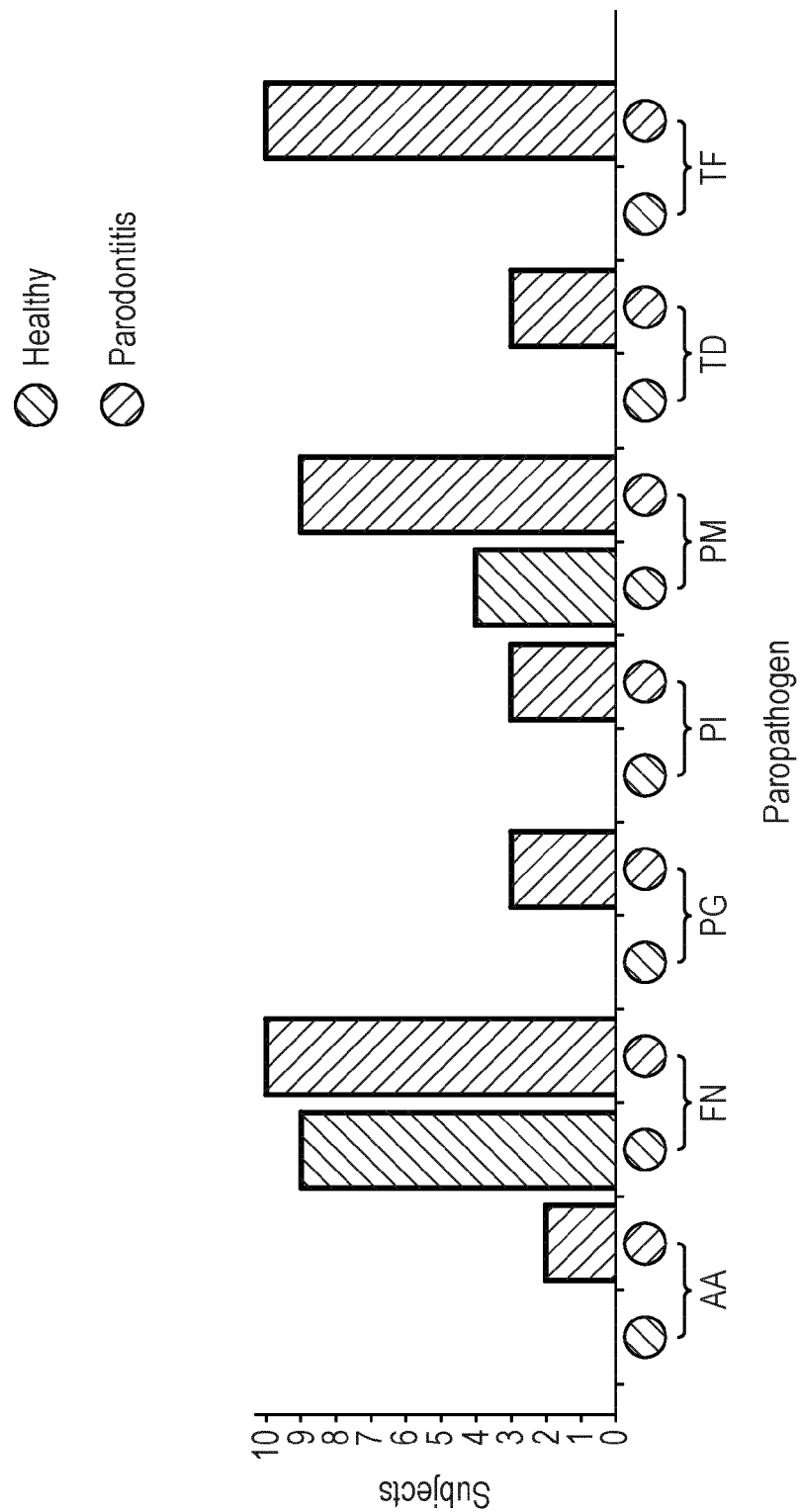
FIG. 13 shows the presence of the seven paropathogens detected by real-time PCR in healthy and diseased subject as described in Example 4. Paropathogens are displayed by patient category (healthy or diseased). Bar heights correspond to the number of subjects positive for that pathogen. It can be seen that five of the seven paropathogens are detected only in diseased subjects.
Figure 14:
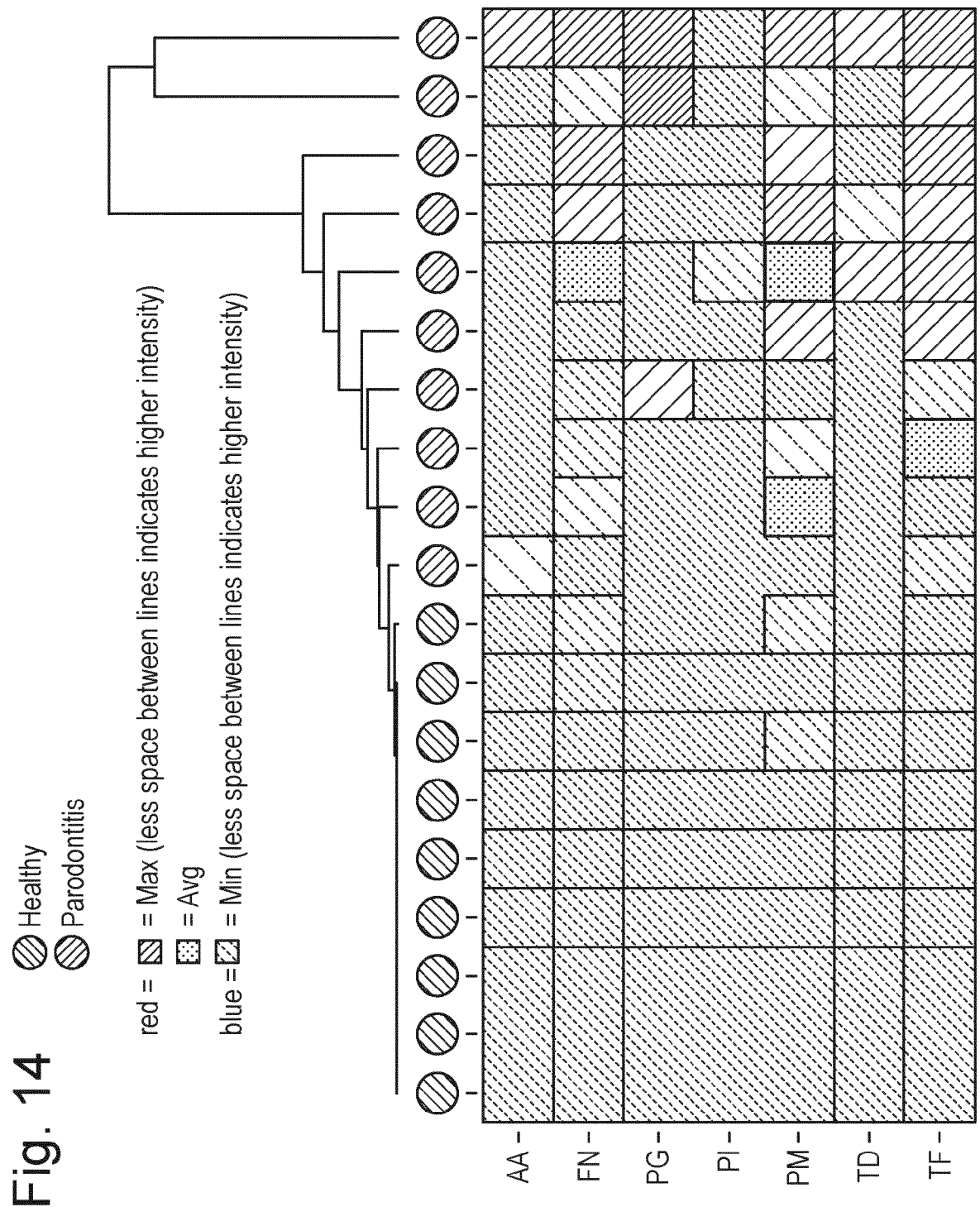
FIG. 14 shows a Clustered Heat map depicting load as measured by quantitative real-time PCR of each paropathogen per patient as described in Example 4. Blue is lowest load, red is highest load. Columns are clustered by Euclidian distance, the dendrogram corresponds to these distances.

Of the seven paropathogens in the real-time PCR reactions, two, *F. nucleatum* and *P. micra* were detected in both healthy and diseased subjects. The other five were detected in diseased subjects only. *T. forsythia* was most discriminative, being present in all ten diseased samples and in none of the healthy subjects (FIG. 13). When loads were taken into account and patients were clustered based on Euclidian distances of the loads of all seven paropathogens combined, it was clear that diseased samples generally harboured higher loads of the one or more of the seven paropathogens. However, clustering of healthy and diseased samples did not show a clear separation into two distinct groups. Rather, a gradual decline in loads of the paropathogens was seen from the diseased group towards the healthy group with no distinct level of separation (FIG. 14).

IS-Pro

Figure 15:
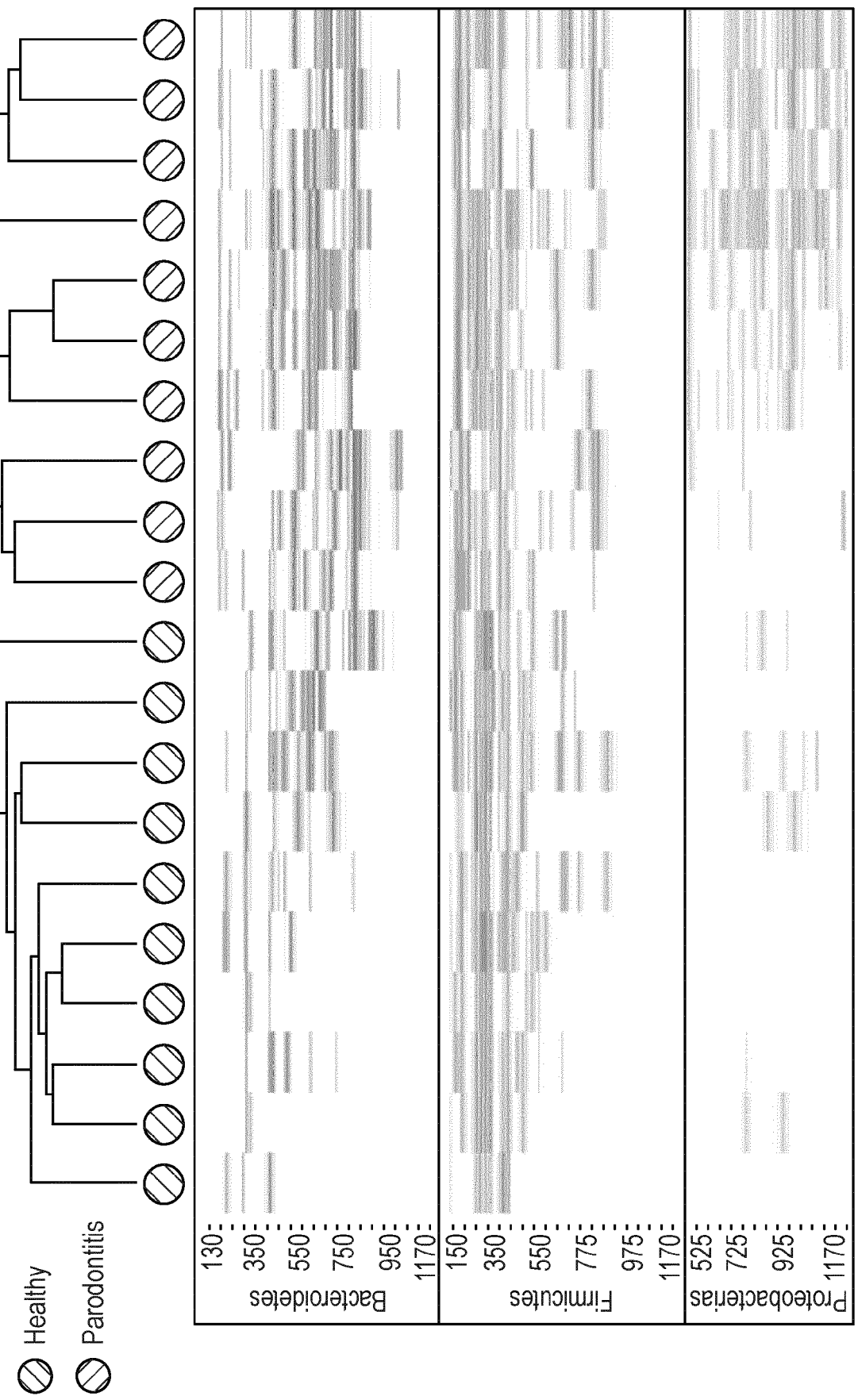
FIG. 15 shows a Clustered Heat map depicting IS-profiles of the three major phyletic groups covered in IS-pro as described in Example 4. Note that Firmicutes group also includes Actinobacteria, Fusobacteria and Verrucomicrobia. It can be seen that there is a clear bipartite separation of microbiota profiles into the healthy and diseased groups, while there is also significant variation within these groups. It can be seen that especially more Proteobacteria species are present in the parodontitis group, corresponding to a higher diversity within this phylum.
Figure 16:
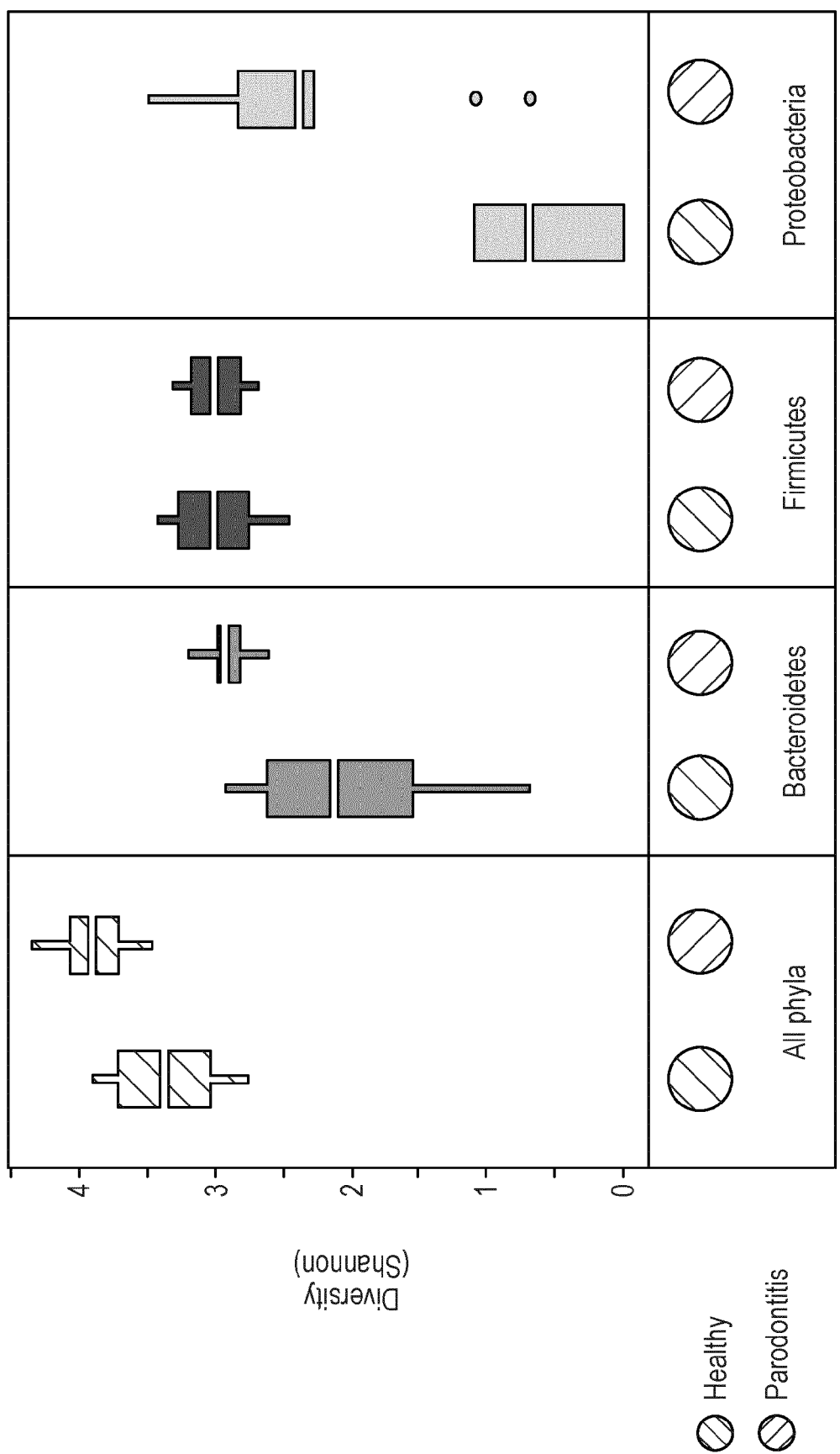
FIG. 16 shows the Shannon diversity per phylum and for all phyla combined as described in Example 4. Proteobacteria and Bacteroidetes display a significantly higher diversity in diseased than in healthy individuals. This also results in a higher diversity for all phyla combined.

IS-pro results showed presence of bacteria form all phyletic groups for most samples. When a heat map was constructed and clustered, there was no gradual separation as with the qPCR. In contrast, the healthy and diseased samples clearly fell into two distinct clusters (FIG. 15). Furthermore, it was seen in the heat map that phyla did not show equal presence in samples from healthy and diseased subjects. Most notably, Proteobacteria showed much higher presence in the parodontitis group than in the healthy group. Bacteroidetes too showed a higher presence in the parodontitis group. These effects were quantified by a diversity analysis. Shannon diversity index was calculated for all samples and showed significant differences between healthy and diseased samples (FIG. 16). Difference in diversity was most outspoken for the phylum Proteobacteria with a mean Shannon diversity index of 2.38 for parodontitis samples (IQR 0.56) and 0.69 for healthy samples (IQR 1.09). This difference was highly significant as calculated by a students t-test ($p=0.0022$). A significant difference in diversity was also found for Bacteroidetes between healthy and diseased samples ($p=0.0048$). For Firmicutes Shannon diversity index was similar for both groups. When all phyla were combined, diversity was still significantly different between the two groups ($p=0.0037$).

Figure 17:
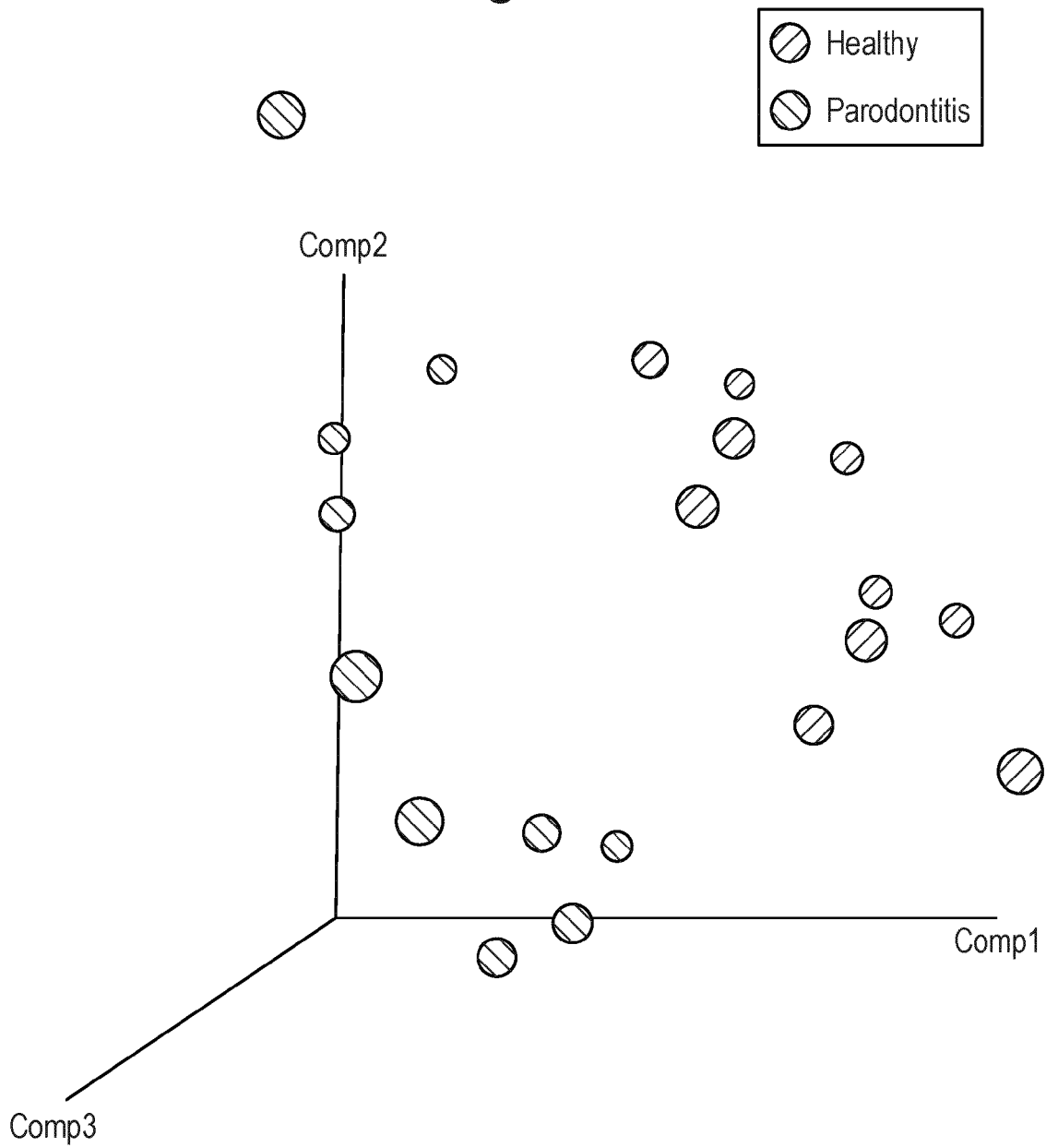
FIG. 17 shows the sample separation by PLS-DA as described in Example 4. It can be clearly seen here that diseased and control samples fall into distinct groups.

Clustering of heat maps and diversity analyses are both based on whole-profile analysis. To investigate the contribution of individual OTU's to sample differences based on health status, PLS-DA was employed. With PLS-DA, we were able to classify samples into healthy and diseased groups with 100% accuracy. In FIG. 17 a low dimentional projection of the PLS-DA analysis is depicted. Interestingly, the OTU's with highest VIP scores belonged to the phylum Firmicutes, followed by Bacteroidetes. Thus, while Proteobacteria showed the most outspoken group effect, this was not attributable to single species. In contrast, presence or absence of particular species was the most important predictor of clinical status for the phylum Firmicutes, and to a lesser extent Bacteroidetes.

DISCUSSION

Whole microbiome analysis of parodontitis samples shows a disease specific microbial pattern, defined by differential presence of specific species of Firmicutes and Bacteroidetes and an overall increase in diversity of Proteobacteria. With a predictive modeling approach, we show that these characteristics may be harnessed to generate highly accurate clinical predictions.

In this study we employ total microbiota analysis not only as a research tool, but also as a diagnostic tool and compare it with the current gold standard of parodontitis diagnostics. We used a parodontitis group as well as a control group that were well defined. The total microbiota data were analysed by classical methods such as correlation and diversity analysis and by predictive modeling. The classical methods are well suited for analysis of whole community structure, while the predictive modeling can assign importance to individual species.

A drawback of the current study was that the study population was too small to draw final conclusions. The observed effects on total microbiota should be confirmed in a larger population. A larger population in combination with cross-validation of the PLS-DA will be necessary for robust evaluation of applicability of IS-pro as a clinical tool for diagnosing parodontitis.

qPCR is a well validated method that has shown its value in clinical practice. However, as it can only measure presence of seven distinct species and it does not give information over total community status or dynamics. IS-pro does give an overview of the total microbial community present in the parodontium. Differences in diversity were very outspoken for the different phyla. For Proteobacteria, this effect was greatest, varying from absence of Proteobacteria in a subset of the healthy individuals to a highly diverse population in diseased individuals. A very interesting finding in this context was that the increase in Proteobacteria was not attributable to particular species, but consisted of different species between individuals. This may suggest a niche opening up in diseased subjects which may be exploited by different species of Proteobacteria, but not by members of the other phyla. It is interesting to note in this context, that an increase in Proteobacterial presence has been found in various inflammatory processes in the gut (ref). Furthermore, the presence of several distinct species of the phyla Firmicutes, Fusobacteria and Bacteroidetes in parodontitis has been well established (ref) and has been confirmed in this study.

Taken together, our data suggests a process in which distinct species are involved in (initiation of) parodontitis. After this, possibly because of the inflammatory process, a niche might open up which can be exploited by members of the phylum Proteobacteria.

This study contributes to a better understanding of the role of the oral microbiota in parodontitis. Furthermore, it demonstrates how microbiota profiling may be applied to improve clinical diagnostics in oral healthcare. While diagnostic tests aimed at a limited set of known paropathogens have been established, analysis of the total microbiota enables measuring presence and relative quantity of all bacteria present in a sample. By applying a predictive model such as PLS-DA to such datasets, many more parameters can be taken into account for clinical prediction than in defined species assays. Not only can these species be taken into account, but by applying weights to the presence and relative quantity of all of the detected species, clinical prediction may become much more accurate.

In conclusion, we demonstrate that even in a small sample set, whole microbiota analysis of oral samples can predict clinical status with high accuracy. This study warrants further evaluation of this approach in a larger sample set with a cross-validated predictive modeling approach.

Example 5. Testing Fecal Samples of Crohn's Disease Patients

Figure 18:
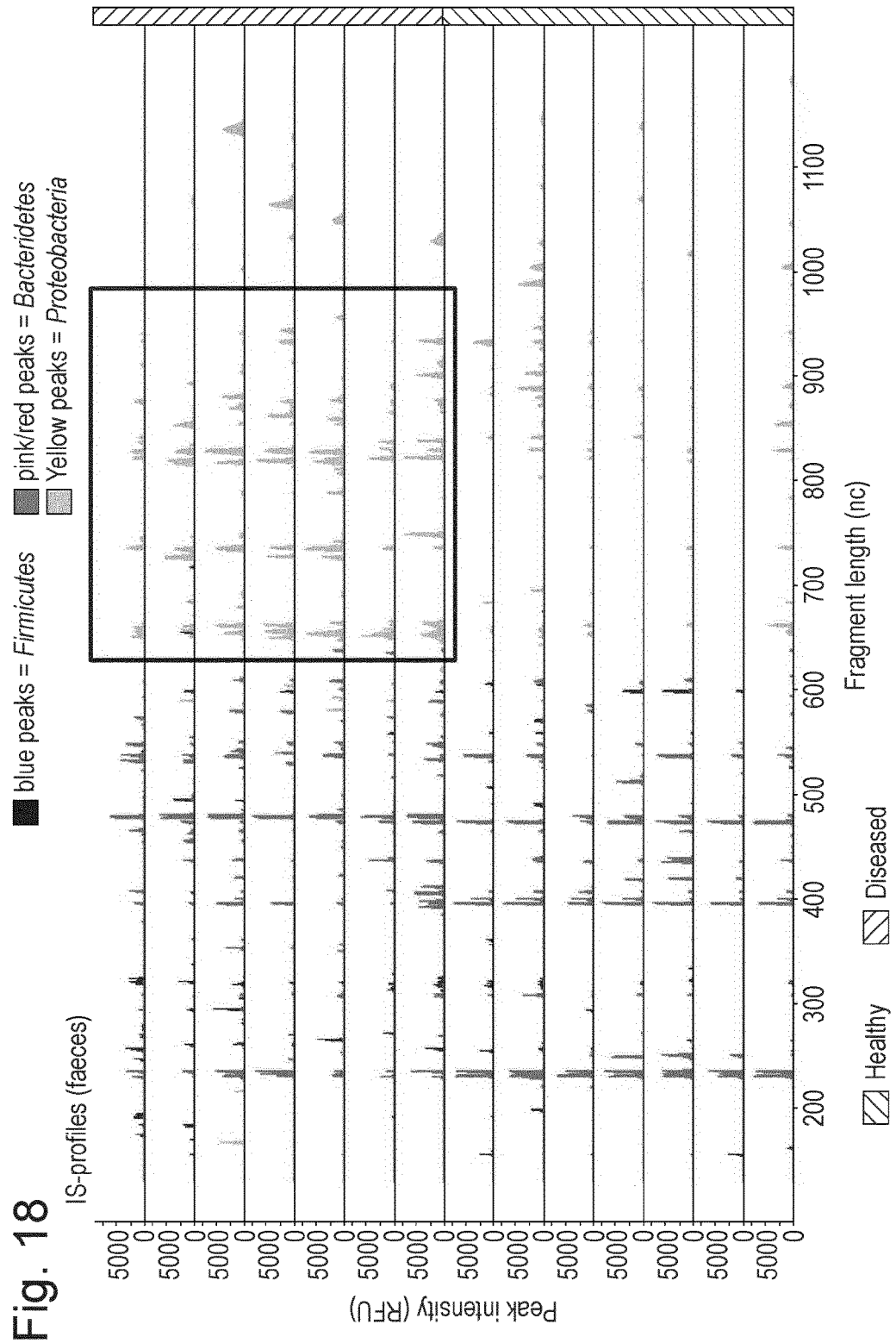
FIG. 18 shows the IS-Pro profile (profile view) of fecal samples of Crohn's Disease patients and control subjects as described in Example 5.
Figure 19:
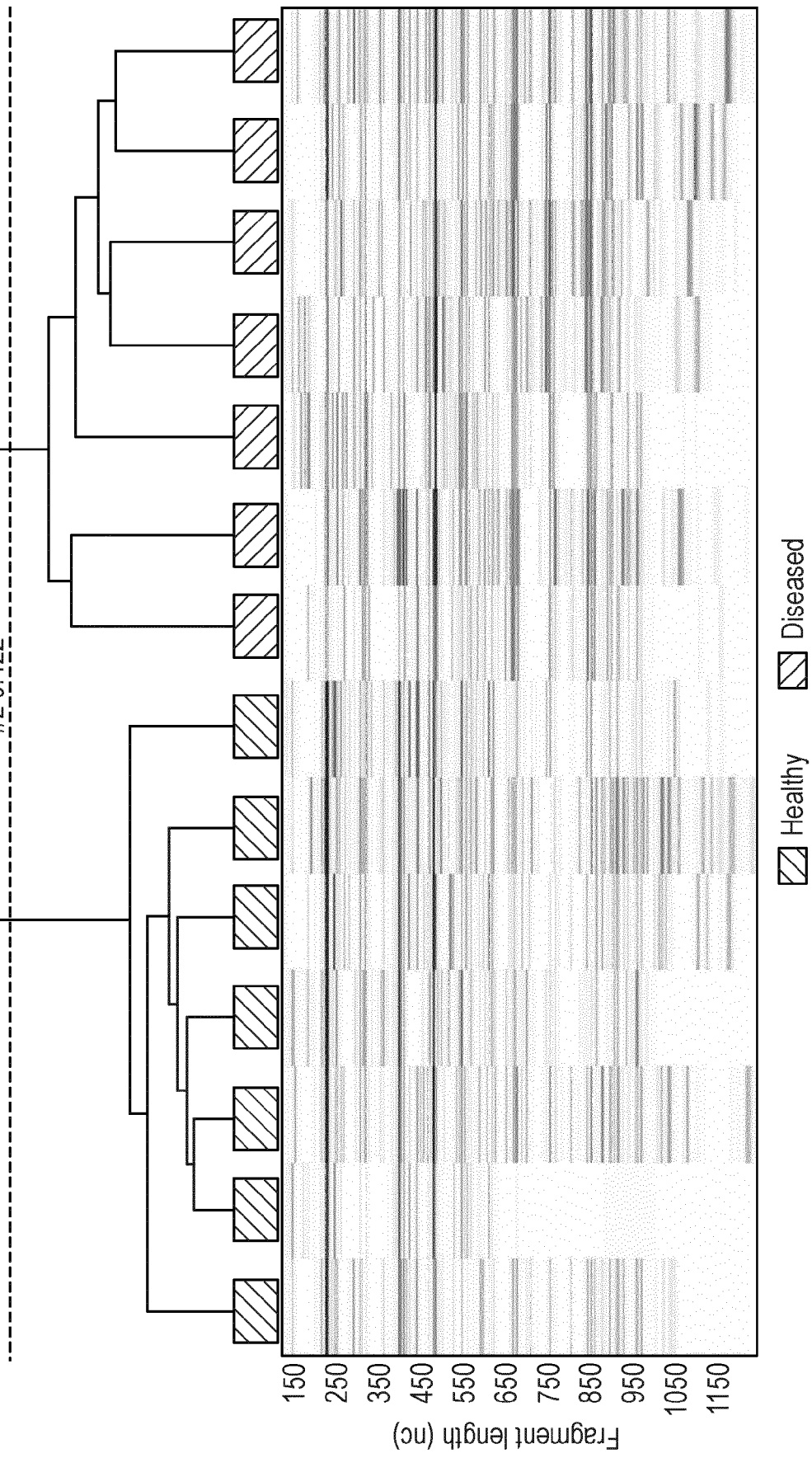
FIG. 19 shows the IS-Pro profile (band view, or heat map) of fecal samples of Crohn's Disease patients and control subjects as described in Example 5.

Fecal samples obtained by rectal swab as described in Example 3 above were obtained from 7 patients suffering from Crohn's Disease, and analysed using the IS-pro technique as described herein in Examples 2-4 using the primers as described for the phyla Firmicutes, Bacteroidetes and Proteobacteria as described herein above. A total of 7 control subjects was included as a healthy control population. The results of the analysis are displayed in FIG. 18 (profile view) and FIG. 19 (band view, or heat map). In this Example, and in all other Examples and Figures displayed herein, the data are displayed as profile view and band view. In the profile views. Blue peaks represent the IS regions amplified from the phylum Firmicutes, pink/red peaks represent the IS regions amplified from the phylum Bacteroidetes, and yellow peaks represent the IS regions amplified from the phylum Proteobacteria. At the right side of the graph it is indicated in bars whether the profiles are from diseased (red) or healthy (green) subjects (except in FIGS. 44 and 45, wherein healthy individuals in the Shannon index distribution are indicated in red). Marked differences in the peak profiles between diseased and healthy patients are clearly indicated by boxing of the peak regions.

In the band views or heat maps, each column represents a distinct IS profile obtained from one sample/subject. The color intensity corresponds to the peak-height. Although the different phyla are not recognizable in this display, the phylum association of the various bands was used in the UPGMA clustering analysis, separating diseased (red) from healthy (green). In the instances where marked differences in peak profiles could were not discernable by eye from the profile views, UPGMA clustering could clearly distinguish diseased profiles from healthy profiles.

In the present Example, a clear distinction could be made between the fecal microbiomes of patients suffering from the disease versus the healthy control population. Markedly, the IS profile of the Proteobacteria group exhibited much higher diversity in the diseased group, with both a higher number of peaks and higher total peak surface area for amplified ITS fragments having nucleotide lengths between 650 and 1000 nucleotides.

Example 6. Testing Fecal Samples of Ulcerative Colitis Patients

Figure 20:
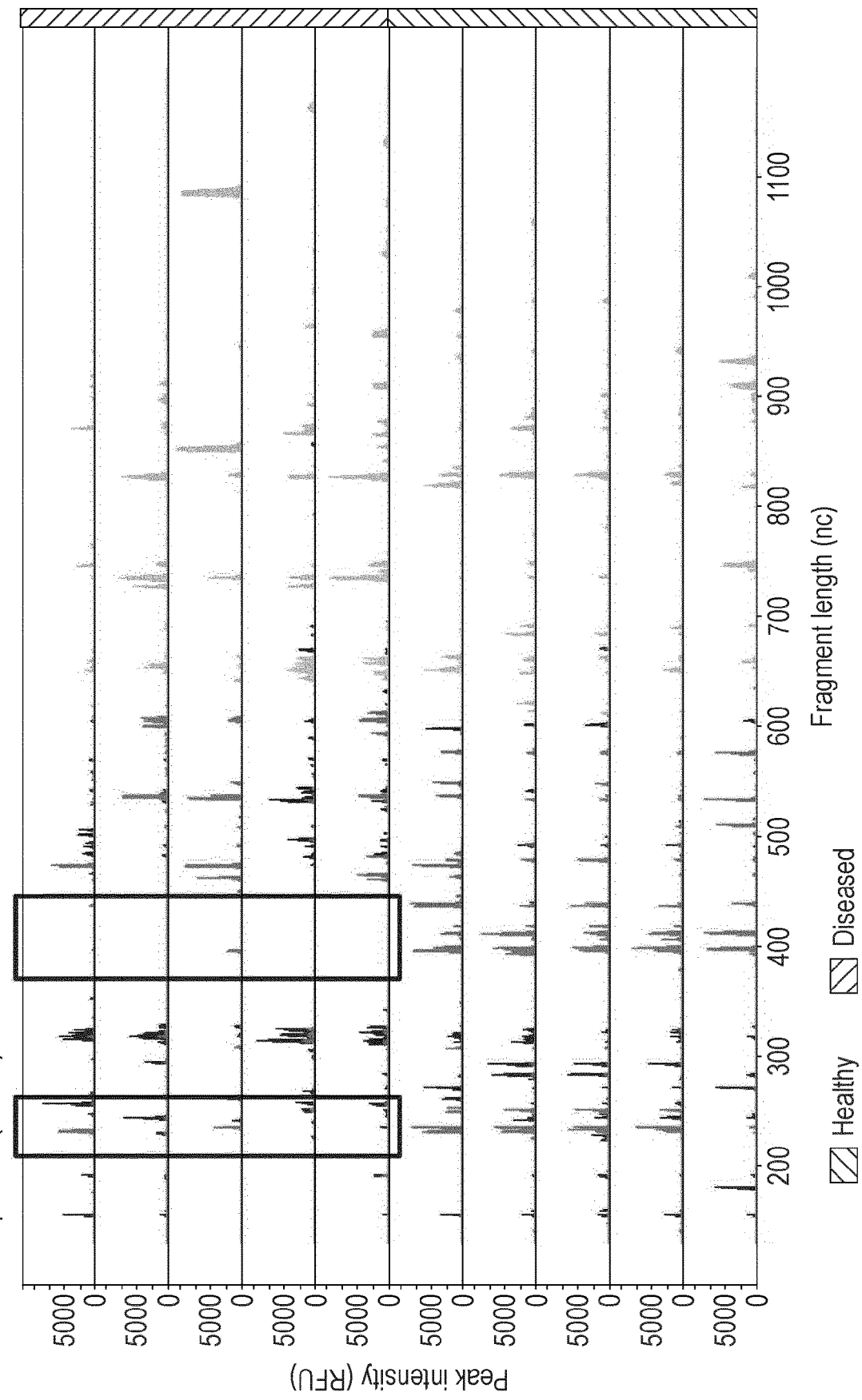
FIG. 20 shows the IS-Pro profile (profile view) of fecal samples of Ulcerative colitis patients and control subjects as described in Example 6.
Figure 21:
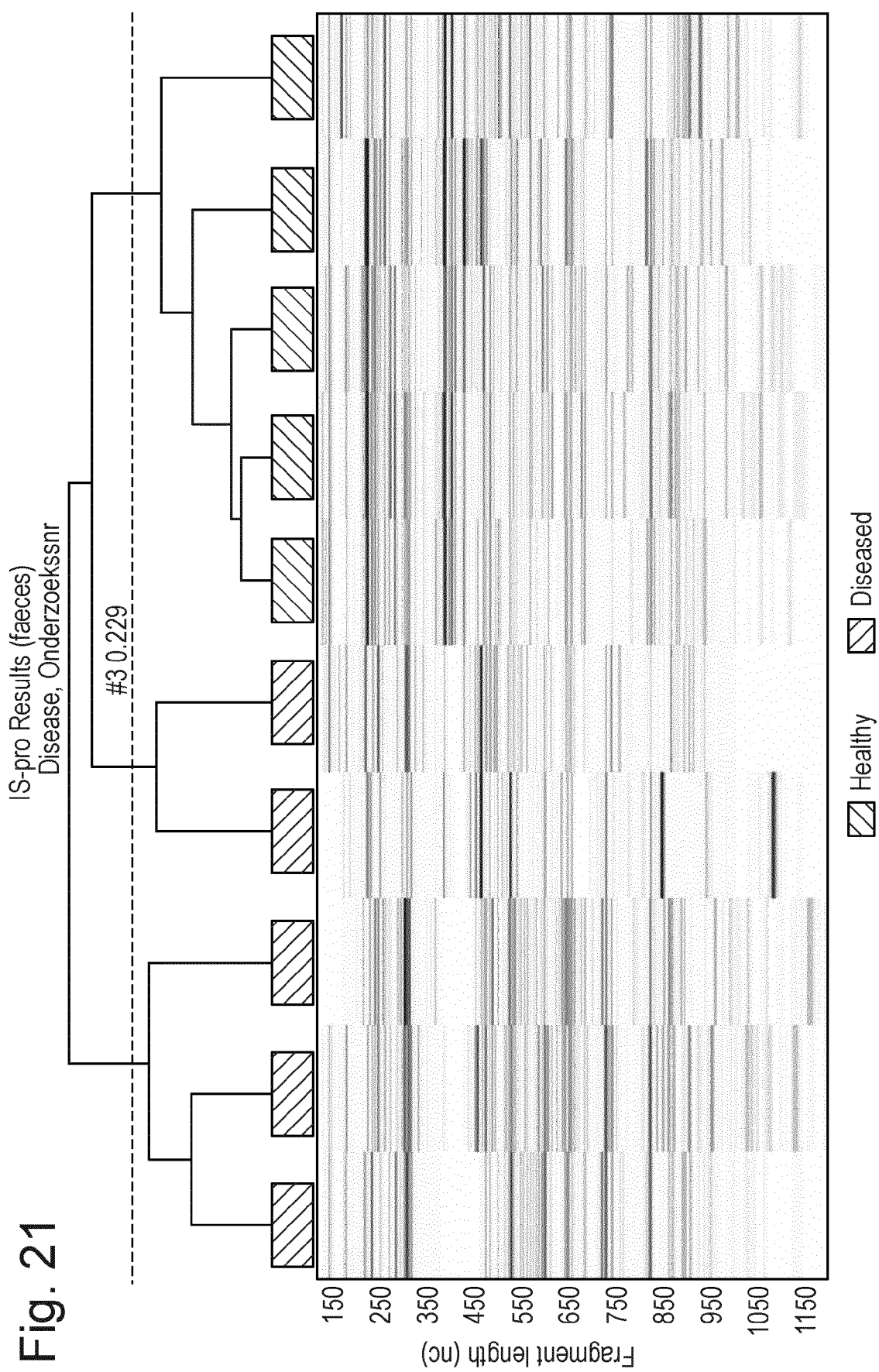
FIG. 21 shows the IS-Pro profile (band view) of fecal samples of Ulcerative colitis patients and control subjects as described in Example 6

Fecal samples obtained by rectal swab as described in Example 3 above were obtained from 5 patients suffering from ulcerative colitis, and analysed using the IS-pro technique as described herein in Examples 2-4 using the primers as described for the phyla Firmicutes, Bacteroidetes and Proteobacteria as described herein above. A total of 5 control subjects was included as a healthy control population. The results of the analysis are displayed in FIG. 20 (profile view) and FIG. 21 (band view).

In the present Example, a clear distinction could be made between the fecal microbiomes of patients suffering from ulcerative colitis versus the healthy control population. Markedly, the IS profile of the phylum Bacteroidetes showed clear absence of certain species from that phylum the diseased group, notable an absence of amplified ITS fragments having nucleotide lengths between 390 and 450 nucleotides.

Example 7. Testing Fecal Samples of Eczema Patients

Figure 22:
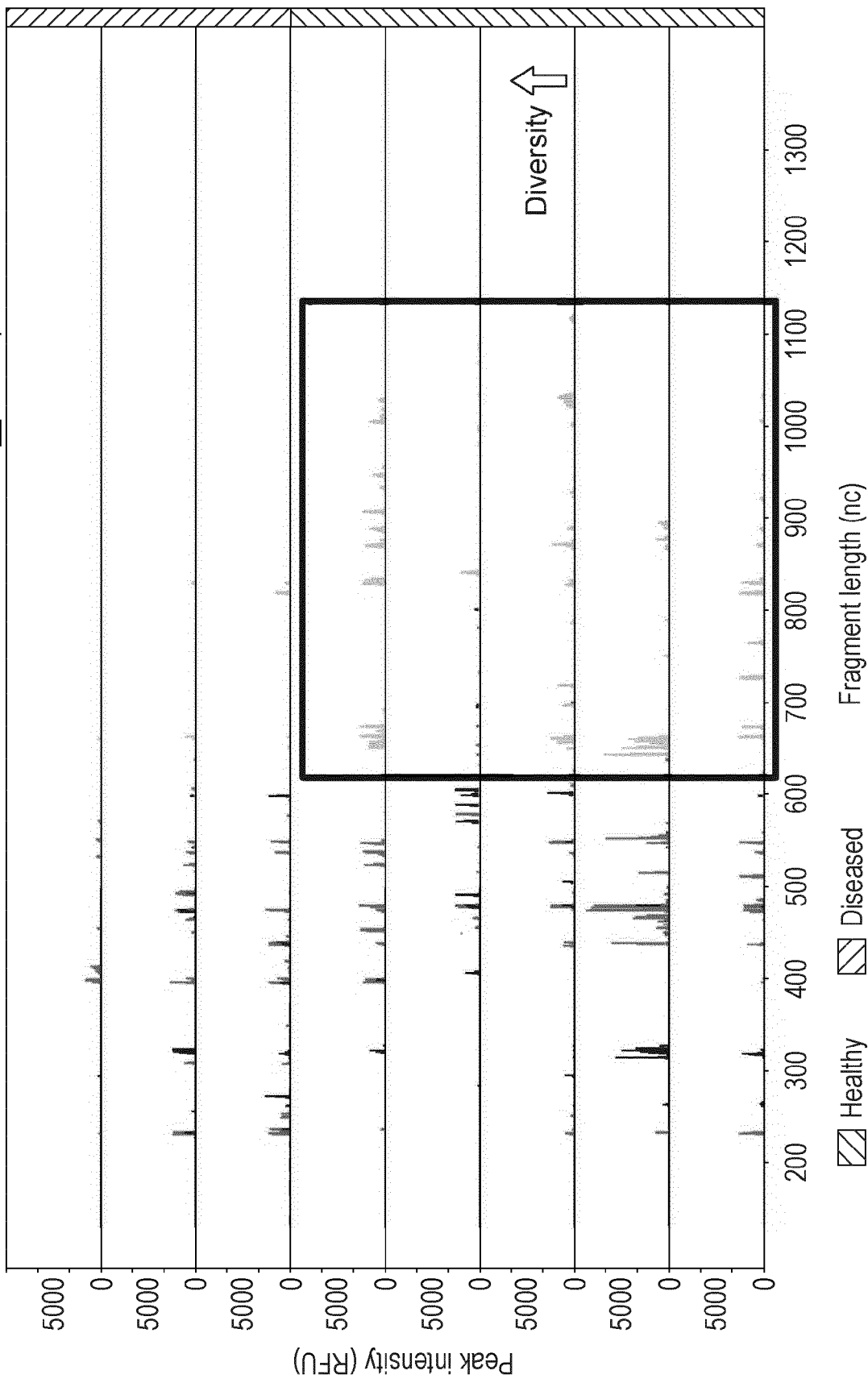
FIG. 22 shows the IS-Pro profile (profile view) of fecal samples of Eczema patients and control subjects as described in Example 7.
Figure 23:
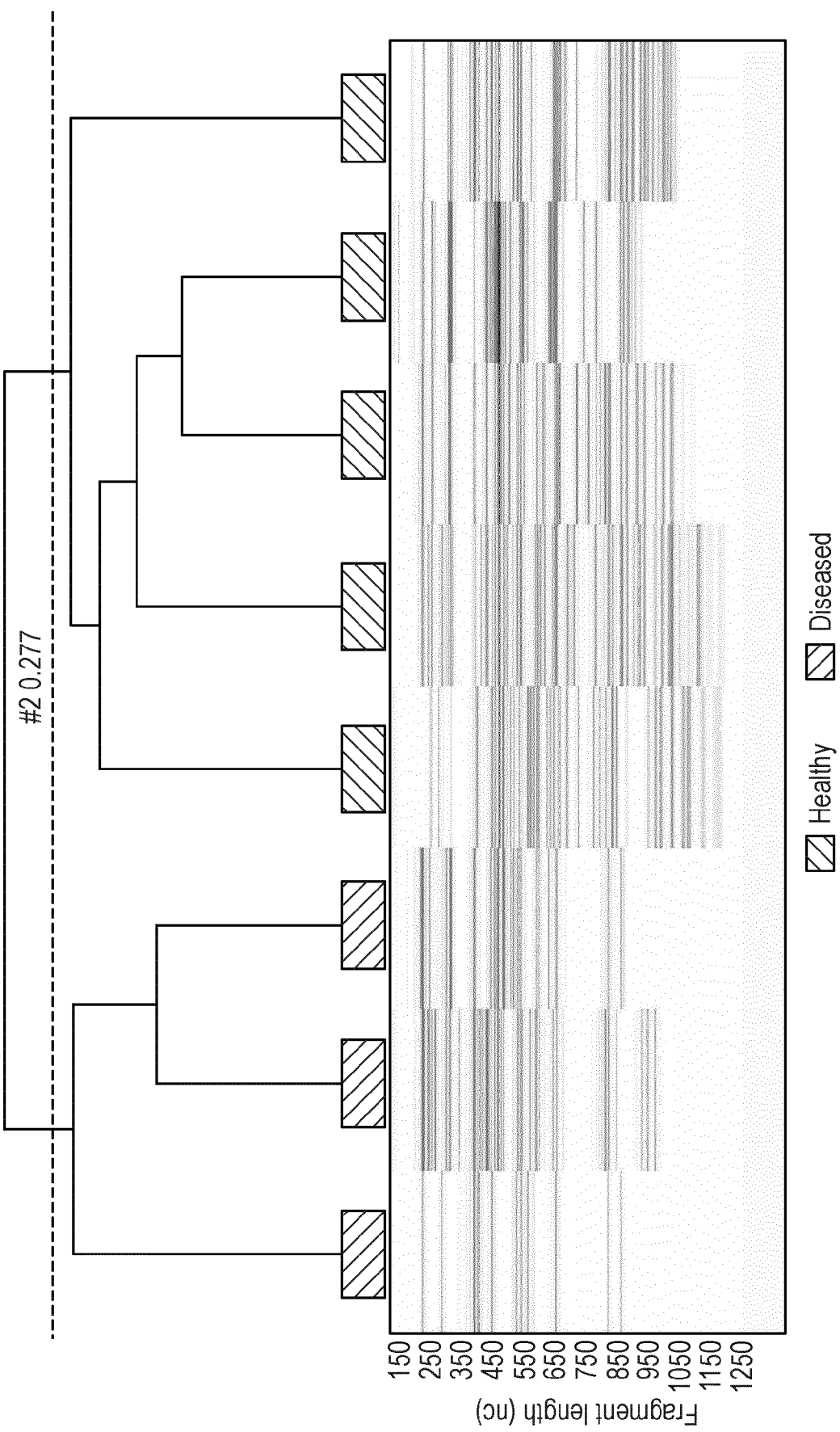
FIG. 23 shows the IS-Pro profile (band view) of fecal samples of Eczema patients and control subjects as described in Example 7.

Fecal samples obtained by rectal swab as described in Example 3 above were obtained from 3 patients suffering from eczema, and analysed using the IS-pro technique as described herein in Examples 2-4 using the primers as described for the phyla Firmicutes, Bacteroidetes and Proteobacteria as described herein above. A total of 5 control subjects was included as a healthy control population. The results of the analysis are displayed in FIG. 22 (profile view) and FIG. 23 (band view).

In the present Example, a clear distinction could be made between the fecal microbiomes of patients suffering from eczema versus the healthy control population. Markedly, the IS profile of the Proteobacteria group exhibited much higher diversity in the healthy control group. Both a reduced number of peaks and lower total peak surface area for amplified ITS fragments having nucleotide lengths between 650 and 1100 nucleotides was found for the eczema group.

Figure 24:
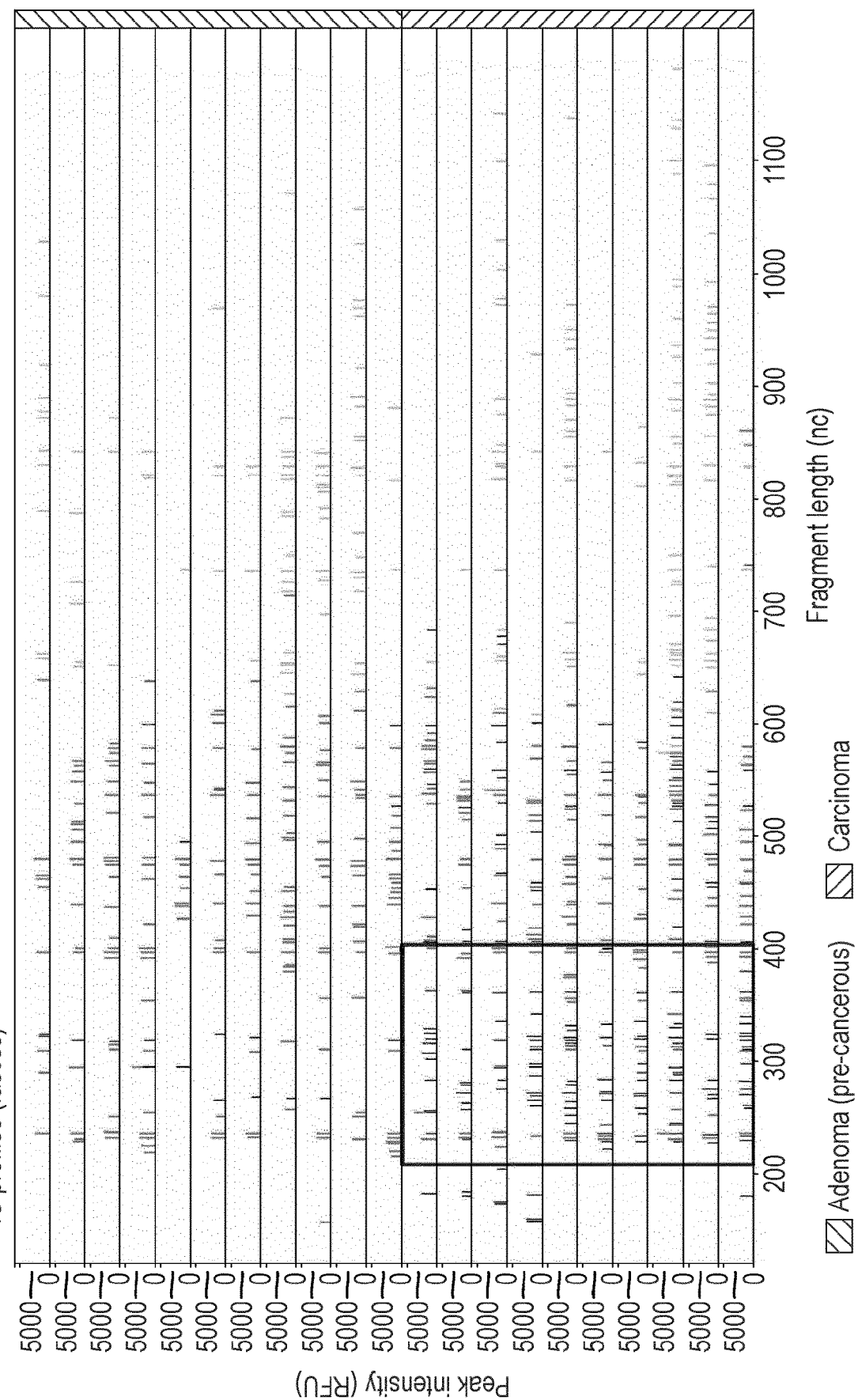
FIG. 24 shows the IS-Pro profile (profile view) of fecal samples of Colon carcinoma patients and adenoma control subjects as described in Example 8.
Figure 25:
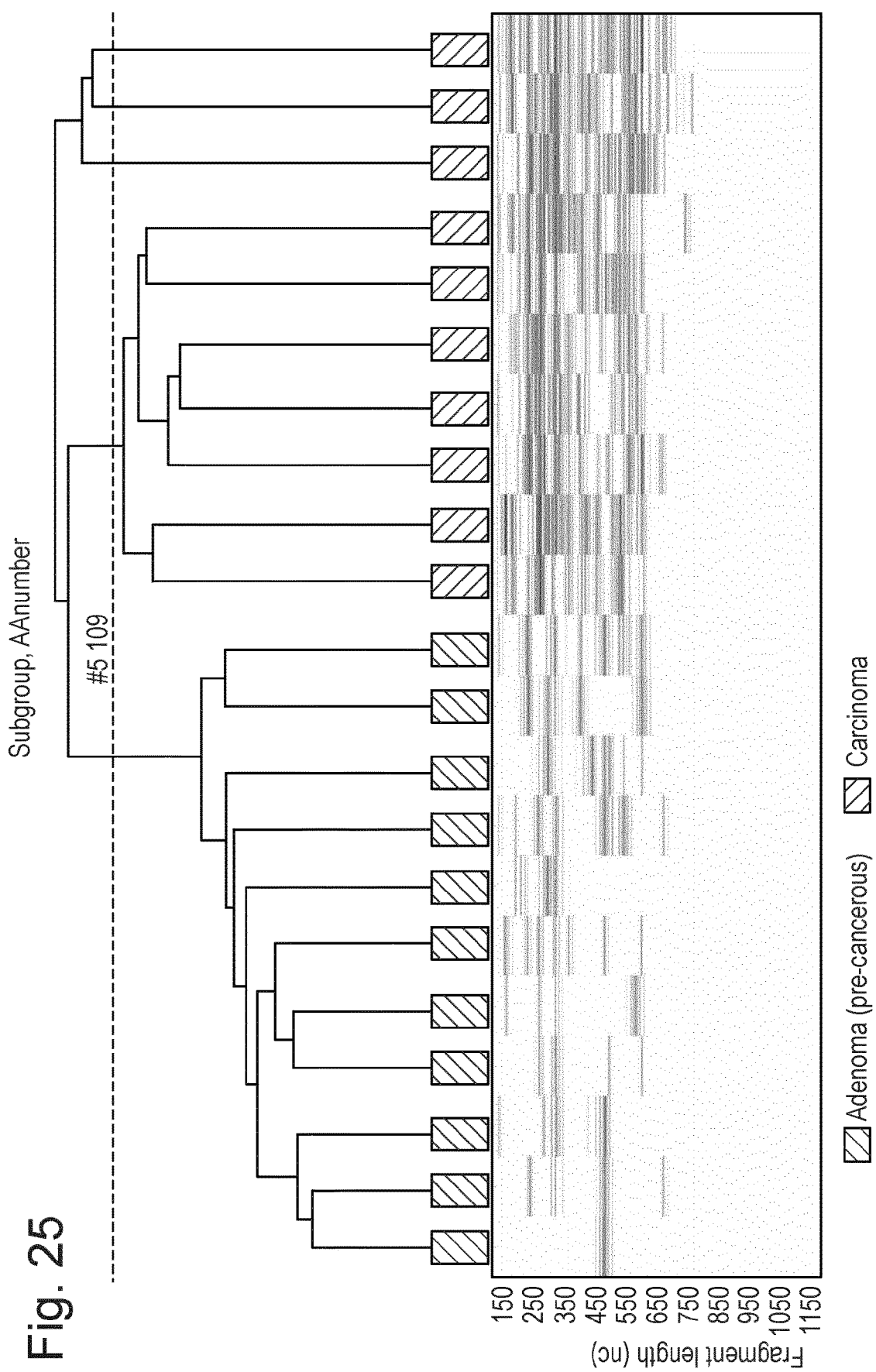
FIG. 25 shows the IS-Pro profile (Firmicutes band view) of fecal samples of Colon carcinoma patients and adenoma control subjects as described in Example 8.

Example 8. Testing Fecal Samples of Colon Carcinoma Patients and Adenoma Control Subjects Fecal samples obtained by rectal swab as described in Example 3 above were obtained from 10 patients suffering from colon carcinoma, and analysed using the IS-pro technique as described herein in Examples 2-4 using the primers as described for the phyla Firmicutes, Bacteroidetes and Proteobacteria as described herein above. A total of 11 control subjects having pre-cancerous adenoma were included as a control population. The results of the analysis are displayed in FIG. 24 (profile view) and FIG. 25 (band view).

In the present Example, a clear distinction could be made between the fecal microbiomes of patients suffering from colon carcinoma versus the control population. Markedly, the IS profile of the phylum Firmicutes exhibited much higher diversity in the colon carcinoma group. A marked increase in the number of peaks for amplified ITS fragments having nucleotide lengths between 200 and 400 nucleotides was found for the colon carcinoma group.

Figure 26:
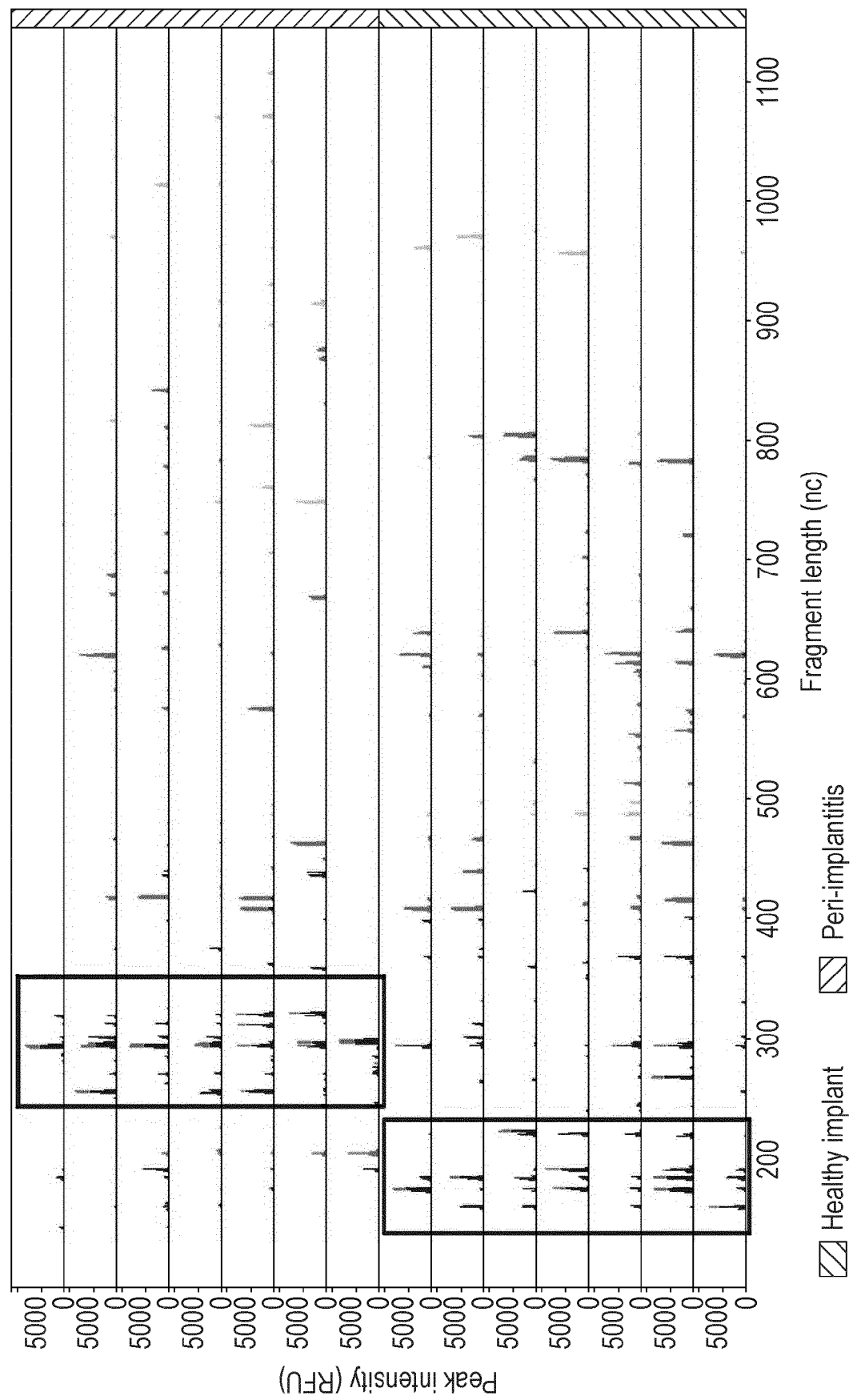
FIG. 26 shows the IS-Pro profile (profile view) of paperpoint samples of Peri-implantitis patients and control subjects as described in Example 9.
Figure 27:
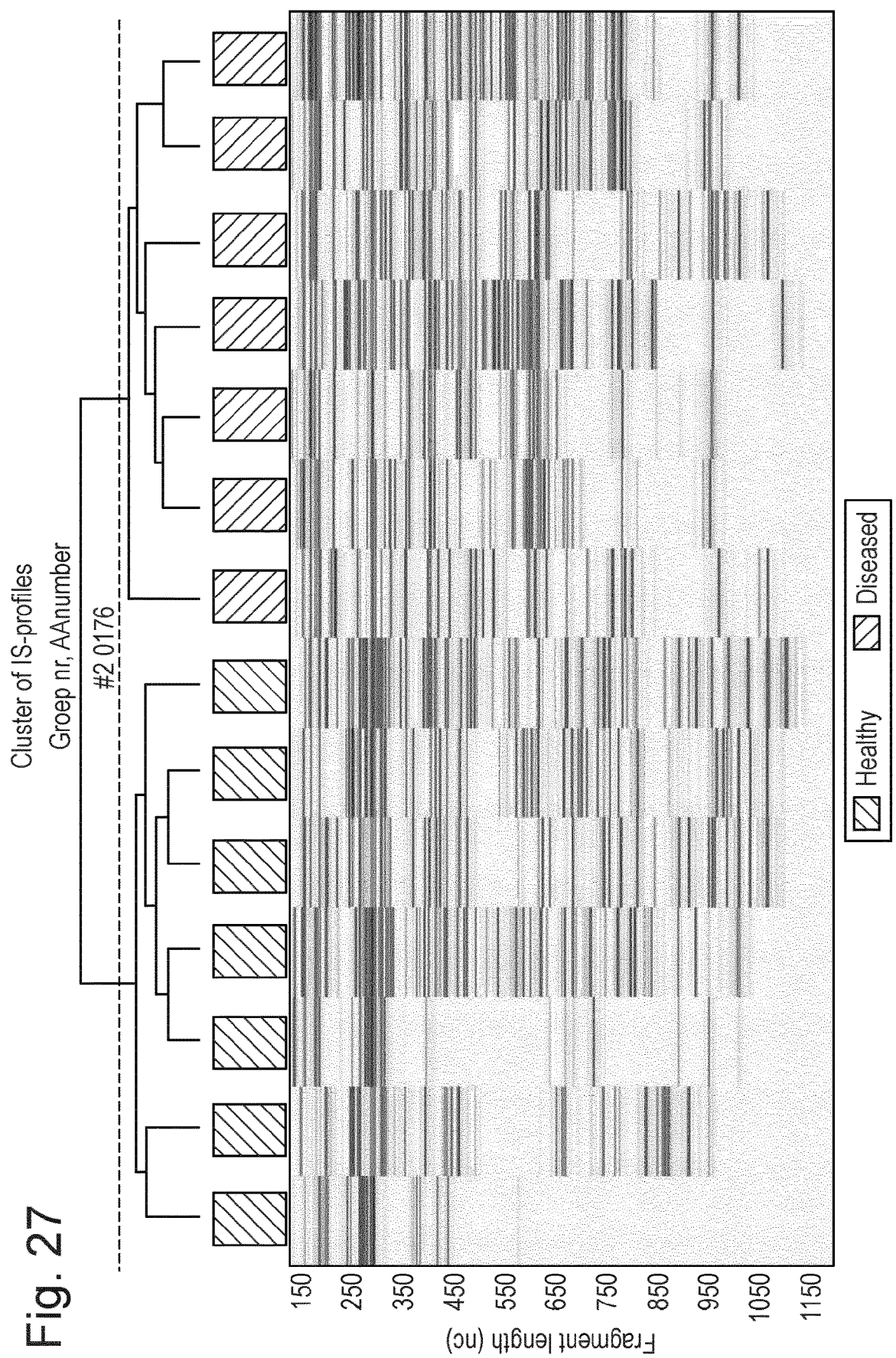
FIG. 27 shows the IS-Pro profile (band view) of paperpoint samples of Peri-implantitis patients and control subjects as described in Example 9.

Example 9. Testing Paperpoint Samples of Patients Suffering from an Peri-Implantitis Paperpoint samples obtained as described in Example 4 above were obtained from 7 patients suffering from peri-implantitis, and analysed using the IS-pro technique as described herein in Examples 2-4 using the primers as described for the phyla Firmicutes, Bacteroidetes and Proteobacteria as described herein above. A total of 7 healthy control subjects were included as a control population. The results of the analysis are displayed in FIG. 26 (profile view) and FIG. 27 (band view).

Figure 28A:
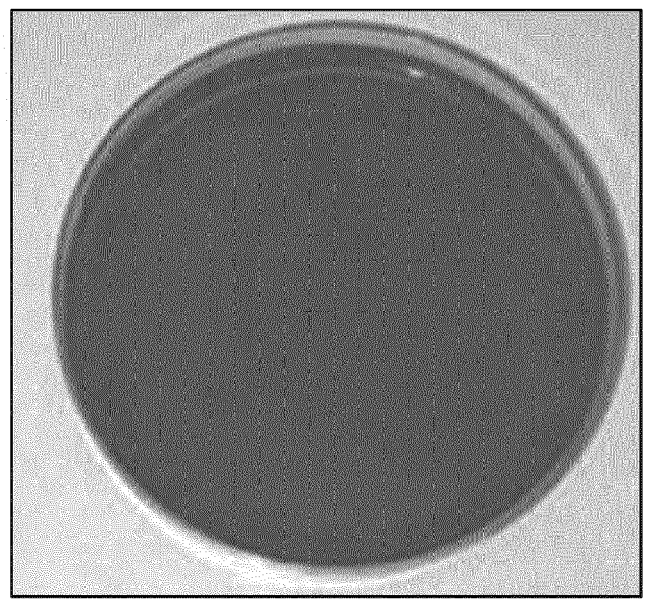
FIG. 28 shows the IS-Pro profile (profile view) of a sample of a patient suffering from an Abscess as described in Example 10. Panel A shows a petri dish following incubation with the Abscess sample, exemplifying the culture result wherein no bacterial growth was observed. Panel B shows the IS profile of the Abscess sample, indicating the presence of a single bacterial species of the phylum Firmicutes, *Streptococcus cristatus*.

In the present Example, a clear distinction could be made between the paperpoint samples of patients suffering from peri-implantitis versus the control population. Markedly, the IS profile of the phylum Bacteroidetes (pink/red peaks) with presence of ITS fragments of 300 nucleotides in length was specific for the diseased group, whereas the phylum Firmicutes exhibited a shift in profile from species having ITS fragment lengths of around 150-250 nucleotides in the healthy group, towards species having ITS fragment lengths of around 250-350 nucleotides in the diseased group Example 10. Testing Wound Samples of Patients Suffering from an Abscess A wound sample of a patient suffering from an abscess was obtained and analysed using the IS-pro techniques as described herein. The sample was also cultivated on standard cultivation media in order to detect the presence of any cultivable bacterium. The results are displayed in FIG. 28.

No bacterial growth was observed on solid cultivation media. Panel B shows the IS profile of the abscess sample, indicating the presence of a single bacterial species of the phylum Firmicutes, *Streptococcus cristatus*.

Example 11. Testing Fecal Samples of Anorexia Nervosa Patients

Figure 29:
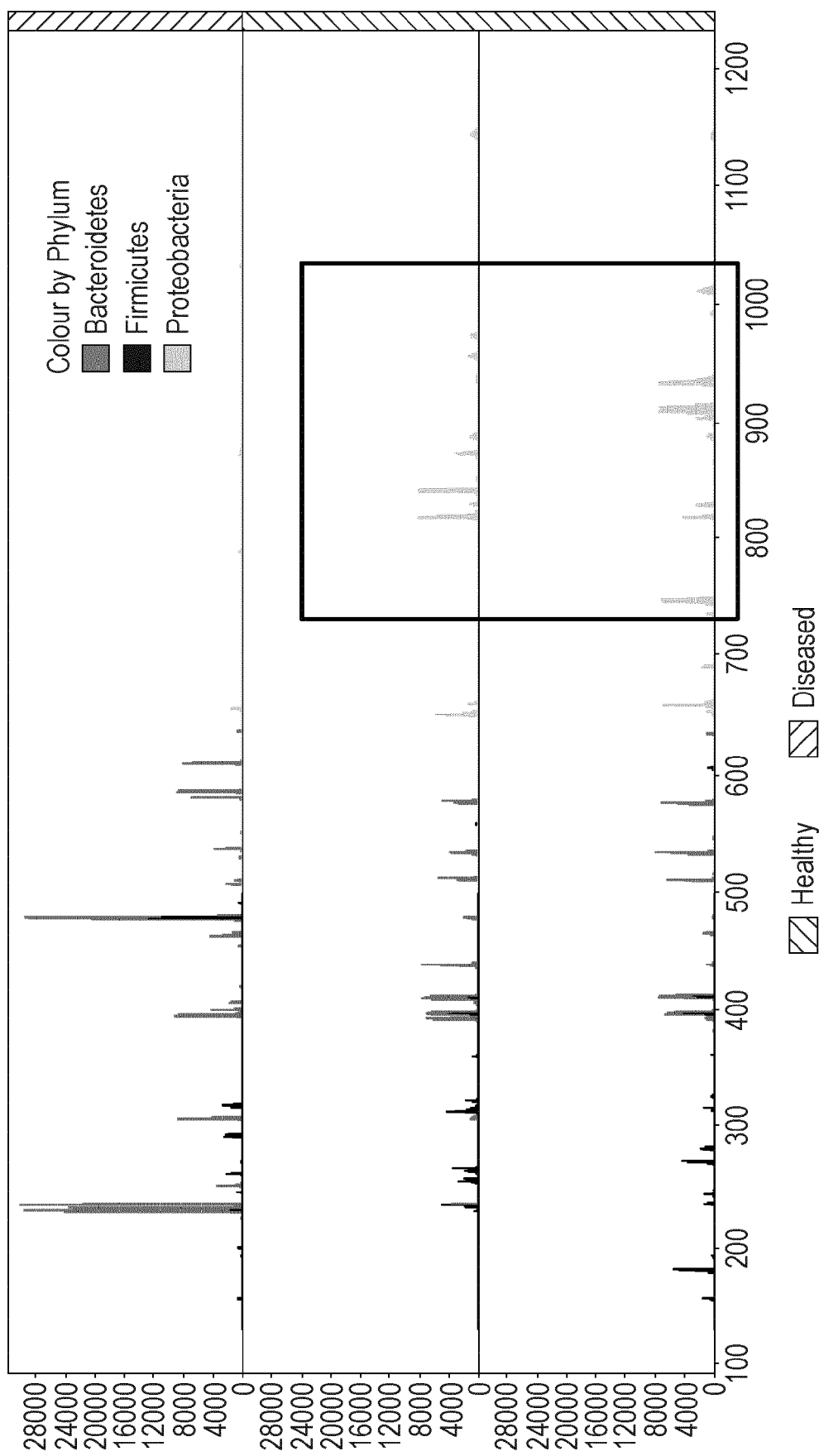
FIG. 29 shows the IS-Pro profile (profile view) of fecal samples of Anorexia nervosa patients and control subjects as described in Example 11.
Figure 30:
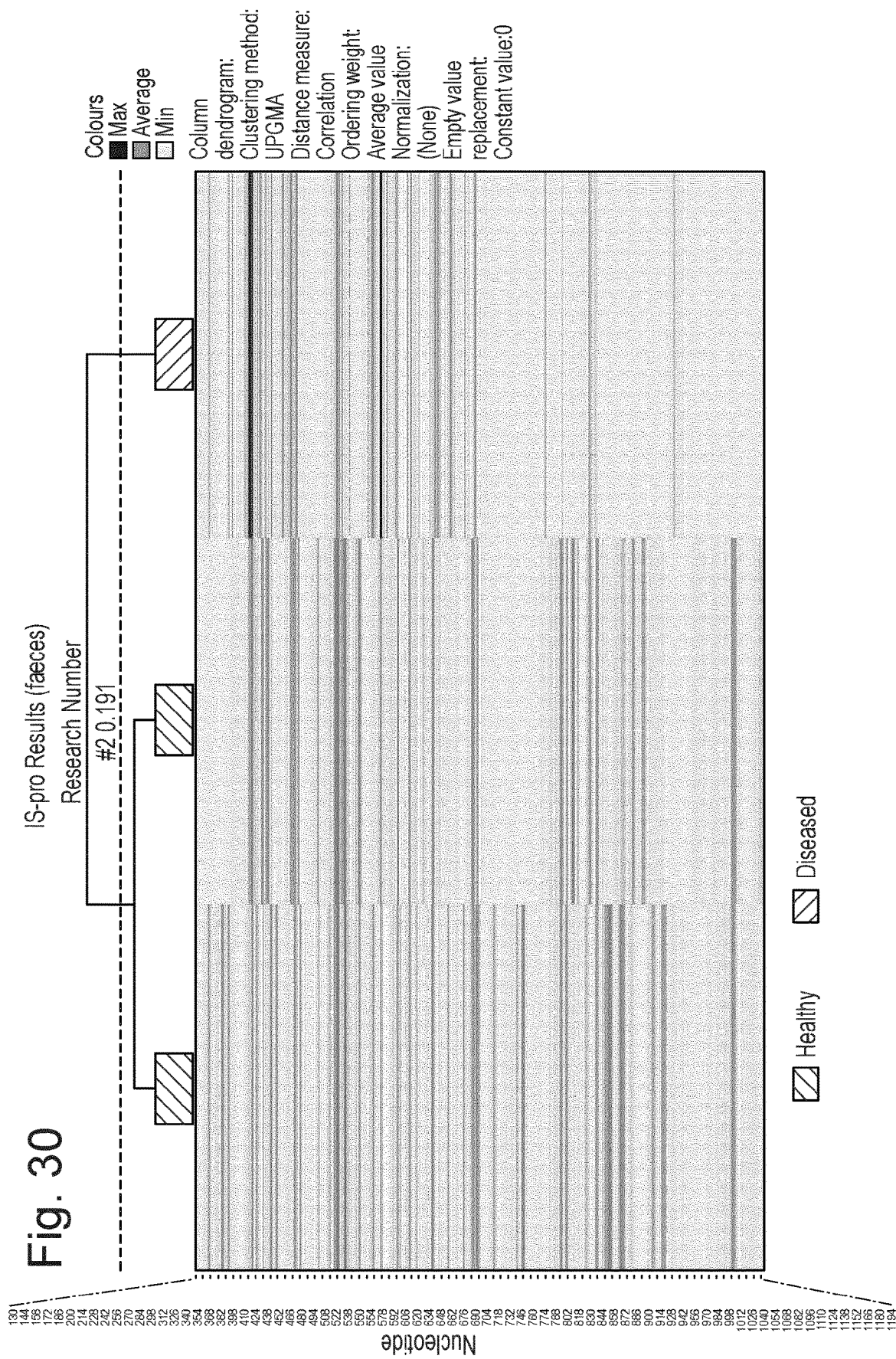
FIG. 30 shows the IS-Pro profile (band view) of fecal samples of Anorexia nervosa patients and control subjects as described in Example 11.

A fecal sample was obtained by rectal swab as described in Example 3 above from a patient suffering from anorexia nervosa, and analysed using the IS-pro technique as described herein in Examples 2-4 using the primers as described for the phyla Firmicutes, Bacteroidetes and Proteobacteria as described herein above. Two control subject fecal samples were included as healthy controls. The results of the analysis are displayed in FIG. 29 (profile view) and FIG. 30 (band view).

In the present Example, a clear distinction could be made between the fecal microbiome of the anorexia nervosa patient versus the control population. Markedly, the IS profile of the phylum Bacteroidetes showed distinct peaks at around 230 nucleotides in the anorexia patient, wherein the diversity of the phylum Proteobacteria had markedly decreased in the anorexia patient relative to the control samples.

Example 12. Testing Fecal Samples of Asthma Patients

Figure 31:
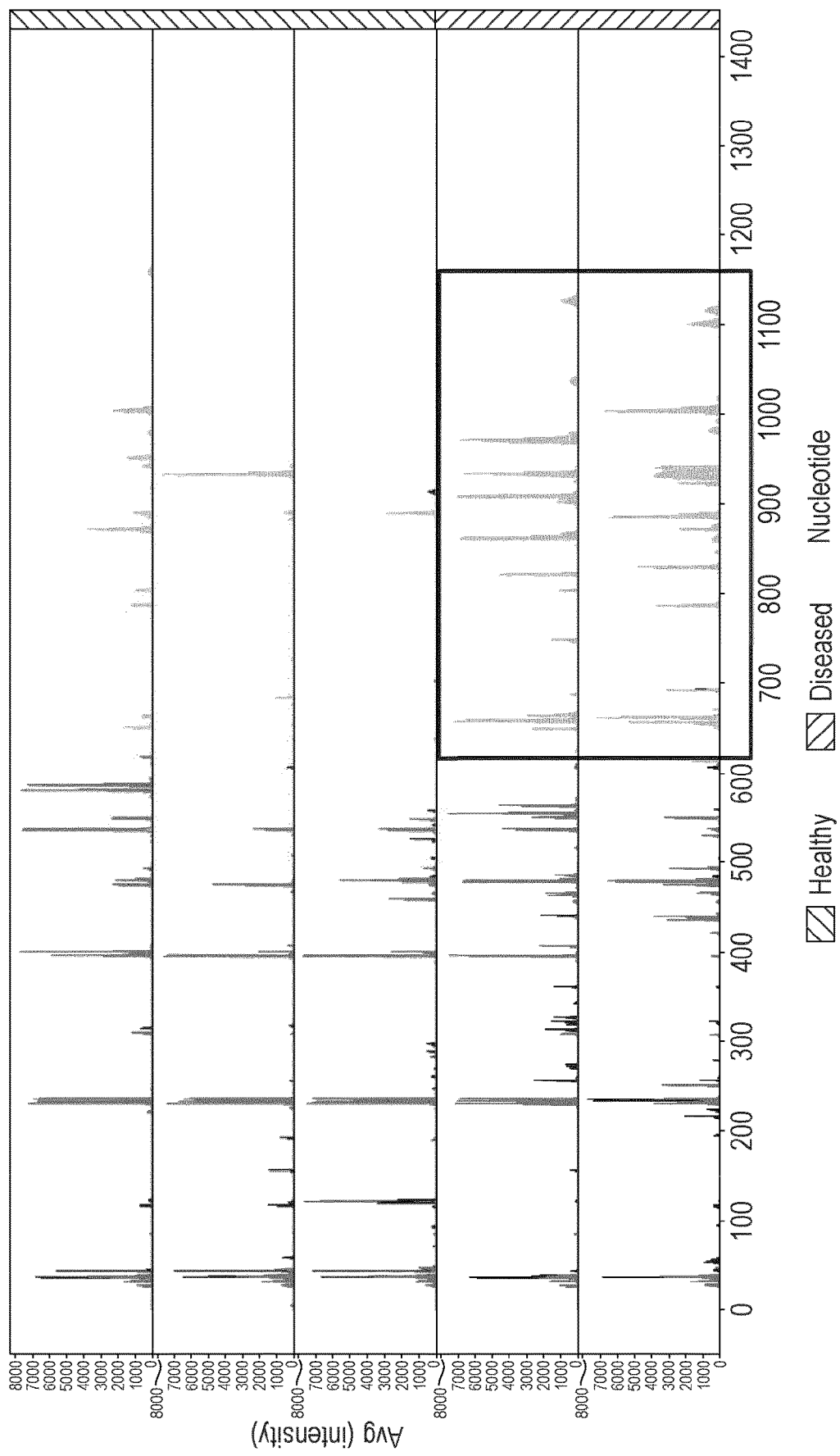
FIG. 31 shows the IS-Pro profile (profile view) of fecal samples of Asthma patients and control subjects as described in Example 12.
Figure 32:
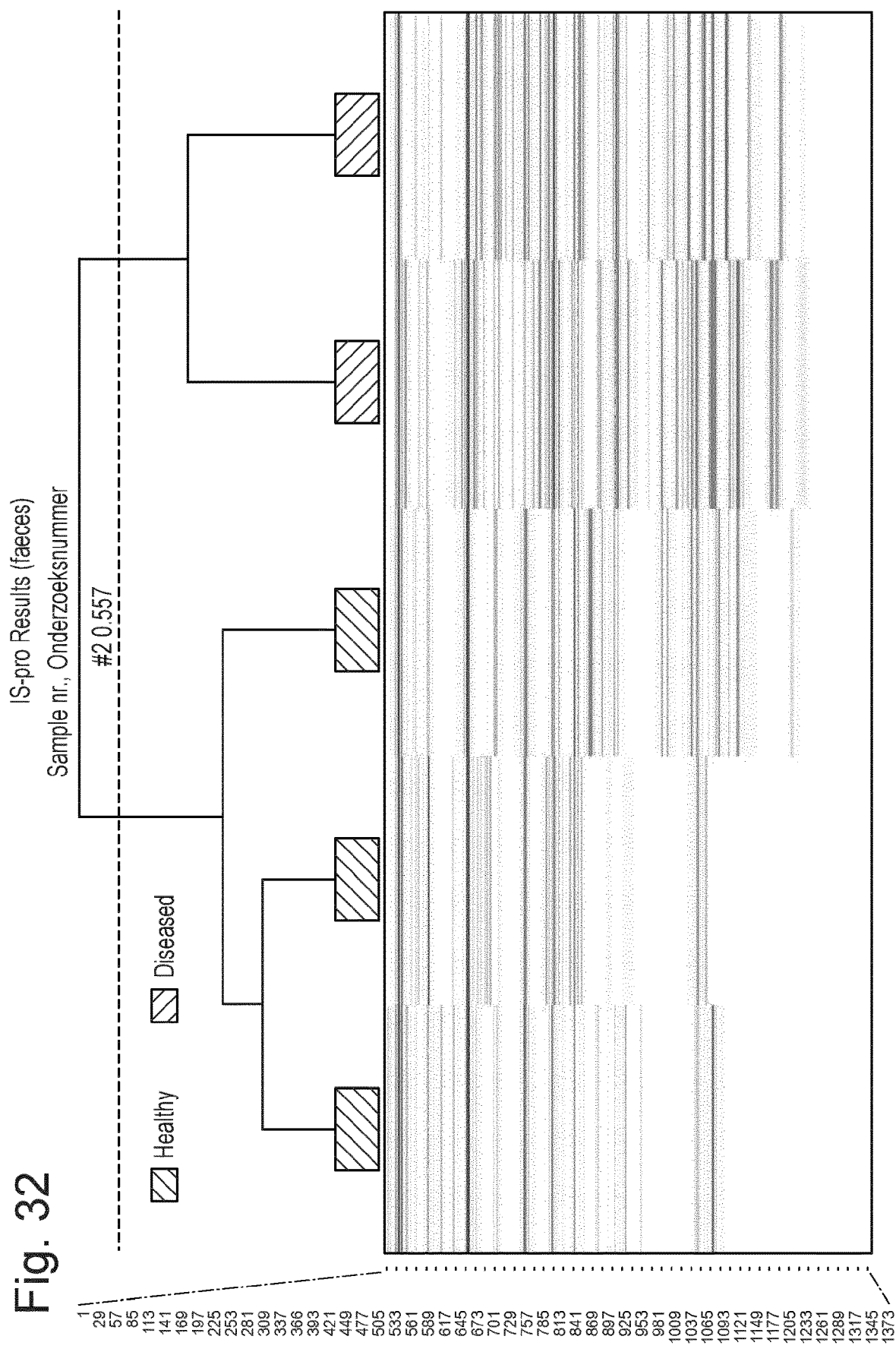
FIG. 32 shows the IS-Pro profile (band view) of fecal samples of Asthma patients and control subjects as described in Example 12.

Fecal samples of two asthma patients were compared to fecal samples of three control subjects using the IS-pro technique as described in the example herein above. The result are depicted in FIG. 31 and FIG. 32. Asthma patients showed a marked increase in diversity of the Proteobacteria group.

Example 13. Testing Vaginal Swab Samples of Bacterial Vaginosis Patients

Figure 33:
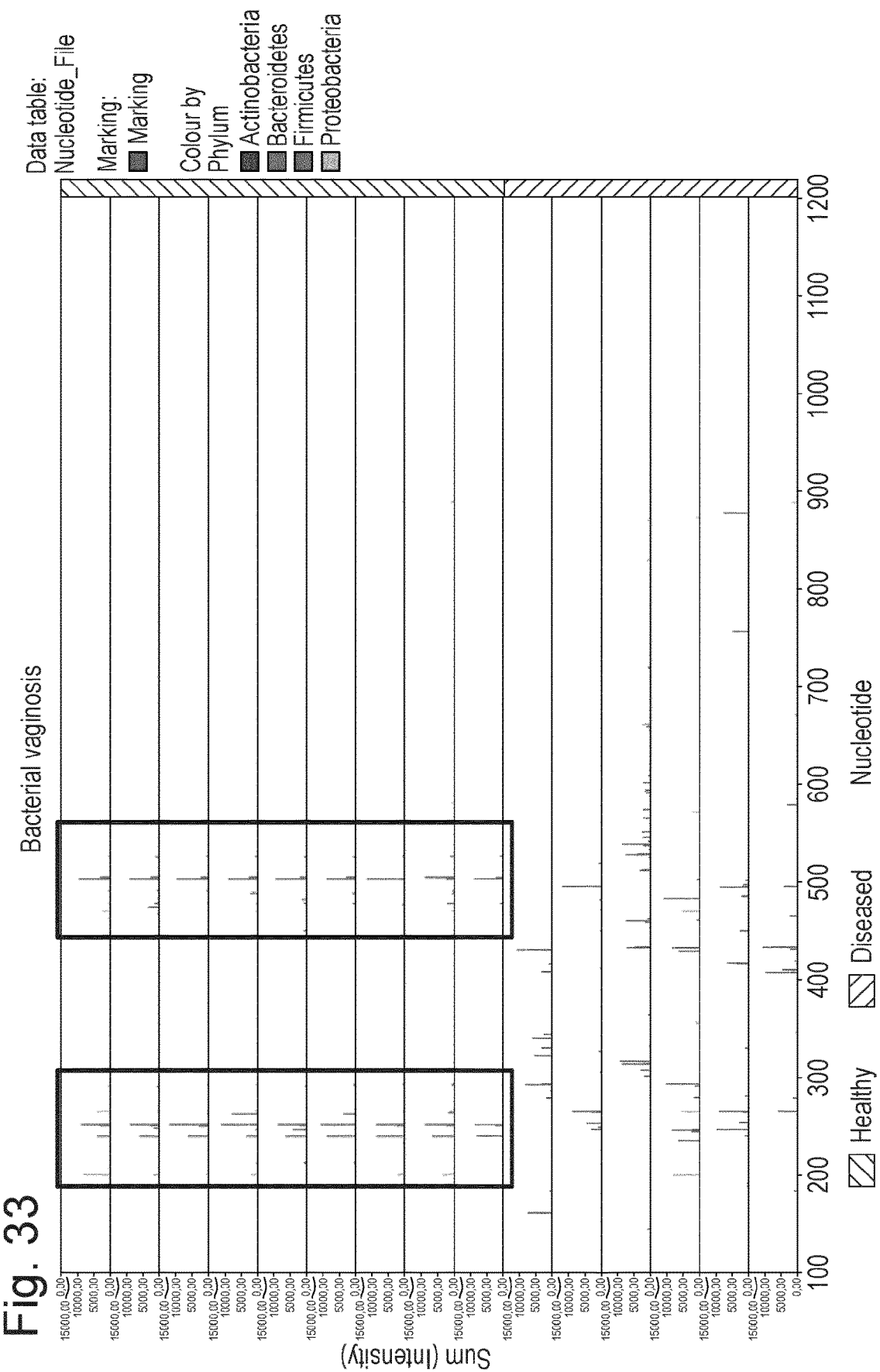
FIG. 33 shows the IS-Pro profile (profile view) of vaginal samples of bacterial vaginosis patients and control subjects as described in Example 13.
Figure 34:
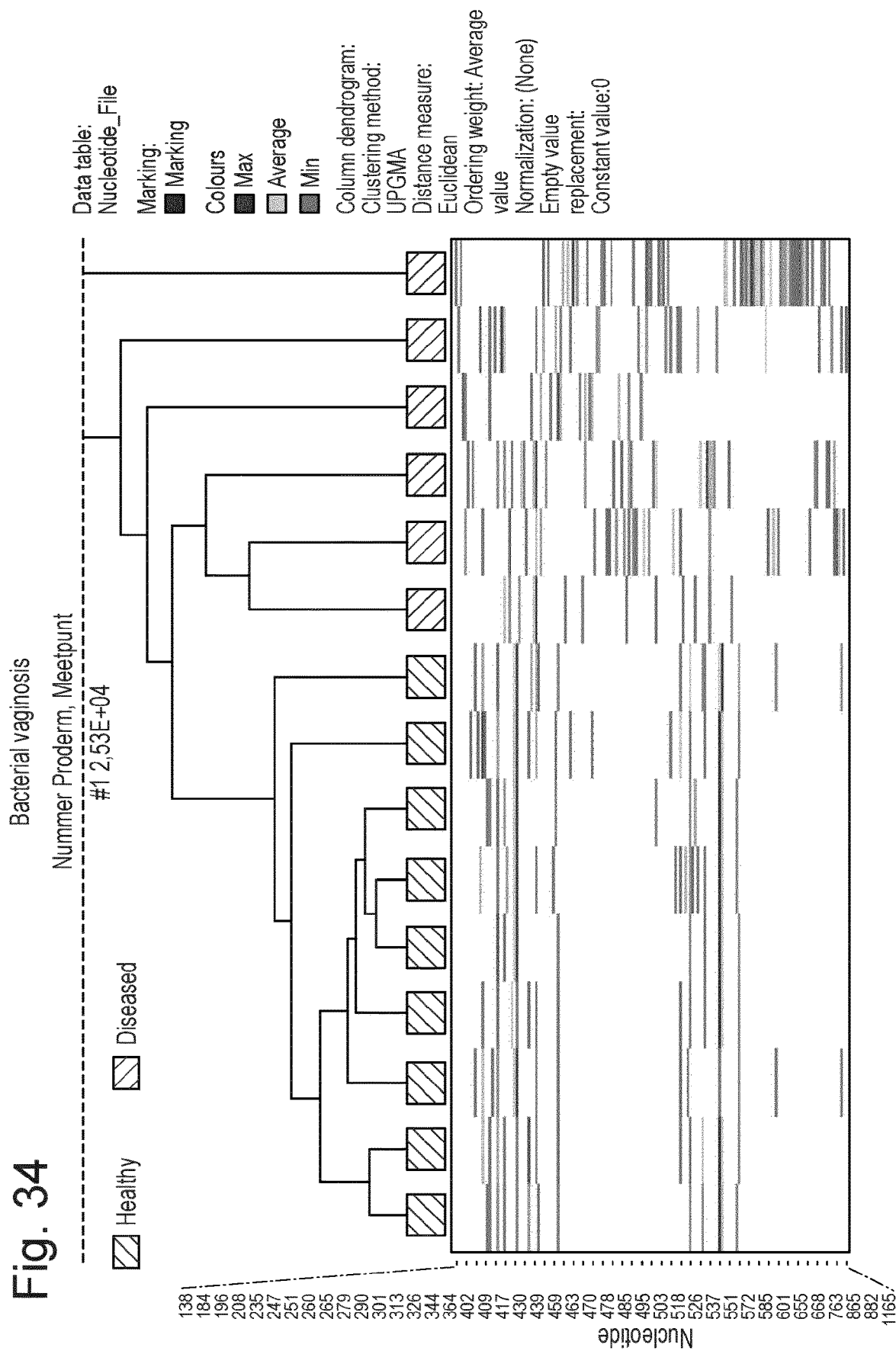
FIG. 34 shows the IS-Pro profile (band view) of vaginal samples of bacterial vaginosis patients and control subjects as described in Example 13.

Vaginal swab samples were obtained from 6 patients suffering from bacterial vaginosis and were compared with samples obtained from 9 control subjects using the IS-pro technique as described in the Examples above. The result are depicted in FIGS. 33 and 34. A clear distinction could be made between the microbiomes of both populations, whereas the marked difference was in the absence in bacterial vaginosis patients of clear bands in the Firmicutes profile at 250, 260 and 520 nucleotides.

Example 14. Testing Fecal Samples of Obstipation Patients

Figure 35:
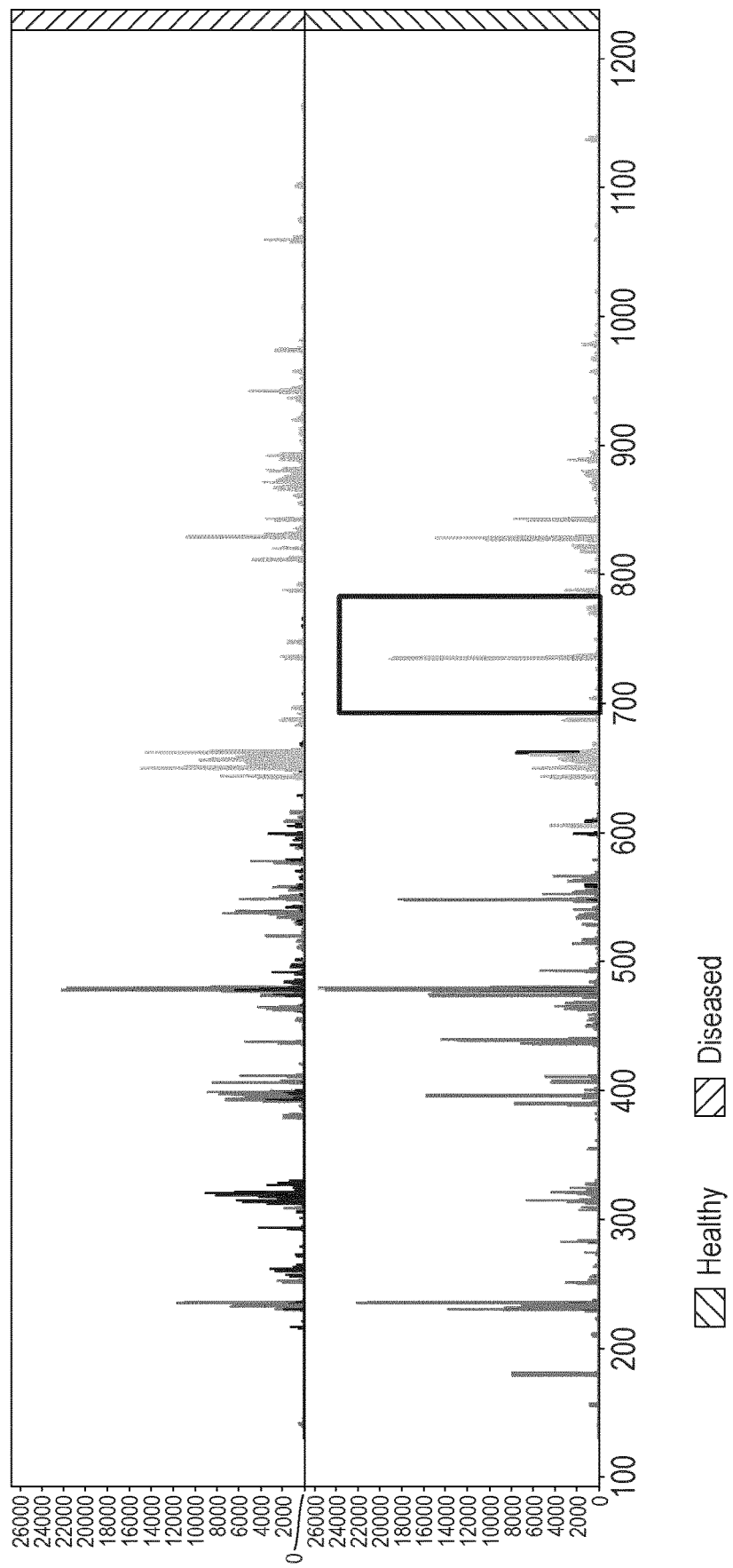
FIG. 35 shows the IS-Pro profile (cumulative profile view) of fecal samples of obstipation patients and control subjects as described in Example 14.
Figure 36:
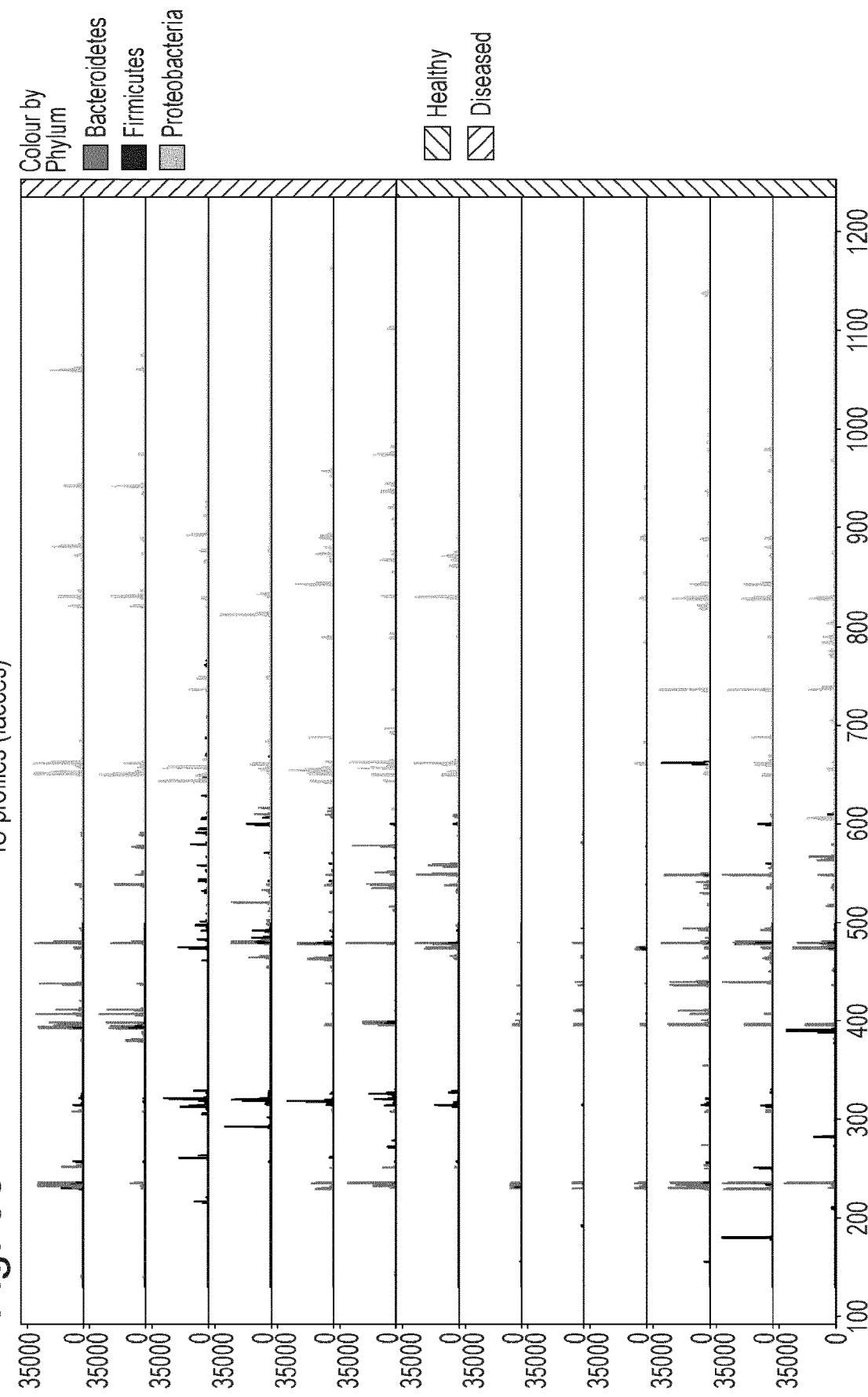
FIG. 36 shows the IS-Pro profile (individual profile view) of fecal samples of obstipation patients and control subjects as described in Example 14.
Figure 37:
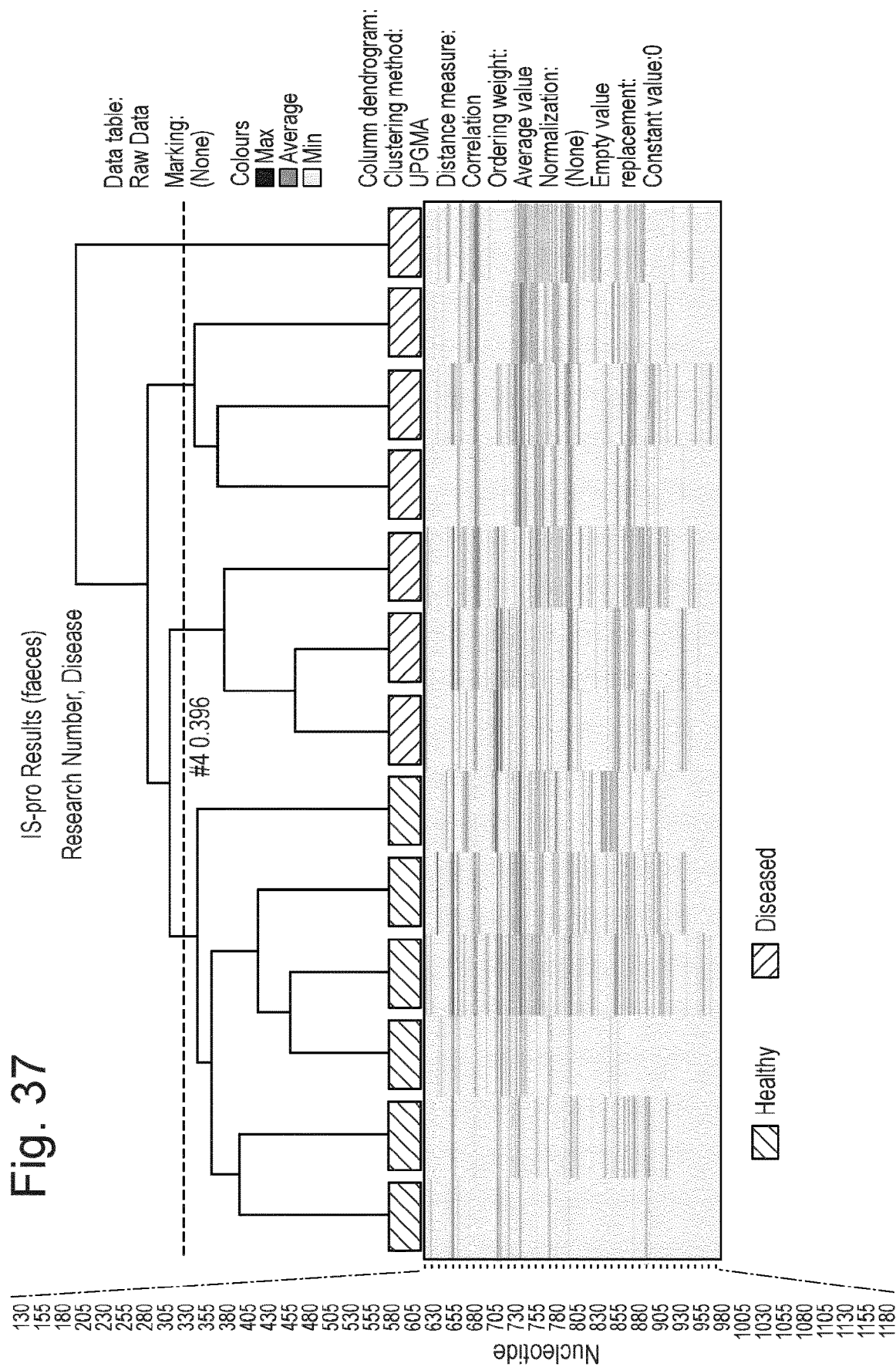
FIG. 37 shows the IS-Pro profile (band view) of fecal samples of obstipation patients and control subjects as described in Example 14.

Fecal samples of patients suffering from obstipation patients were compared with samples of control subjects as described above. The results are depicted in FIGS. 35-37. A clear distinction could be made between the fecal microbiomes of the two populations. The cumulative profile indicated the presence of one or more Proteobacterial species with ITS fragment lengths of around 730 nucleotides was characteristic for the obstipation patients.

Example 15. Testing Fecal Samples of Irritable Bowel Syndrome Patients

Figure 38:
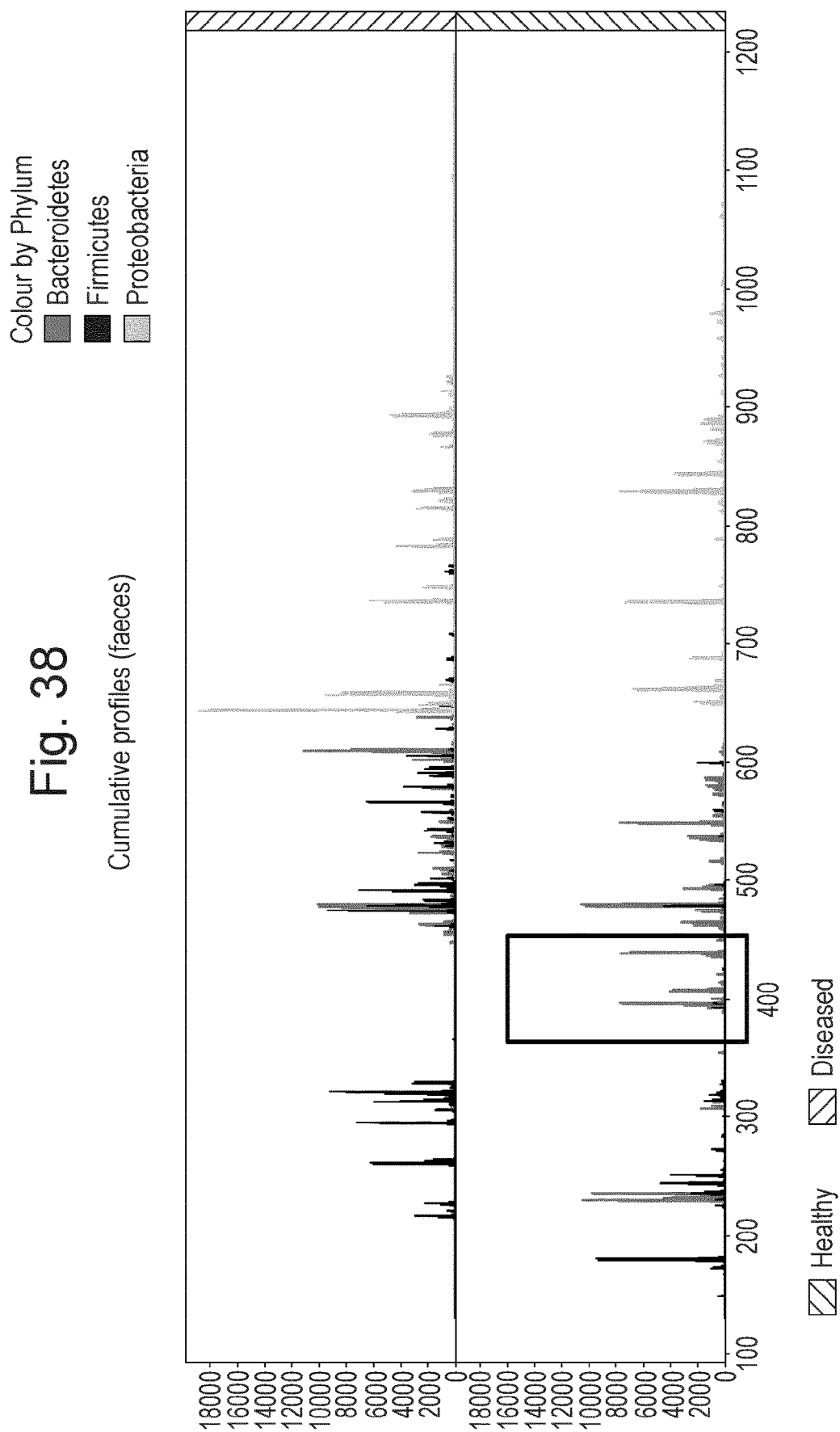
FIG. 38 shows the IS-Pro profile (cumulative profile view) of fecal samples of Irritable Bowel Syndrome patients and control subjects as described in Example 15.
Figure 39:
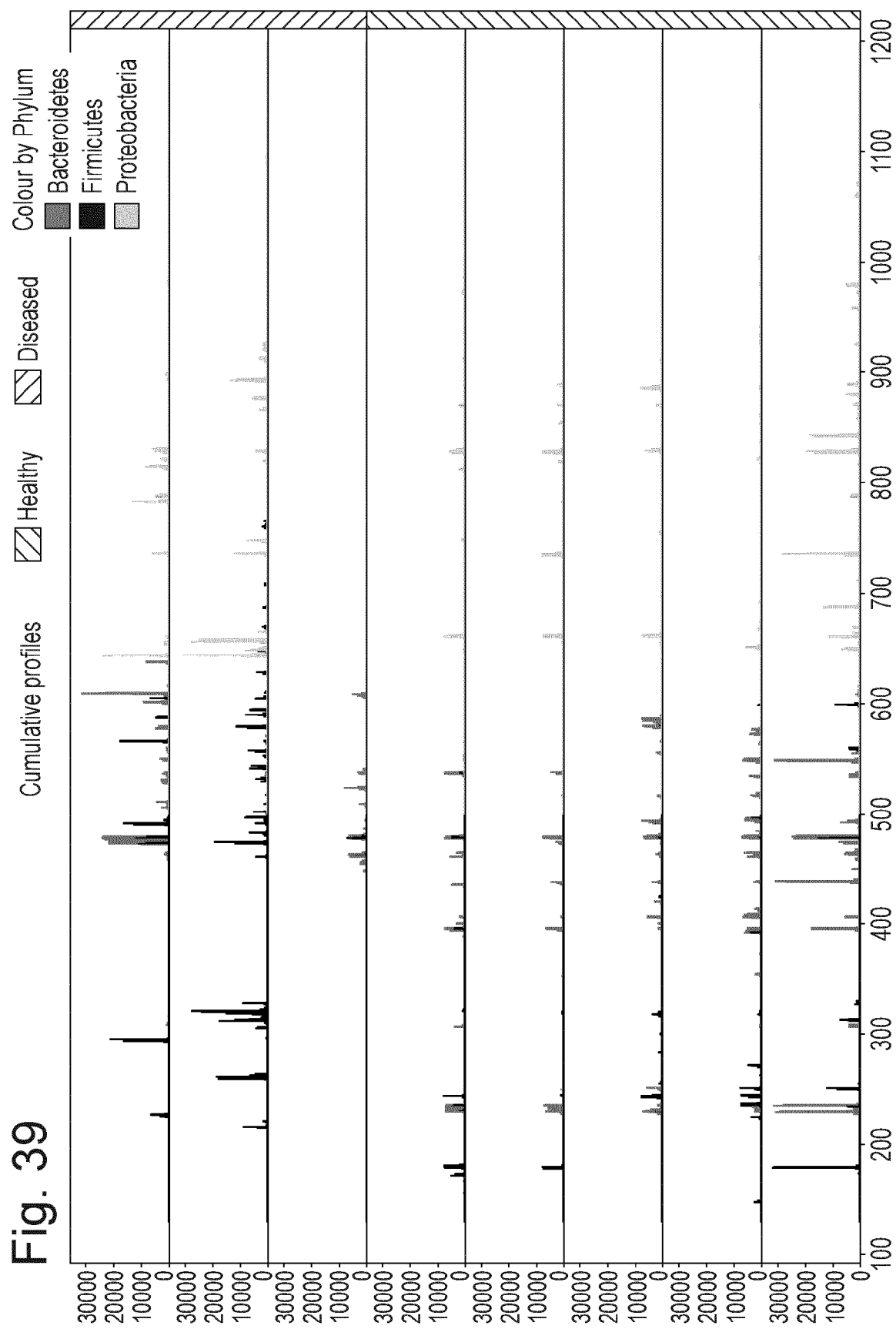
FIG. 39 shows the IS-Pro profile (individual profile view) of fecal samples of Irritable Bowel Syndrome patients and control subjects as described in Example 15.
Figure 40:
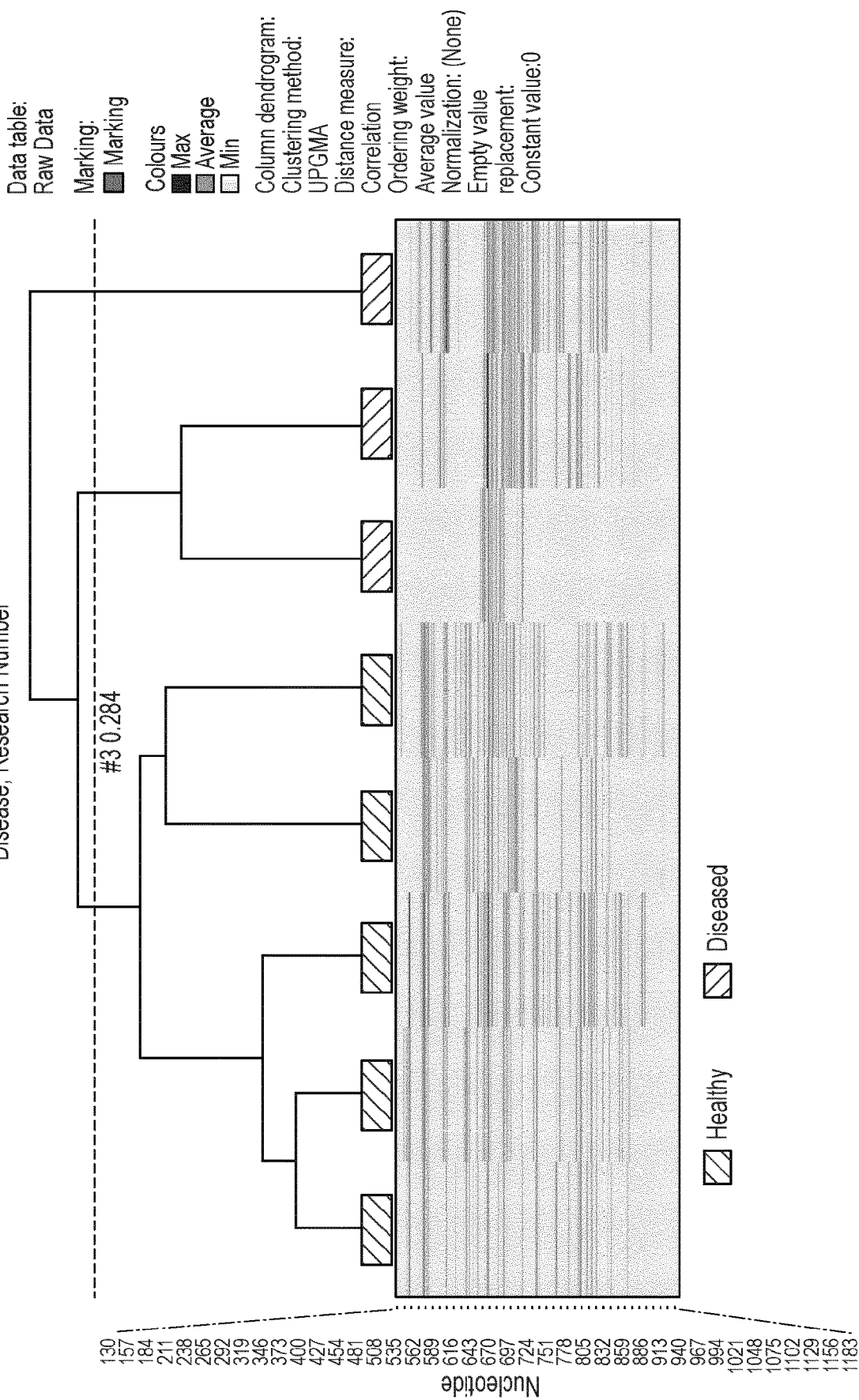
FIG. 40 shows the IS-Pro profile (band view) of fecal samples of Irritable Bowel Syndrome patients and control subjects as described in Example 15.

Fecal samples of patients suffering from patients suffering from Irritable Bowel Syndrome were compared with samples of control subjects as described above. The results are depicted in FIGS. 38-40. A clear distinction could be made between the fecal microbiomes of the two populations. The cumulative profile indicated the presence of several Bacteroidetes species with ITS fragment lengths of around 390-450 nucleotides was characteristic for the Irritable Bowel Syndrome patients.

Example 16. Testing Liquor Samples of Patients Suffering from Meningitis

Figure 41A:
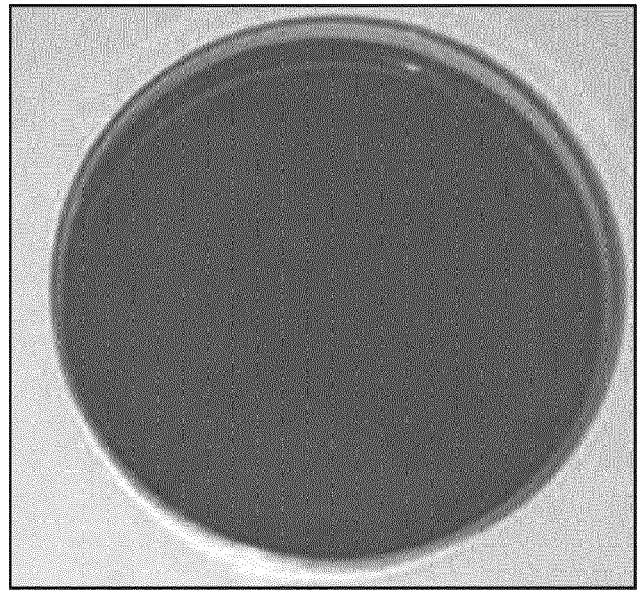
FIG. 41 shows the IS-Pro profile (profile view) of a cerebro-spinal fluid sample of patient suffering from meningitis as described in Example 16. Panel A shows a petri dish following incubation with the liquor sample, exemplifying the culture result wherein no bacterial growth was observed. Panel B shows the IS profile of the liquor sample, indicating the presence of a single bacterial species of the phylum Firmicutes, *Streptococcus mitis*.
Figure 41B:
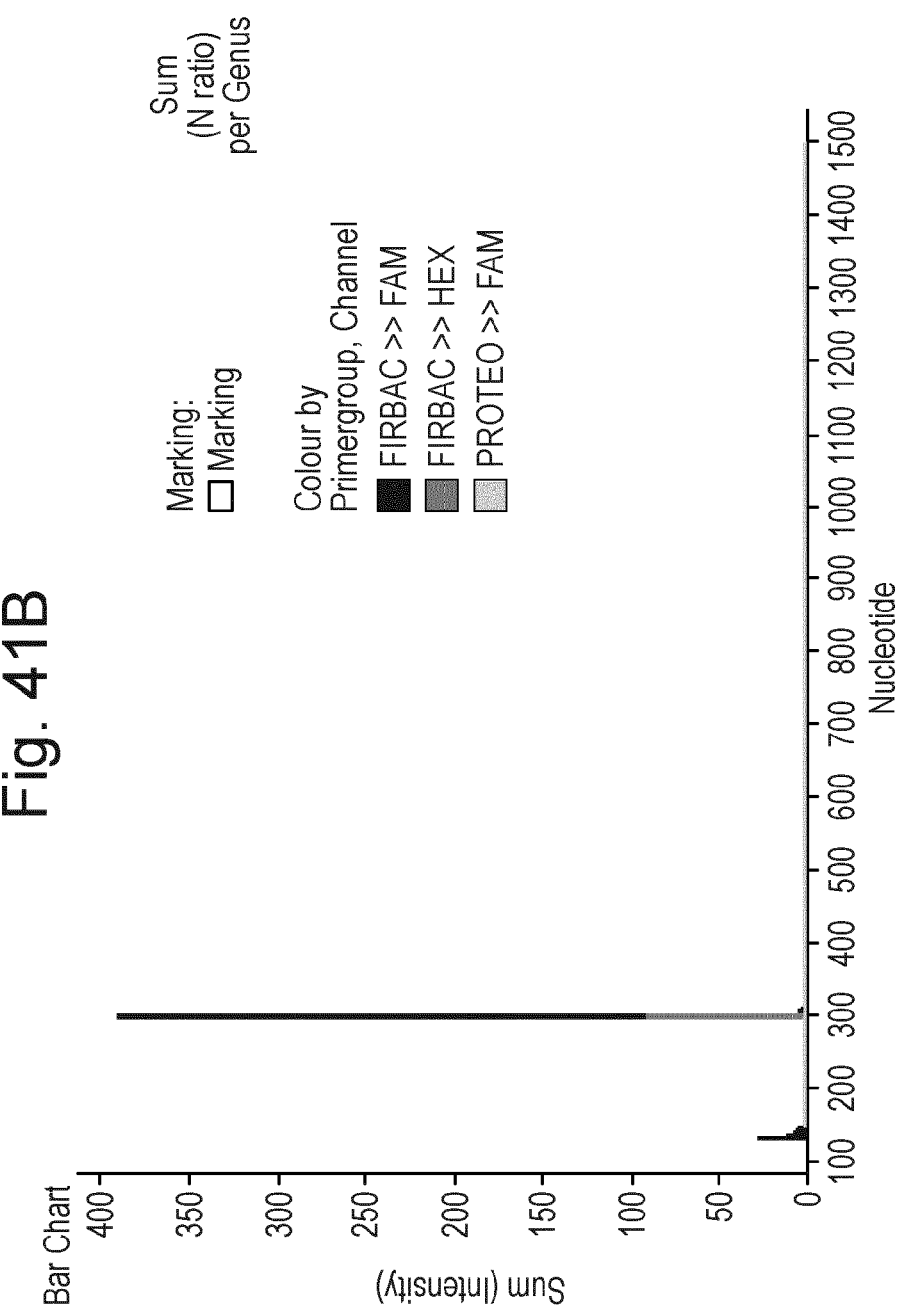

A cerebro-spinal fluid sample of a patient suffering from meningitis was obtained and analysed using the IS-pro techniques as described herein. The sample was also cultivated on standard cultivation media in order to detect the presence of any cultivable bacterium. The results are displayed in FIG. 41. No bacterial growth was observed on solid cultivation media. Panel B shows the IS profile of the liquor sample, indicating the presence of a single bacterial species of the phylum Firmicutes, *Streptococcus mitis*.

Example 17. Testing Fecal Samples of Rheuma Patients

Figure 42:
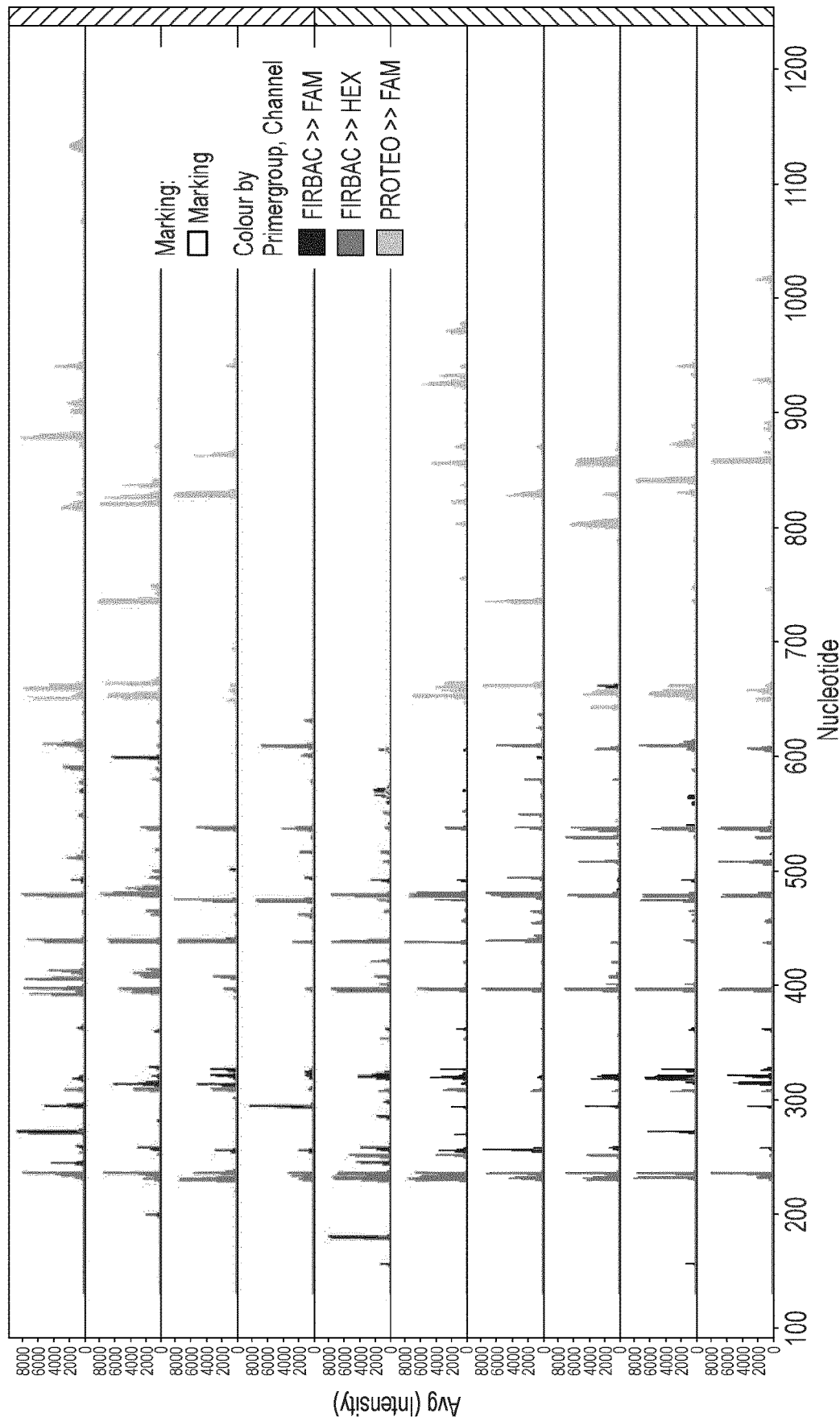
FIG. 42 shows the IS-Pro profile (individual profile view) of fecal samples of Rheuma patients and control subjects as described in Example 17.
Figure 43:
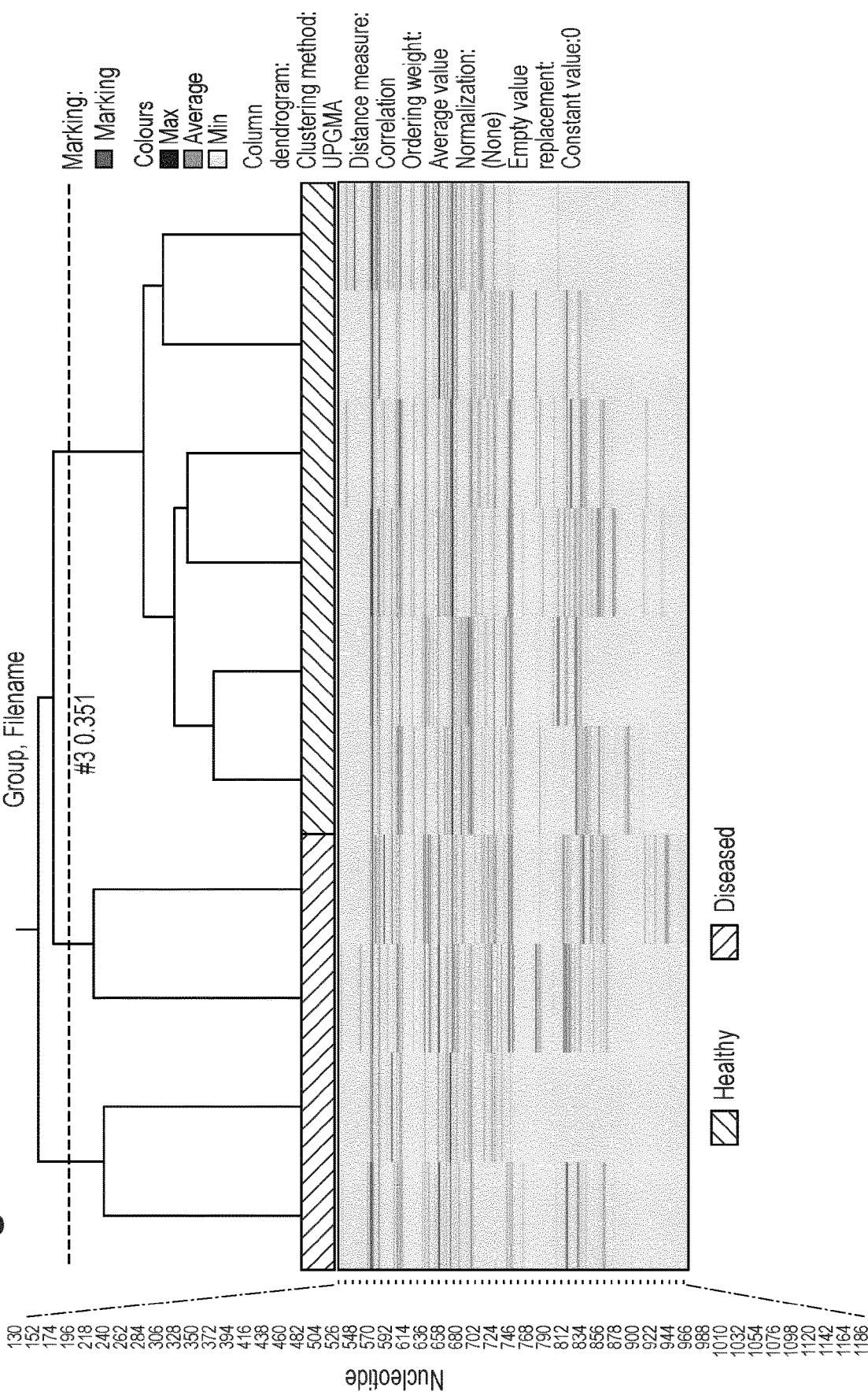
FIG. 43 shows the IS-Pro profile (band view) of fecal samples of Rheuma patients and control subjects as described in Example 17.

Fecal samples of patients suffering from patients suffering from rheuma were compared with samples of control subjects as described above. The results are depicted in FIGS. 42 and 43. Although no marked distinction could be observed in the profile view (FIG. 42), UPGMA clustering could clearly distinguish diseased profiles from healthy profiles (FIG. 43).

Example 18. Testing Fecal Samples of Prematurely Born Children Having Necrotising Enterocolitis (NEC)

Necrotizing enterocolitis is an intestinal disorder of prematurely born children, characterized by an acute necrosis of portions of the bowel. The disease has a high mortality rate. Fecal samples of patients suffering from Necrotising Enterocolitis were compared with samples of control subjects as described above. The results are depicted in FIG. 44. With a method according to the invention, we can predict at least up to 3 days in advance which children will develop this disease, enabling doctors to potentially prevent the occurrence of the disease before its full onset.

Figure 44B:
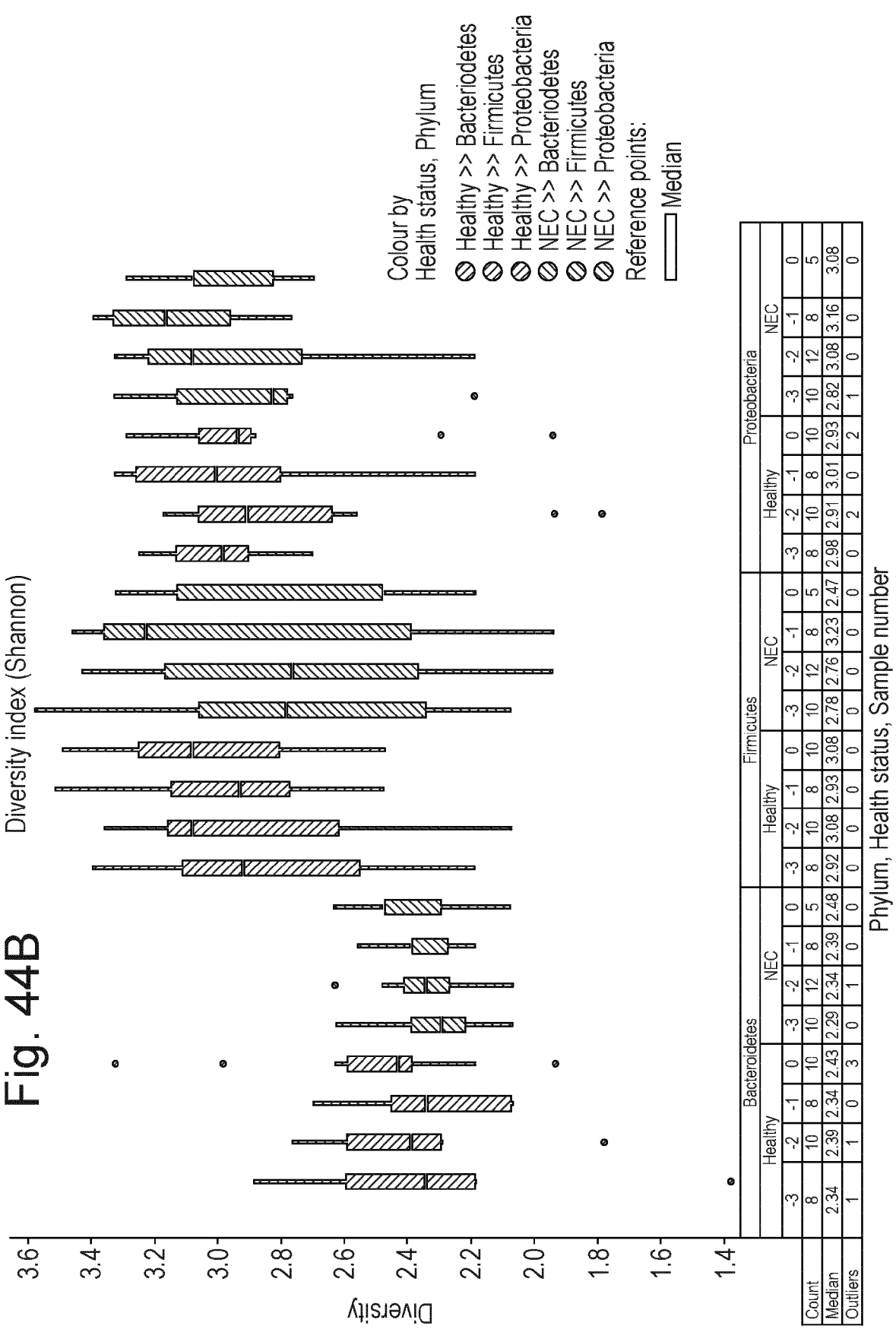
FIG. 44B shows boxplot comparisons of within-sample diversity as calculated by Shannon index (per phylum) for Necrotising Enterocolitis (NEC) patients and control subjects for the experiment as described in Example 18.

Diagnosis is made by assessing the absence or presence of specific peaks or by applying machine learning algorithms on whole profiles such as Support Vector Machines, Random Forest or partial least squares discriminant analysis (ROC curve; FIG. 44C). It was found (FIG. 44B) that in samples of Necrotising Enterocolitis (NEC) patients, the abundance and/or species diversity in the phylum of Firmicutes decreased as compared to the healthy control population, while the abundance and/or species diversity (as indicated by the Shannon Diversity Index) in the phylum of Proteobacteria had increased as compared to the healthy control population.

By making an early diagnosis based on microbiota content as described herein, a directed treatment can be applied, either by modulating the microbiota towards a healthy state or by suppressing the host response.

Example 19. Testing Fecal Samples of Neonates Having Sepsis

Figure 45A:
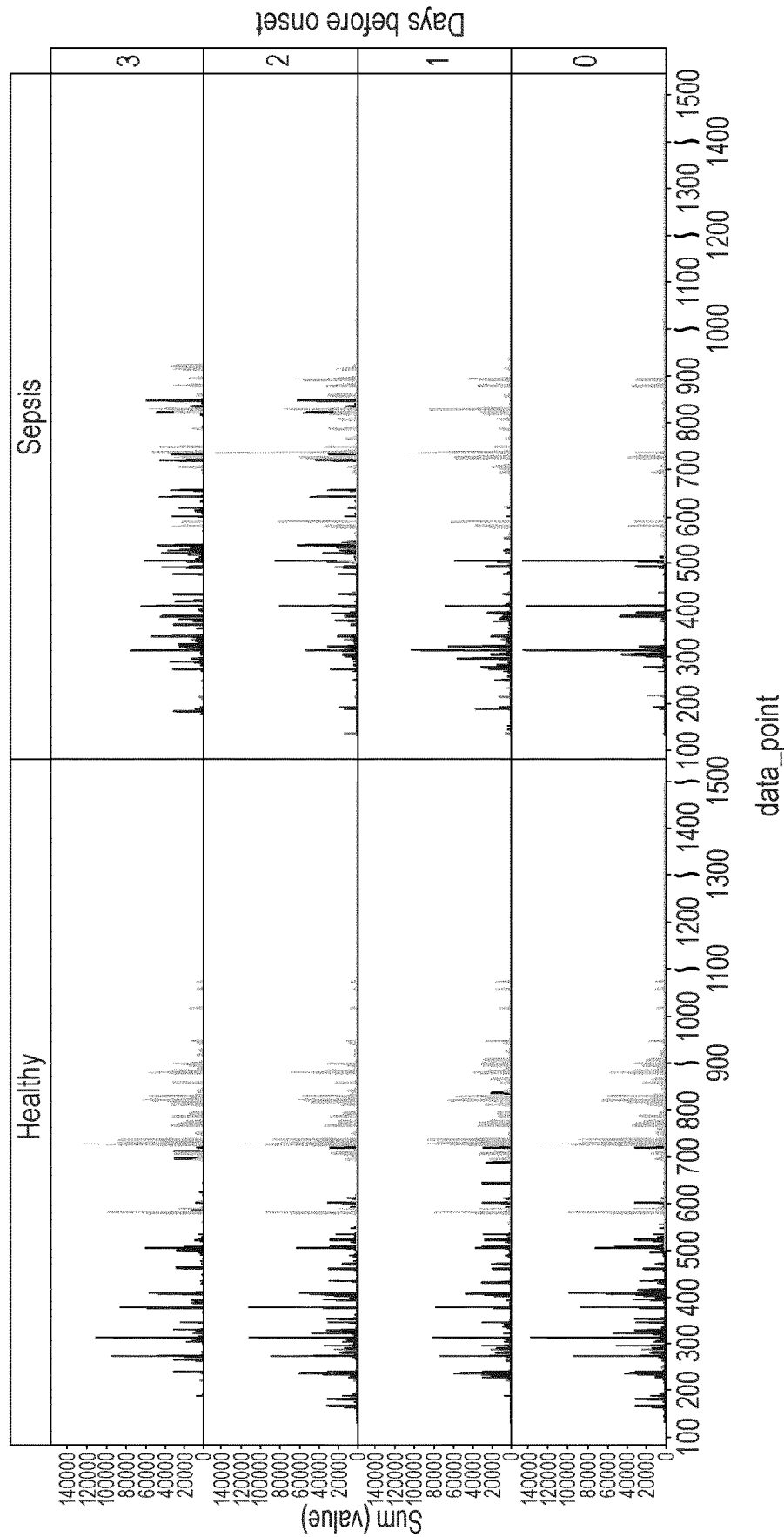
FIG. 45A shows the IS-Pro profile (individual profile view) of fecal samples of sepsis patients and control subjects as described in Example 19.
Figure 45C:
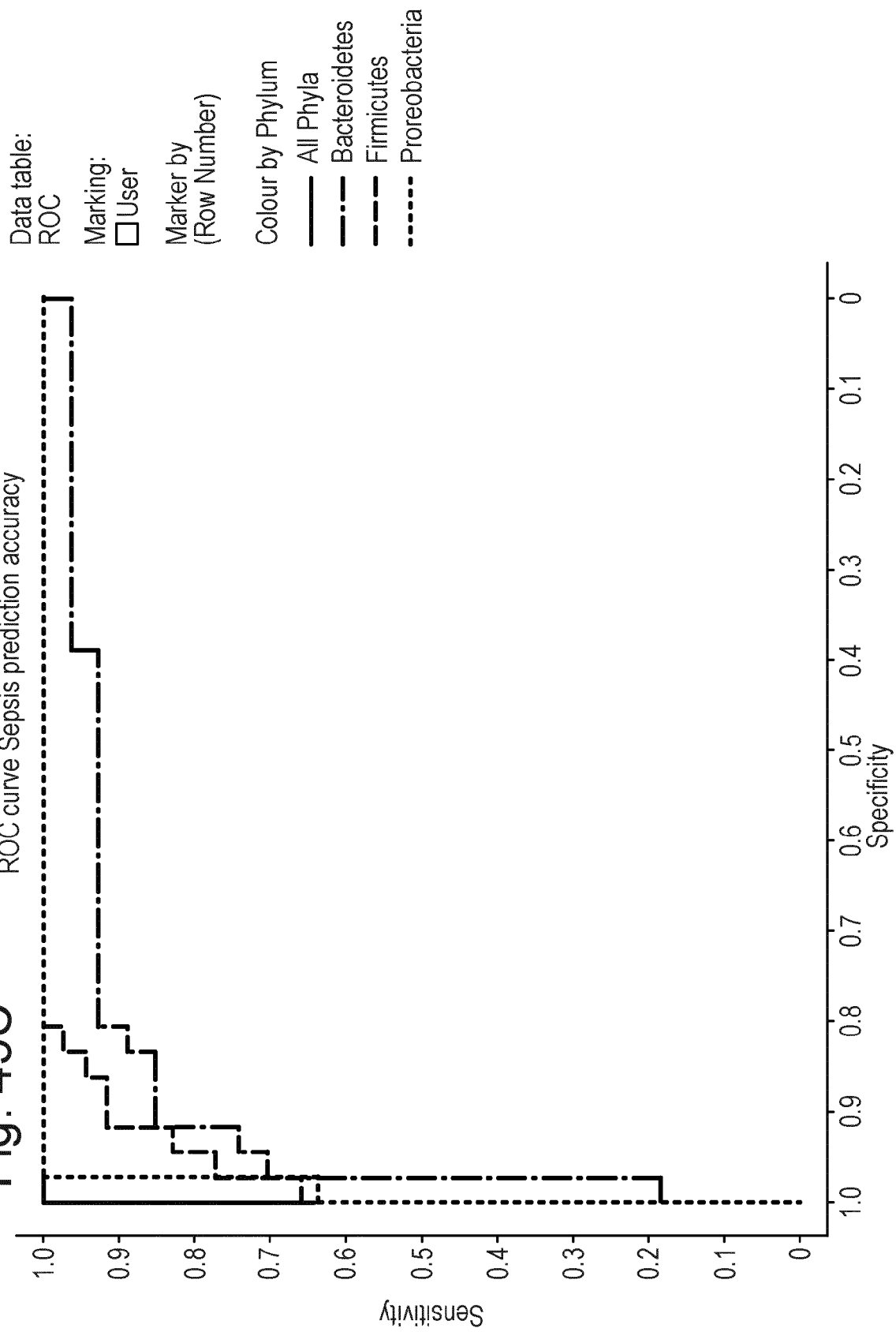
FIG. 45C shows ROC curves summarizing the predictive power of a PLS-DA model for clinical status per phylum and for all phyla combined. As evidenced by the Figures differences between patients and control subjects in all tested phyla, i.e. Bacteroidetes, Firmicutes and Proteobacteria are exploited to diagnose, monitor and predict sepsis.

Newborn babies, especially those that are prematurely born and/or are admitted to a hospital have a high risk of developing sepsis. Fecal samples of patients suffering from sepsis were compared with samples of control subjects as described above. The results are depicted in FIG. 45. With a method according to the invention, sepsis can be predicted at least three days in advance by monitoring of the intestinal microbiota. It is seen that changes between healthy and diseased patients occur in specific peaks (e.g. those belonging to *Staphylococcus epidermidis*) or at the phylum level (lower abundance or diversity of Proteobacteria, Bacteroidetes, Firmicutes or Actinobacteria), or at the profile level. At the profile level, samples can be categorized by e.g. machine learning algorithms as mentioned above. As the causative pathogen can be identified in the microbiota profile (here: *Staphylococcus epidermidis*), a directed antibiotic therapy against that particular pathogen can be initiated before it causes sepsis.

Example 20. Testing Fecal Samples of *Clostridium Difficile* Associated Diarrhea Patients

Figure 46:
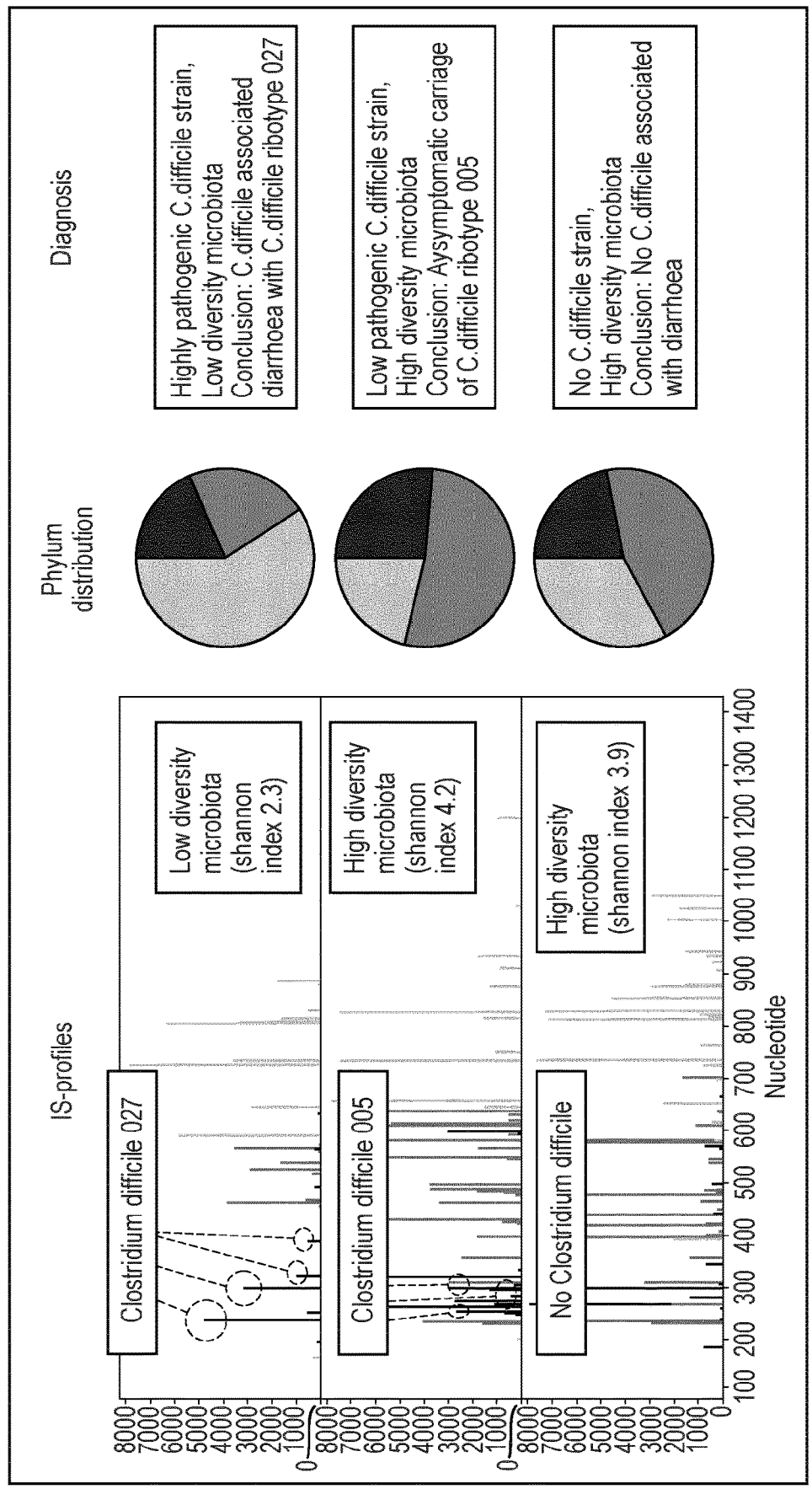
FIG. 46 shows the result of diagnosis of *Clostridium difficile* infection in the intestinal tract of (from top to bottom) infected and diseased patients, asymptomatic carriers and healthy (no *C. difficile*) subjects having diarrhoea. Displayed are (from left to right) the IS-pro profiles, the Phylum distribution (red: Bacteroidetes; yellow: Proteobacteria; bleu: Firmicutes), and the Diagnosis. Clearly visible is the low population diversity as indicated by a low Shannon index in diarrhoea patients suffering from infection with a pathogenic *C. difficile* strain, while asymptomatic carriers of a low pathogenic *C. difficile* strain and healthy subjects maintain Shannon index diversities above 3. Hence, subject having been diagnosed with a low overall population diversity in combination with *C. difficile* infection may benefit from fecal microbiota transplantation (FMT; e.g. as described by Bakken et al 2011, Clin Gastroenterol Hepatol. 9(12): 1044-1049), rather than antibiotic treatment alone, while diarrhoea patients having a high overall population diversity in combination with *C. difficile* infection may benefit from antibiotic treatment.

*Clostridium Difficile* Associated Diarrhea is a disease typically afflicting hospitalized patients with previous or ongoing exposure to antibiotics. The disease has a high morbidity, and specific pathogenic strains may also give a high mortality rate (e.g. *C. difficile* ribotype 027). It has been postulated that *Clostridium difficile* can only cause diarrhoea when the rest of the microbiota has a diminished diversity (caused by antibiotics). With a method according to the invention, we can identify *Clostridium difficile* in fecal samples up to the strain level and at the same time measure the diversity of the fecal microbiota (FIG. 46). By combining this information, we can come to an accurate diagnosis, providing doctors with information on the presence of *Clostridium difficile*, the strain type and the status of the microbiota, which taken together determines the diagnosis and treatment modality: when microbiota is severely depleted, a choice could be made for microbial supplementation therapy (e.g. fecal transplantation), when microbiota is less depleted, a conventional antibiotics therapy could be given, while no therapy should be given if *Clostridium difficile* is not found. Finally, the effect of therapy can be monitored: whether bacterial suppletion (e.g. FMT) therapy is successful, whether antibiotic therapy is not depleting the microbiota and other effects.

The invention claimed is:
1. A method for providing a test signature of a microbiome, the method comprising the steps of:
   a) providing a sample of genomic DNA from a population of microorganisms in said microbiome;
   b) performing a PCR amplification reaction on said sample of genomic DNA using PCR amplification primers directed to flanking conserved DNA regions of 16S-23S rRNA internal transcribed spacer (ITS) regions to thereby amplify and provide amplification products of said 16S-23S rRNA ITS regions; and
   c) analyzing said amplification products based on length differences in said amplification products to thereby provide a test signature of the composition of the population of microorganisms in said microbiome;
   wherein said PCR amplification primers comprise:
      (i) a set of PCR amplification primers for amplifying at least one 16S-23S rRNA ITS region in the genomic DNA of microorganisms belonging to the phylum Firmicutes, and
      (ii) a set of PCR amplification primers for amplifying at least one 16S-23S rRNA ITS region in the genomic DNA of microorganisms belonging to the phylum Bacteroidetes, and
      (iii) a set of PCR amplification primers for amplifying at least one 16S-23S rRNA ITS region in the genomic DNA of microorganisms belonging to the phylum Proteobacteria, wherein said set of PCR amplification primers for amplifying the at least one 16S-23S rRNA ITS region in the genomic DNA of the phylum Proteobacteria comprises SEQ ID NO:_6 as a forward primer; and at least one reverse primer selected from the group consisting of
         5'-AATCTCGGTTGATTTCTTTTCCT-3' (SEQ ID NO: 7),
         5'-AATCTCGGTTGATTTCTTCTCCT-3' (SEQ ID NO: 8),
         5'-AATCTCTTTTGATTTCTTTTCCTCG-3' (SEQ ID NO: 9),
         5'-AATCTCATTTGATGTCTTTTCCTCG-3' (SEQ ID NO: 10),
         5'-AATCTCTTTTGATTTCTTTTCCTTCG-3' (SEQ ID NO: 11),
         5'-AATCTCTCTTGATTTCTTTTCCTTCG-3' (SEQ ID NO: 12), and
         5'-AATCTCAATTGATTTCTTTTCCTAAGG-3' (SEQ ID NO: 13); and
      wherein at least one of said primers comprises a fluorescent label.

2. The method of claim 1, wherein said PCR amplification primers further comprise:
   a) forward primer 5'-CTGGATCACCTCCTTTCTAWG-3' (SEQ ID NO: 1) comprising a first fluorescent label;
   b) forward primer 5'-CTGGAACACCTCCTTTCTGGA-3' (SEQ ID NO: 2) comprising a fluorescent label; and
   c) three unlabeled reverse primers consisting of the sequences of 5'-AGGCATCCACCGTGCGCCCT-3' (SEQ ID NO: 3); 5'-AGGCATTCACCRTGCGCCCT-3' (SEQ ID NO: 4); and 5'-AGGCATCCRCCATGCGCCCT-3' (SEQ ID NO: 5).

3. The method of claim 1, wherein said microbiome is a microbiome selected from the group consisting of the respiratory tract, oral cavity, skin, gastrointestinal tract, urogenital tract, urine, saliva, sputum, pus, wound fluid, feces, a human body, soil, waterbodies, and plants.

4. The method of claim 1, wherein said microbiome is selected from the group consisting of
   a) an intestinal microbiome of a subject suffering or suspected of suffering from a digestive tract or gastrointestinal disorder, a systemic disease or from a skin disorder,
   b) a skin microbiome of a subject suffering from a skin disorder,
   c) a wound microbiome of a subject suffering from a chronic wound, a microbiome from a diabetic ulcer, or a microbiome from an ulcer associated with vascular disease,
   d) a urogenital tract microbiome or a microbiome from vaginal flora of a female having low fertility or having a low probability of success of an in vitro fertilization or embryo transfer procedure, or suffering from bacterial vaginosis,
   e) an oral microbiome of a subject suffering from an oral, nasal or oropharyncheal disorder, or a microbiome from subject suffering from periodontitis, periimplantitis, or oro-nasopharyngeal carcinoma,
   f) a pulmonary microbiome in a pulmonary sample selected from the group consisting of bronchoalveolar lavage, a sputum sample, and a lung biopsy of a subject suffering from a disorder that affects the upper or lower respiratory tract, and
   g) a microbiome in a liquor sample, a pleural sample, a blood sample, a urine sample, an abscess sample, or a tissue sample of an organ in a subject suspected of suffering from a microbial infection.

5. The method of claim 4,
   wherein the digestive tract or gastrointestinal disorder is selected from the group consisting of inflammatory bowel disease, diverticulitis, irritable bowel syndrome, coeliac, lactose intolerance, Necrotising Enterocolitis, *Clostridium Difficile* Associated Diarrhea, colorectal cancer, and a comorbid disorder selected from the group consisting of attention-deficit/hyperactivity disorder, obsessive compulsive disorder, anxiety, stress, eating disorder, major depressive disorder, bipolar disorder, depression, and schizophrenia;
   wherein the systemic disease is selected from the group consisting of arthritis, sarcoidosis, mixed connective tissue disease, spondylitis ankylopoetica, osteoporosis, juvenile idiopathic arthritis, osteoarthritis, rheumatoid arthritis, Behcet's disease, Sjögren's syndrome, fibromyalgia, sclerodermia, Raynaud's phenomenon, sepsis, and systemic lupus erythematosus;
   wherein the skin disorder is selected from the group consisting of psoriasis, eczema, acne, and rosacea; or
   wherein the disorder that affects the upper or lower respiratory tract is selected from the group consisting of respiratory infection, chronic obstructive pulmonary disease, asthma, cystic fibrosis, and lung cancer.

6. The method of claim 1, wherein steps b) and c) of said method comprise the steps of:
   b1) providing a PCR calibrator system, comprising a set of PCR amplification primers at least one of which comprises a label, and a set of at least two PCR calibrators, each PCR calibrator consisting of a DNA fragment comprising a spacer region having a DNA sequence of a given length flanked by upstream and downstream adapter DNA sequences that comprise primer binding sites for binding of said PCR amplification primers, wherein said PCR amplification primers are for PCR amplifying the spacer region DNA sequence of all PCR calibrators in said set of at least two PCR calibrators, wherein the spacer region DNA sequence comprised in each of said PCR calibrators in said set of at least two PCR calibrators is of a different length, and wherein each PCR calibrator in said set of at least two PCR calibrators is present in an equal amount or in a known amount relative to other PCR calibrators in said set;

b2) adding said set of at least two PCR calibrators from said PCR calibrator system to said sample of genomic DNA;

b3) performing a PCR amplification reaction on said sample of genomic DNA comprising said set of at least two PCR calibrators using said PCR amplification primers from said PCR calibrator system as a first set of amplification primers to amplify and provide amplification products of said spacer region DNA sequence comprised in said set of at least two PCR calibrators, and using at least a second set of PCR amplification primers directed to said flanking conserved DNA regions to thereby co-amplify and provide amplification products of said 16S-23S rRNA ITS regions comprised in said sample of genomic DNA;

b4) providing a standard curve by determining the PCR amplification efficiency of each of said at least two PCR calibrators from said PCR calibrator system in said PCR amplification reaction of step b3) and expressing said PCR amplification efficiency as a function of the length of the DNA sequence of the 16S-23S rRNA ITS regions;

b5) determining the length-specific amplification efficiency for said 16S-23S rRNA ITS regions of different length comprised in said genomic DNA sample and amplified in step b3) using the standard curve as provided in step b4);

b6) determining the abundance of said 16S-23S rRNA ITS regions of different length in said microbiome using the length-specific amplification efficiencies determined in step b5), and c) analyzing the composition of said population of microorganisms based on the abundance of said 16S-23S rRNA ITS regions of different length determined in step b6) to thereby provide a test signature of the composition of the population of microorganisms in said microbiome.

7. The method of claim 6, wherein said standard curve is based on at least five PCR calibrators of different length ranging in length from 50 to 1200 bps.

8. A method for analyzing a microbiome, comprising analyzing the composition of a population of microorganisms in said microbiome based on taxonomic variation in the DNA sequence of microbial 16S-23S rRNA internal transcribed spacer (ITS) regions in the genomic DNA of said microorganisms, wherein the sequences of conserved DNA regions comprised in the 16S and 23S rRNA sequences flanking said ITS regions in the genome of said microorganisms comprise primer binding sites for amplification of said ITS regions, said analyzing comprising the steps of:

a) providing a sample of genomic DNA from the microorganisms in said microbiome;

b) performing a PCR amplification reaction on said sample of genomic DNA using at least one set of PCR amplification primers directed to said flanking conserved DNA regions to thereby amplify and provide amplification products of said ITS regions comprised in said genomic DNA sample;

c) analyzing said amplification products based on length differences in said amplification products to thereby provide a test signature of the composition of the population of microorganisms in said microbiome; and d) comparing said test signature with at least one reference signature of a desirable microbiome and/or with at least one reference signature of an undesirable microbiome, wherein said at least one set of PCR amplification primers comprises:

a set of PCR amplification primers for amplifying the 16S-23S rRNA internal transcribed spacer (ITS) regions in the genomic DNA of microorganisms belonging to the phylum Firmicutes, a set of PCR amplification primers for amplifying the 16S-23S rRNA internal transcribed spacer (ITS) regions in the genomic DNA of microorganisms belonging to the phylum Bacteroidetes, and a set of PCR amplification primers for amplifying the 16S-23S rRNA internal transcribed spacer (ITS) regions in the genomic DNA of microorganisms belonging to the phylum Proteobacteria, wherein said set of PCR amplification primers for amplifying the 16S-23S rRNA internal transcribed spacer (ITS) regions in the genomic DNA of the phylum Proteobacteria comprises:

i) SEQ ID NO: 6 as a forward primer; and ii) at least one reverse primer selected from the group consisting of

5'-AATCTCGGTTGATTTCTTTTCCT-3' (SEQ ID NO: 7),

5'-AATCTCGGTTGATTTCTTCTCCT-3' (SEQ ID NO: 8),

5'-AATCTCTTTTGATTTCTTTTCCTCG-3' (SEQ ID NO: 9),

5'-AATCTCATTTGATGTCTTTTCCTCG-3' (SEQ ID NO: 10),

5'-AATCTCTTTTGATTTCTTTTCCTTCG-3' (SEQ ID NO: 11),

5'-AATCTCTCTTGATTTCTTTTCCTTCG-3' (SEQ ID NO: 12), and

5'-AATCTCAATTGATTTCTTTTCCTAAGG-3' (SEQ ID NO: 13); and wherein at least one of said primers comprises a fluorescent label.

9. The method of claim 8, wherein said comparing of said test signature with at least one reference signature of a desirable microbiome and/or with at least one reference signature of an undesirable microbiome is performed by clustering of ITS profiles, and classifying the test signature as a signature of a desirable microbiome or as a signature of an undesirable microbiome.

10. A method of analyzing the composition of a microbiome based on taxonomic variation in the DNA sequence of the microbial 16S-23S rRNA internal transcribed spacer (ITS) regions in the genomic DNA of the microorganisms in said microbiome, wherein the sequences of conserved DNA regions comprised in the 16S and 23S rRNA sequences flanking said ITS regions in the genomic DNA of said microorganisms comprise primer binding sites for amplification of said ITS regions, said method comprising the steps of:

a) providing a sample of genomic DNA from the microbiome;

b) providing a PCR calibrator system, comprising a set of PCR amplification primers at least one of which comprises a label, and a set of at least two PCR calibrators, each PCR calibrator consisting of a DNA fragment comprising a spacer region having a DNA sequence of a given length flanked by upstream and downstream adapter DNA sequences that comprise primer binding sites for binding of said PCR amplification primers, wherein said set of PCR amplification primers is for PCR amplifying the spacer region DNA sequence of all PCR calibrators in said set of at least two PCR calibrators, wherein the spacer region DNA sequence comprised in each of said PCR calibrators in said set of at least two PCR calibrators is of a different length, and wherein each PCR calibrator in said set of at least two PCR calibrators is present in an equal amount or in a known amount relative to other PCR calibrators in said set;

c) adding said set of at least two PCR calibrators from said PCR calibrator system to said sample of genomic DNA;

d) performing a PCR amplification reaction on said sample of genomic DNA comprising said set of at least two PCR calibrators using said set of PCR amplification primers from said PCR calibrator system as a first set of amplification primers to amplify and provide amplification products of said spacer region DNA sequences comprised in said set of at least two PCR calibrators, and using at least a second set of PCR amplification primers directed to said flanking conserved DNA regions to thereby co-amplify and provide amplification products of said ITS regions comprised in said sample of genomic DNA, e) providing a standard curve by determining the PCR amplification efficiency of each of said at least two PCR calibrators from said PCR calibrator system in said PCR amplification reaction of step d) and expressing said PCR amplification efficiency as a function of the length of the DNA sequence of the ITS region;

f) determining the length-specific amplification efficiency for ITS regions of different length comprised in said genomic DNA sample and amplified in step d) using the standard curve as provided in step e);

g) determining the abundance of microbial 16S-23S rRNA internal transcribed spacer (ITS) regions of different length in said microbiome using the length-specific amplification efficiencies determined in step f), and h) analyzing the composition of the population of microorganisms based on the abundances of ITS regions of different length determined in step g);

wherein said second set of PCR amplification primers comprises a set of PCR amplification primers for amplifying the 16S-23S rRNA internal transcribed spacer (ITS) regions in the genomic DNA of microorganisms belonging to the phylum Proteobacteria, wherein said set of PCR amplification primers for amplifying the 16S-23S rRNA internal transcribed spacer (ITS) regions in the genomic DNA of the phylum Proteobacteria comprises:

i) SEQ ID NO: 6 as a forward primer; and ii) at least one reverse primer selected from the group consisting of
5'-AATCTCGGTTGATTTCTTTTCCT-3' (SEQ ID NO: 7),
5'-AATCTCGGTTGATTTCTTCTCCT-3' (SEQ ID NO: 8),
5'-AATCTCTTTTGATTTCTTTTCCTCG-3' (SEQ ID NO: 9),
5'-AATCTCATTTGATGTCTTTTCCTCG-3' (SEQ ID NO: 10),
5'-AATCTCTTTTGATTTCTTTTCCTTCG-3' (SEQ ID NO: 11),
5'-AATCTCTCTTGATTTCTTTTCCTTCG-3' (SEQ ID NO: 12), and
5'-AATCTCAATTGATTTCTTTTCCTAAGG-3' (SEQ ID NO: 13); and wherein at least one of said primers comprises a fluorescent label.

11. The method of claim 10, wherein said standard curve is based on at least five PCR calibrators of different length ranging in length from 50 to 1200 bps.

* * * * *

SEQUENCE LISTING

```
<160> NUMBER OF SEQ ID NOS: 17

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
ctggatcacc tcctttctaw g                                          21

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
ctggaacacc tcctttctgg a                                          21

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
aggcatccac cgtgcgccct                                            20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
aggcattcac crtgcgccct                                            20
```

```
<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
aggcatccrc catgcgccct                                              20

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
ccgcccgtca caccatgg                                                18

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
aatctcggtt gatttctttt cct                                          23

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
aatctcggtt gatttcttct cct                                          23

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
aatctctttt gatttctttt cctcg                                        25

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
aatctcattt gatgtctttt cctcg                                        25

<210> SEQ ID NO 11
<211> LENGTH: 26
<212> TYPE: DNA
<213> ORGANISM: Artificial Sequence
<220> FEATURE:
<223> OTHER INFORMATION: primer
```

```
<400> SEQUENCE: 11
aatctctttt gatttctttt ccttcg                                              26

<210> SEQ ID NO 12
<211> LENGTH: 26
<212> TYPE: DNA
<213> ORGANISM: Artificial Sequence
<220> FEATURE:
<223> OTHER INFORMATION: primer

<400> SEQUENCE: 12
aatctctctt gatttctttt ccttcg                                              26

<210> SEQ ID NO 13
<211> LENGTH: 27
<212> TYPE: DNA
<213> ORGANISM: Artificial Sequence
<220> FEATURE:
<223> OTHER INFORMATION: primer

<400> SEQUENCE: 13
aatctcaatt gatttctttt cctaagg                                             27

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
gacctagtgg aggaaagata c                                                   21

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
tccgtaggtg gcacgcggga                                                     20

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
gacctagtgg aggaaagata c                                                   21

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
tccgtaggtg gcacgcggga                                                     20
```